United States Patent
Collins et al.

(10) Patent No.: US 12,319,738 B2
(45) Date of Patent: *Jun. 3, 2025

(54) ANTI-FGFR2 ANTIBODIES IN COMBINATION WITH CHEMOTHERAPY AGENTS IN GASTRIC CANCER

(71) Applicant: Five Prime Therapeutics, Inc., South San Francisco, CA (US)

(72) Inventors: Helen L. Collins, Atherton, CA (US); James Hnatyszyn, Foster City, CA (US); Hong Xiang, Palo Alto, CA (US); Xiang Zhang, Burlingame, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 841 days.

This patent is subject to a terminal disclaimer.

(21) Appl. No.: 17/366,580

(22) Filed: Jul. 2, 2021

(65) Prior Publication Data

US 2022/0041737 A1 Feb. 10, 2022

Related U.S. Application Data

(63) Continuation of application No. 16/613,579, filed as application No. PCT/US2018/032757 on May 15, 2018, now Pat. No. 11,091,555.

(60) Provisional application No. 62/581,992, filed on Nov. 6, 2017, provisional application No. 62/507,053, filed on May 16, 2017.

(51) Int. Cl.
| | |
|---|---|
| C07K 16/28 | (2006.01) |
| A61K 9/00 | (2006.01) |
| A61K 31/282 | (2006.01) |
| A61K 31/513 | (2006.01) |
| A61K 31/519 | (2006.01) |
| A61K 39/00 | (2006.01) |
| A61K 39/395 | (2006.01) |
| A61P 35/00 | (2006.01) |
| A61P 35/04 | (2006.01) |

(52) U.S. Cl.
CPC ........ *C07K 16/2863* (2013.01); *A61K 9/0019* (2013.01); *A61K 31/282* (2013.01); *A61K 31/513* (2013.01); *A61K 31/519* (2013.01); *A61K 39/00* (2013.01); *A61K 39/3955* (2013.01); *A61P 35/00* (2018.01); *A61P 35/04* (2018.01); *A61K 2039/505* (2013.01); *A61K 2039/545* (2013.01); *C07K 2317/41* (2013.01); *C07K 2317/732* (2013.01); *C07K 2317/74* (2013.01); *C07K 2317/76* (2013.01); *C07K 2317/92* (2013.01)

(58) Field of Classification Search
CPC ............................................ C07K 16/2863
See application file for complete search history.

(56) References Cited

U.S. PATENT DOCUMENTS

| | | |
|---|---|---|
| 5,591,639 A | 1/1997 | Bebbington et al. |
| 5,707,632 A | 1/1998 | Williams et al. |
| 5,863,888 A | 1/1999 | Dionne et al. |
| 5,981,216 A | 11/1999 | Kenten et al. |
| 6,342,221 B1 | 1/2002 | Thorpe et al. |
| 6,946,292 B2 | 9/2005 | Kanda et al. |
| 7,214,775 B2 | 5/2007 | Hanai et al. |
| 7,297,493 B2 | 11/2007 | Lorenzi et al. |
| 7,425,446 B2 | 9/2008 | Kanda et al. |
| 7,708,992 B2 | 5/2010 | Hanai et al. |
| 7,737,325 B2 | 6/2010 | Kanda et al. |
| 7,872,016 B2 | 1/2011 | Eswarakumar et al. |
| 8,067,232 B2 | 11/2011 | Kanda et al. |
| 8,101,723 B2 | 1/2012 | Kim et al. |
| 8,263,074 B2 | 9/2012 | Sun et al. |
| 8,481,688 B2 | 7/2013 | Weng et al. |
| 8,603,987 B2 | 12/2013 | Kim et al. |
| 8,664,365 B2 | 3/2014 | Luehrsen et al. |
| 8,679,491 B2 | 3/2014 | Hanai et al. |
| 8,945,572 B2 | 2/2015 | Chant et al. |
| 9,140,689 B2 | 9/2015 | Byron et al. |
| 9,254,288 B2 | 2/2016 | Pollock |
| 9,260,525 B2 | 2/2016 | Chang et al. |
| 9,382,324 B2 | 7/2016 | Kim et al. |
| 9,415,118 B2 | 8/2016 | Batt et al. |
| 9,481,733 B2 | 11/2016 | Ohtsaka et al. |
| 9,498,532 B2 | 11/2016 | Batt et al. |
| 9,714,298 B2 | 7/2017 | Ohtsuka et al. |

(Continued)

FOREIGN PATENT DOCUMENTS

| | | |
|---|---|---|
| CN | 103096915 B | 8/2016 |
| EP | 2018442 A2 | 1/2009 |

(Continued)

OTHER PUBLICATIONS

Liu et al.—Biweekly Oxaliplatin in combination with continuous infusional 5-fluorouracil and Leucovorin (modified FOLFOX-4 regimen) as first-line chemotherapy for elderly patients with advanced gastric cancer. Am. J. Clin. Oncol. 31, 259-263,2008. (Year: 2008).*
Yung-Sung et al. A retrospective study of the safety and efficacy of a firstline treatment with modified FOLFOX-4 in unresectable advanced or recurrent gastric cancer patients. Chemotherapy, 58, 411-8, 2012. (Year: 2012).*
Dong et al. FOLFOX regimen in the patients with locally advanced or metastatic gastric cancer. Zhonghua zhong liu za zhi [Chinese journal of oncology], 31, 217-219, 2009. (Year: 2009).*
Mashkovsky M.D. Medicaments—16th ed., revised, corrected and supplemented—M.: Novaya volna, 2012. pp. 12-13.
Russian Application No. 2019141070/04, Office Action issued Mar. 4, 2022, 17 pages.

(Continued)

*Primary Examiner* — Elly-Gerald Stoica
(74) *Attorney, Agent, or Firm* — Melissa E. Karabinis

(57) ABSTRACT

This application relates to uses of antibodies against fibroblast growth factor receptor 2 (FGFR2), including antibodies against the FGFR2 isoform FGFR2-IIIb (also known as FGFR2b), in treatment of certain cancers in combinations with mFOLFOX6 chemotherapy.

12 Claims, 3 Drawing Sheets

Specification includes a Sequence Listing.

(56) References Cited

U.S. PATENT DOCUMENTS

| | | |
|---|---|---|
| 9,834,609 B2 | 12/2017 | Kim et al. |
| 10,172,937 B2 | 1/2019 | Harding et al. |
| 11,091,555 B2 | 8/2021 | Collins et al. |
| 2005/0147612 A1 | 7/2005 | Yayon et al. |
| 2007/0248605 A1 | 10/2007 | Hestir et al. |
| 2009/0068110 A1 | 3/2009 | Shang et al. |
| 2009/0170715 A1 | 7/2009 | Glinsky |
| 2009/0311250 A1 | 12/2009 | Chant et al. |
| 2010/0047251 A1 | 2/2010 | Yayon et al. |
| 2010/0111944 A1 | 5/2010 | Pollock et al. |
| 2010/0173323 A1 | 7/2010 | Strome et al. |
| 2010/0196364 A1 | 8/2010 | Kim et al. |
| 2011/0059091 A1 | 3/2011 | Chang et al. |
| 2011/0091473 A1 | 4/2011 | Golab et al. |
| 2011/0160216 A1 | 6/2011 | Lenz |
| 2011/0305687 A1 | 12/2011 | Weng et al. |
| 2011/0318373 A1 | 12/2011 | Sasikumar et al. |
| 2012/0258496 A1 | 10/2012 | Ellwanger et al. |
| 2013/0142802 A1 | 6/2013 | Chang et al. |
| 2013/0183288 A1 | 7/2013 | Reff et al. |
| 2013/0288305 A1 | 10/2013 | Weng et al. |
| 2013/0309250 A1 | 11/2013 | Cogswell et al. |
| 2014/0322220 A1 | 10/2014 | Harrenga et al. |
| 2015/0050273 A1 | 2/2015 | Harding et al. |
| 2015/0125454 A1 | 5/2015 | Ohtsuka et al. |
| 2015/0167101 A1 | 6/2015 | Chant et al. |
| 2015/0210769 A1 | 7/2015 | Freeman et al. |
| 2015/0366866 A1 | 12/2015 | Mahamed et al. |
| 2016/0009820 A1 | 1/2016 | Ohtsuka et al. |
| 2016/0130661 A1 | 5/2016 | Brooks et al. |
| 2016/0287699 A1 | 10/2016 | Karkera et al. |
| 2017/0008964 A1 | 1/2017 | Batt et al. |
| 2017/0145103 A1 | 5/2017 | Pierce et al. |
| 2018/0094063 A1 | 4/2018 | Kim et al. |
| 2019/0175730 A1 | 6/2019 | Harding et al. |

FOREIGN PATENT DOCUMENTS

| | | |
|---|---|---|
| EP | 1423428 A2 | 8/2009 |
| EP | 2046384 A2 | 12/2009 |
| EP | 2569012 A2 | 10/2013 |
| EP | 2603521 A2 | 10/2014 |
| EP | 2782934 A1 | 10/2014 |
| EP | 2837685 A1 | 2/2015 |
| EP | 2871236 A1 | 5/2015 |
| EP | 3008210 A1 | 4/2016 |
| JP | 2013534922 A | 9/2013 |
| KR | 1020040020107 | 3/2004 |
| RU | 2009107895 A | 9/2010 |
| TW | 201345924 A | 11/2013 |
| TW | 201536804 A | 10/2015 |
| TW | 201536808 A | 10/2015 |
| WO | 0061739 | 10/2000 |
| WO | 01079266 A1 | 10/2001 |
| WO | 0231140 | 4/2002 |
| WO | 2002102972 A2 | 12/2002 |
| WO | 2003063893 A2 | 8/2003 |
| WO | 03/080672 A1 | 10/2003 |
| WO | 03080672 W | 10/2003 |
| WO | 2005066211 A2 | 7/2005 |
| WO | 2007134210 A2 | 11/2007 |
| WO | 07144893 A2 | 12/2007 |
| WO | 2007144893 A2 | 12/2007 |
| WO | 2008017963 A2 | 2/2008 |
| WO | 2008042236 A2 | 4/2008 |
| WO | 2008052796 A1 | 5/2008 |
| WO | 2008065543 A2 | 6/2008 |
| WO | 2009052830 A1 | 4/2009 |
| WO | 09100105 A2 | 8/2009 |
| WO | 2010040571 A2 | 4/2010 |
| WO | 2010054265 | 5/2010 |
| WO | 11025814 A1 | 3/2011 |
| WO | 2011088196 A2 | 7/2011 |
| WO | 2011143318 A2 | 11/2011 |
| WO | 2011161699 A2 | 12/2011 |
| WO | 2012021841 A2 | 2/2012 |
| WO | 2012045085 A1 | 4/2012 |
| WO | 2012162561 A2 | 11/2012 |
| WO | 2012162561 A3 | 5/2013 |
| WO | 2013076186 A1 | 5/2013 |
| WO | 2013087716 A2 | 6/2013 |
| WO | 2013148263 A1 | 10/2013 |
| WO | 2013154206 A1 | 10/2013 |
| WO | 2014089193 A1 | 6/2014 |
| WO | 2014160160 A2 | 10/2014 |
| WO | 2014179448 | 11/2014 |
| WO | 2014197937 A1 | 12/2014 |
| WO | 2015017600 A1 | 2/2015 |
| WO | 2015112900 A1 | 7/2015 |
| WO | 2015116868 A2 | 8/2015 |
| WO | 2016073789 A2 | 5/2016 |
| WO | 2016100882 A1 | 6/2016 |
| WO | 2017091577 A1 | 6/2017 |

OTHER PUBLICATIONS

Bendell, et al., "FPA144-001: A first in human study of FPA 144, an ADCC-enhanced, FGFR2b isoform-selective monoclonal antibody in patients with advanced solid tumors", Journal of Clinical Oncology, vol. 34, Issue 4 (2016).

European Patent Office Application No. 18730518.0 Examination Report, Jan. 18, 2022, 4 pages.

Wong et.al., "Enhancement of DNA Uptake in FUT8-Deleted CHO Cells for Transient Production of Afucosylated Antibodies" 2010, Biotechnology and Bioengineering, V.106, N.5, pp. 751-763.

Wu, H. et al., "Humanization of a Murine Monoclonal Antibody by Simultaneous Optimization of Framework and CDR Residues," J. Mol. Biol., 294: 151-162 (1999).

Xiang et al., "Population pharmacokinetic analysis of phase 1 bemarituzumab data to support phase 2 gastroesophageal adenocarcinoma FIGHT trial," Cancer Chemotherapy and Pharmacology, 2020, 86:595-606.

Yamane-Ohnuki N, et al., "Production of therapeutic antibodies with controlled fucosylation," MABS, Jun. 2009, 1(3):230-236.

Yashiro et al., "Establishment of two new scirrhous gastric cancer cell lines: analysis of factors associated with disseminated metastasis," Br J Cancer, 72:1200-1210 (1995).

Yashiro, M. et al. "Synergistic antitumor effects of FGFR2 inhibitor with 5-fluorouracil on scirrhous gastric carcinoma", International Journal of Cancer, 126(4): 1004-1015 (2010).

Yoshino, et al., "Keratinocyte growth factor receptor expression in normal colorectal epithelial cells and differentiated type of colorectal cancer," Oncology Reports, 13:247-252, (2005).

Zak et al., "Structure of the Complex of Human Programmed Death 1, PD-1, and its Ligand PD-L1," Structure, 2015, 23(12): 2341-2348.

Zhang et al., "Research Status and Development Trend of Tumor Drugs of the FGFR Antibody Class." Biotechnology & Business, 2014, 3:7-12.

Zhang et al., "Receptor specificity of the fibroblast growth factor family. The complete mammalian FGF family," J Biol Chem, 281:15694-156700, (2006).

Zhao et al., "Another Approach: Anti-FGFR2 MABs" Proc Am Assoc Cancer Res., Denver, CO Poster Presentation No. 1236, Apr. 18-22, 2009.

Zhao et al., "Monoclonal antibodies to fibroblast growth factor receptor 2 effectively inhibit growth of gastric tumor xenografts," Clin Cancer Res, 16:5750-5758, (2010).

Zitvogel et al., Targeting PD-1/PD-L1 Interactions for Cancer Immunotherapy, OncoImmunology, 2012, 1(8):1223-1225.

Niwa R. "IgG subclass-independent improvement of antibody-dependent cellular cytotoxicity by fucose removal from Asn297-linked oligosaccharides," Journal of Immunological Methods, Sep. 22, 2005, 306:151-160.

Office Action issued in Japanese Patent Application No. 2016-531878 dated Aug. 7, 2018.

Office Action issued in Russian Patent application No. 2016106101, dated Oct. 9, 2018.

(56) References Cited

OTHER PUBLICATIONS

Ogle, R. et al., "Regulation of Cranial Suture Morphogenesis," Cells Tissues Organs, 176: 54-66 (2004).
Ornitz et al., "Fibroblast growth factors," Genome Biol, 2:REVIEWS3005, (2001).
Ornitz et al., "Receptor specificity of the fibroblast growth factor family," J Biol Chem, 271:15292-15297, (1996).
Otte, et al., "Expression of keratinocyte growth factor and its receptor in colorectal cancer," European Journal of Clinical Investigation, 30:222-229, (2000).
Pascal et al., "Correlation of mRNA and protein levels: Cell type-specific gene expression of cluster desianation antiaens in the prostate," BMC Genomics, 9:246, 13 pages, (2008).
PCT/US2009/063647 International Preliminary Report on Patentability and Written Opinion issued May 10, 2011.
PCT/US2009/063647 International Search Report mailed Jun. 23, 2010.
Pearson et al., "High-Level Clonal FGFR Amplification and Response to FGFR Inhibition in a Translational Clinical Trial," Cancer Discovery, 2016, 6(8): 838-851.
Pectasides, D. et al. "Randomized phase III clinical trial comparing the combination of pacecitabine and oxaliplatin (CAPOX) with the combination of 5-fluorouracil, leucovorin and oxaliplatin (modified FOLFOX6) as adjuvant therapy in patients with operated high-risk stage II or stage III colorectal cancer" BMC Cancer, 15(1):384 (2015).
Pellegrinet, L. et al. "DII1- and DII4-mediated Notch signaling are required for homeostasis of intestinal stem cells" Gastroenterology 140: 1230-1240 (2011).
Pollock et al., "Frequent activating FGFR2 mutations in endometrial carcinomas parallel germline mutations associated with craniosynostosis and skeletal dysplasia syndromes," Oncogene, 26:7158-7162, (2007).
Powles et al., "MPDL3280A (anti-PD-L1) treatment leads to clinical activity in metastatic bladder cancer" Nature 515:558-563 (Year: 2014).
Presta, M. et al., "Fibroblast Growth Factor/Fibroblast Growth Factor Receptor System in Angiogenesis," Cytokine & Growth Factor Reviews, 16: 159-178 (2005).
R&D Systems online catalog page for MAB665 dated Mar. 1, 2005.
Reusch, D. et al., "Fc Glycans of Therapeutic Antibodies as Critical Quality Attributes," Glycobiol., advance access published Sep. 12, 2015, pp. 1-10 (2015).
Ricol, David et al. "Tumour suppressive properties of fibroblast growth factor receptor 2-IIIB in human bladder cancer" Oncogene 18:7234-7243 (1999).
Rudikoff et al., "Single amino acid substitution altering antigen-binding specificity," Proceedings of the National Academy of Sciences, 79:1979-1983, (1982).
Schuster, M. et al. "Improved effector functions of a therapeutic monoclonal Lewis Y-specific antibody by glycoform engineering" Cancer Res. 65(17): 7934-41 (2005).
Shields, R. L. et al. "Lack of fucose on human IgG1 N-linked oligosaccharide improves binding to human Fcgamma RIII and antibody-dependent cellular toxicity" J. Biol. Chem., vol. 277, No. 30, 2002, pp. 26733-26740.
Shire: "Formulation of proteins and monoclonal antibodies mAbs", Monoclonal Antibodies: Meeting the Challenges in Manufacturing, Formulation, Delivery and Stability of Final Drug Product, Jan. 1, 2015, pp. 93-120.
Sibertin-Blanc, C. et al. "Monoclonal antibodies for treating gastric cancer: promises and pitfalls", Expert Opinion on Biological Therapy. 16(6): 759-769 (2016).
Steele et al., "Induction of FGF receptor 2-IIIb expression and response to its ligands in epithelial ovarian cancer," Oncogene, 20:5878-5887, (2001).
Supplementary European Search Report and European Search Opinion for application EP09825523 mailed May 7, 2012.
Suzuki, E. et al. "A nonfucosylated anti-HER2 antibody augments antibody-dependent cellular cytotoxicity in breast cancer patients" Clin. Cancer Res., vol. 13, No. 6, 2007, pp. 1875-1882.
Takeda, M. et al., "AZD2171Shows Potent Antitumor Activity Against Gastric Cancer Over-Expressing Fibroblast Growth Factor Receptor 2/Keratinocyte Growth Factor Receptor," Clin. Cancer Res., 13(10): 3051-3057 (2007).
Tamaru et al., "Estrogen receptor-associated expression of keratinocyte growth factor and its possible role in the inhibition of apoptosis in human breast cancer," Lab. Invest, 84(11 ):1460-1471, (2004).
Tannheimer et al., "Characterization of Fibroblast Growth Factor Receptor 2 Overexpression in the Human Breast Cancer Cell Line SUM-52 PE," Breast Cancer Res, 2:311-320 (2000).
Tiong, Kai Hung et al. "Functional roles of fibroblast growth factor receptors (FGFRs) signaling in human cancers" Apoptosis 18:1447-1468 (2013).
Trudel et al., "The inhibitory anti-FGFR3 antibody, PRO-001, is cytotoxic to t(4;14) multiple myeloma cells," Blood, 107:4039-4046, (2006).
Tsujimoto et al., "Amplification of Growth Factor Receptor Genes and DNA Ploidy Pattern in the Progression of Gastric Cancer," Virchows Arch 431 :383-389, (1997).
U.S. Appl. No. 12/614,282, Non-Final Rejection mailed Apr. 7, 2011.
U.S. Appl. No. 12/614,282, Notice of Allowance mailed Sep. 29, 2011.
U.S. Appl. No. 12/614,282, Requirement for Restriction/Election mailed Dec. 27, 2010.
Uchiyama, "Liquid formulation for antibody drugs", Biochimica Et Biophysica Acta (BBA)—Proteins & Proteomics, Elsevier, Netherlands, vol. 1844, No. 11, Aug. 13, 2014 (Aug. 13, 2014), pp. 2041-2052.
Ueda et al., "Deletion of the Carboxyl-Terminal Exons of K-sam/FGFR2 by Short Homology-Mediated Recombination, Generating Preferential Expression of Specific Messenger RNAs," Cancer Res., 59:6080-6086, (1999).
Vajdos et al., "Comprehensive functional maps of the antigen-binding site of an anti-ErbB2 antibody obtained with shotgun scanning mutagenesis," J. Mol. Biol., 320:415-428, (2002)—Ordered Jun. 2011 from Reprints desk.
Van Cutsem et al., "A randomized, open-label study of the efficacy and safety of AZD4547 monotherapy versus paclitaxel for the treatment of advanced gastric adenocarcinoma with FGFR2 polysomy or gene amplification," Anals of Oncology, 28: 1316-24 (2017).
Visco et al., "Expression of keratinocyte growth factor receptor compared with that of epidermal growth factor receptor and erbB-2 in endometrial adenocarcinoma," Int. J. Oncol., 15(3):431-435, doi: https://doi.org/10.3892/ijo.15.3.431, (1999).
Von Horsten et.al. "Production of non-fucosylated antibodies by co-expression of heterologous GDP-6-deoxy-D-lyxo-4-hexulose reductase" 2010, Glycobiology, v.20 n.12 pp. 1607-1618.
Wainberg et al., "Randomized Double-blind Placebo-Controlled Phase 2 Study of Bemarituzumab Combined with Modified FOLFOX6 (mFOLFOX6) in 1st Line (1L) Treatment of Advanced Gastric/Gastroesophageal Junction Adenocarcinoma (FIGHT)," Abstract, ASCO-GI, Jan. 15, 2021, 2 pages.
Wainberg et al., "A double-blind randomized study of bemarituzumab (bema) plus mFOLFOX6 versus placebo plus mFOLFOX6 as first-line treatment for advanced gastric/gastroesophageal junction cancer (FIGHT)," Late Breaking Abstract (LBA160), ASCO Gastrointestinal Cancer Symposium 2021, 15 pages.
Wang et al., "A phase II study of a modified FOLFOX6 regimen as neoadjuvant chemotherapy for locally advanced gastric cancer," British J Cancer, 2016, 114:1326-1333.
Wang,L. et al., "Abstract #1236: Blocking antibody to fibroblast growth factor-2 as a potential cancer therapeutic agent," 100th AACR Annual Meeting, Apr. 18-22, 2009, Denver, CO, Cancer Res., 69: 1236 (2009).
Watanabe, et al., "Overexpression of keratinocyte growth factor in cancer cells and enterochromaffin cells in human colorectal cancer," Pathology International, 50:363-372, (2000).

(56) References Cited

OTHER PUBLICATIONS

Wei, P. et al., "Generation and Characterization of Monoclonal Antibodies to Human Keratinocyte Growth Factor Receptor," Hybridoma, 25(3): 115-124 (2006).
Werner, "Molecular and Cellular Mechanisms of Tissue Repair", Experimental Dermatology, 14(10):786-787, (2005).
Winter, et al., "Humanized antibodies," Immunology Today, 14(6):243-246, (1993)—Ordered Jun. 2011 from Reprints desk.
CA 3,062,177 Office Action (Sep. 27, 2023).
Tamura et al., "Structural Correlates of an Anticarcinoma Antibody: Identification of Specificity-Determining Residues (SDRs) and Development of a Minimally Immunogenic Antibody Variant by Retention of SDRs Only", J Immunol, 164(3), pp. 1432-1441, Feb. 1, 2000 (Jan. 2, 2000).
Gratz, G. "Final Report: A Twenty-eight Day Intravenous Toxicity Study of FPA144-A and FPA144-F in Cynomolgus Monkeys, Study No. 0787-12157," Test Facility: BASi, Mt. Vernon, IN, report completed Jun. 27, 2014 (295 pages).
Gratz, G. "Final Report: A Twenty-eight Day Intravenous Toxicity Study of FPA144-A and FPA144-F in Rats, Study No. 0787-12212," Test Facility: BASi, Mt. Vernon, IN, report completed Jun. 27, 2014 (483 pages).
Gratz, G. "Final Report: Single Dose Intravenous Pharmacokinetic Study of FPA144-A and FPA144-F in Cynomolgus Monkeys, Study No. 0787-12156," Test Facility: BASi, Mt. Vernon, IN, report completed Jun. 26, 2014 (133 pages).
Grose et al., "The Role of Fibroblast Growth Factor Receptor 2b in Skin Homeostasis and Cancer Development," The Embo Journal, 26:1268-1278 (2007).
Grose, R. et al., "Fibroblast Growth Factor Signaling in Tumorigenesis," Cytokine & Growth Factor Reviews, 16: 179-186 (2005).
Grothey, A., "Bemarituzumab plus modified FOLFOX6 for advanced gastric/GE junction adenocarcinoma," Oncology (/explore/channel/oncology/sp1), Expert Opinion, Interview, Feb. 10, 2021, 4 pages.
Guggenheim, Analyst Report on Five Prime Therapeutics, Inc., Nov. 11, 2020 (6 pages).
Hacibekiroglu et al., "Comparative analysis of the efficacy and safety of modified FOLFOX-6 and DCF regimens as first-line treatment in advanced gastric cancer," Mol Clin Oncol, 2015, 3:1160-1164.
Hattori et al., "Immunohistochemical detection of K-sam protein in stomach cancer," Clin Cancer Res, 2:1373-81, (1996).
Holt, L. et al., "Domain Antibodies: proteins for therapy," Trends in Blotech., 21(11): 484-490 (2003).
Hughes, "Differential Expression of the Fibroblast Growth Factor Receptor (FGFR) Multigene Family in Normal Human Adult Tissues," J Histochem cytochem, 45:1005-1019 (1997).
Hunter et al., "A Genome-Wide Association Study Identifies Alleles in FGFR2 Associated With Risk of Sporadic Postmenopausal Breast Cancer," Nature Genetics, 39:870-874, (2007).
Ibrahimi et al., "Biochemical Analysis of Pathogenic Ligand-Dependent FGFR2 Mutations Suggests Distinct Pathophysiological Mechanisms for Craniofacial and Limb Abnormalities," Human Molecular Genetics, 13:2313-2324, (2004).
International Search Report and Written Opinion for PCT/US2018/032757 dated Aug. 10, 2018.
International Search Report and Written Opinion issued in PCT/US2016/06332 on Feb. 27, 2017.
International Search Report and Written Opinion issued in PCT/US2016/063340 on Feb. 24, 2017.
International Search Report and Written Opinion of PCT/US2019/054684, dated Jan. 29, 2020, 14 pages.
International Search Report and Written Opinion of the International Searching Authority for International Application No. PCT/US2014/049008, date of mailing of Nov. 11, 2014.
Itoh et al., "Preferential Alternative Splicing in Cancer Generates a K-sam Messenger RNA with Higher Transforming Activity," Cancer Res., 54:3237-3241, (1994).
J.P. Morgan, Analyst Report on Five Prime Therapeutics, Inc., Nov. 11, 2020 (10 pages).

Jang et al., "Mutations in Fibroblast Growth Factor Receptor 2 and Fibroblast Growth Factor Receptor 3 Genes Associated with Human Gastric and Colorectal Cancers," Cancer Res., 61 :3541-3543, (2001 ).
Jefferies, Analyst Report on Five Prime Therapeutics, Inc., Nov. 10, 2020 (10 pages).
Jefferis, "Antibody Therapeutics: Isotype and Glycoform Selection," Expert. Opin. Biol. Ther., 2007, 7(9):1401-1413.
Junttila, T. et al., "Superior In vivo Efficacy of Afucosylated Trastuzumab in the Treatment of HER2-Amplified Breast Cancer," Cancer Res., 70(11): 4481-4489 (2010).
Kanda et al. "Comparison of Cell Lines for Stable Production of Fucose-Negative Antibodies With Enhanced ADCC" Biotechnology and Bioengineering, 94(4): 680-688 (2006).
Katoh "Cancer genomics and genetics of FGFR2 (Review)," Int J Oncology, 33:233-237, (2008).
Katoh, "FGFR Inhibitors: Effects on Cancer Cells, Tumor Microenvironment and Whole-Body Homeostasis (Review)", Intl J Mol Med, 2016, 38:1-15.
Keam, B. et al. "Modified FOLFOX-6 chemotherapy in advanced gastric cancer: Results of phase II study and comprehensice analysis of polymorphisms as a predictive and prognostic marker" BMC Cancer 2008, 8:148.
Kim et al., "Oxaliplatin, 5-fluorouracil and leucovorin (modified FOLFOX-6) as first-line chemotherapy for advanced gastric cancer patients with poor performance status," Oncology Letters, 2012, 3:425-428.
Kono et al., "Impaired Antibody-Dependent Cellular Cytotoxicity Mediated by Herceptin in Patients with Gastric Cancer," Cancer Res 62:5813-5817, (2002).
Kunii et al., "FGFR2-amplified gastric cancer cell lines require FGFR2 and Erbb3 signaling for growth and survival," Cancer Res, 68:2340-2348, (2008).
Kurban, et al., "Expression of keratinocyte growth factor receptor (KGFR/FGFR2 nib) in human uterine cervical cancer," Oncology Reports, 11:987-991, (2004).
Lazar, G. et al. "Engineered antibody Fc variants with enhaced effector funtion" PNAS USA 103(11): 4005-4010.
Liang et al., "Genetic Variants in Fibroblast Growth Factor Receptor 2 (FGFR2) Contribute to Susceptibility of Breast Cancer in Chinese Women," Carcinoaenesis, 29: 2341-2346, (2008).
Lo et al., Effector-attenuating substitutions that maintain antibody stability and reduce toxicity in mice, J. Biol. Chem, 292(9): 3900-08 (2017).
Lote et al., "PD-1 and PD-L1 blockade in gastrointestinal malignancies," Cancer Treatment Reviews, 2015, 41:893-903.
Luqmani et al., "Expression of Basic Fibroblast Growth Factor, FGFR1 and FGFR2 in Normal and Malignant Human Breast, and Comparison with Other Normal Tissues," Br. J. Cancer, 66:273-280, (1992).
Maccallum, R. et al., "Antibody-antigen Interactions: Contact analysis and binding site topography," J. Mol. Biol., 262: 732-745 (1996).
Masayuki et al., "AZD2171 Shows Potent Antitumor Activity Against Gastric Cancer Over-Expressing Fibroblast Growth Factor Receptor 2/Keratinocyte Growth Factor Receptor," Clinical Cancer Research, 13(10):3051-3057, (2007).
Matsunobu et al., "Expression of Keratinocyte Growth Factor Receptor Correlates with Expansive Growth and Early Stage of Gastric Cancer," International Journal of Oncology, 28:307-314, (2006).
Mckay et al., "Tolerance to single, but not multiple, amino acid replacements in antibody V-HCDR2: A means of minimizing B cell wastage from somatic hypermutation?," Journal Of Immunology, 156(9):3285-3291, (1996).
Miki, et al., "Determination of ligand-binding specificity by alternative splicing: Two distinct growth factor receptors encoded by a single gene," Proc. Natl. Acad. Sci. USA, Biochemistry, 89:246-250, (1992).
Mohammadi, M. et al., "Structural Basis for Fibroblast Growth Factor Receptor Activation," Cytokine & Growth Factor Reviews, 16: 107-137 (2005).
Moloney et al., "Exclusive Paternal Origin of New Mutations in Apert Syndrome," Nature Genetics, 13:48-53, (1996).

(56) References Cited

OTHER PUBLICATIONS

Mor et al., "DNA Amplification in Human Gastric Carcinomas," Cancer Genet Cytogenet, 65:111-114, (1993).
Mor et al., "Novel DNA Sequences at Chromosome 1 0Q26 Are Amplified in Human Gastric Carcinoma Cell Lines: Molecular Cloning by Competitive DNA Reassociation," Nucleic Acids Research, 19:117-123, (1991.
Nakamura et al., "A novel molecular targeting compound as K-samII/FGF-R2 phosphorylation inhibitor, Ki23057, for scirrhous gastric cancer," Gastroenterology, 131:1530-1541, (2006).
Nakatani et al., "Isolation of an Amplified DNA Sequence in Stomach Cancer," Jpn J. Cancer Res., 81:707-710, (1990).
Naoko Y-O and et.al, Production of therapeutic antibodies with controlled fucosylation, MAbs, 2009; V.1, pp. 230-236.
NCT02318329, Sponsor Five Prime Therapeutics, Inc., "Open-label, dose-finding study evaluating safety and PK of FPA144 in patients with advanced solid tumors," available at clinicaltrials (dot) gov, Jan. 2017 (last viewed May 25, 2017).
Brown, M. et al., "Tolerance to Single, but Not Multiple, Amino Acid Replacements in Antibody VH CDR2," J. Immunol., 156: 3285-3291, 1996.
"Monoclonal Anti-human FGF R2 Antibody," R&D Systems Product Description, Catalog No. MAB665, Clone 98707, Lot No. DWH02, printed Mar. 1, 2005, 2 pages.
"Potelligent® CHOK1SV." Lonza. Web.
ACTIP, monoclonal antibodies approved by the EMA and FDA for therapeutic use, available at: http://www.ACTIP.org/products/monoclonal-antibodies-approved-by-the-ema-and-fda-for-therapeutic-use/, 10 pages, last viewed May 18, 2018.
Adelaide et al., "Integrated Profiling of Basal and Luminal Breast Cancers," Cancer Res., 67:11565-11575, (2007).
Ahmad, Imran, et al. "Mechanisms of FGFR-mediated carcinogenesis" Biochimica et Biophysica Acta, 1823(4):850-860 (2012).
Amgen Press Release, "Amgen to Acquire Five Prime Therapeutics for $1.9 Billion in Cash," Mar. 4, 2021 (8 pages).
Amgen Press Release, "Amgen's Investigational Targeted Treatment Bemarituzumab Granted Breakthrough Therapy Designation," Apr. 19, 2021 (7 pages).
Anonymous, "Five Prime announces bemarituzumab plus chemotherapy demonstrates significant progression-free and overall survival benefit compared to placebo plus chemotherapy in front-line advanced gastric and gastrointestinal junction cancer," press release Nov. 10, 2020, available at www(dot)fiveprime(dot)com. (3 pages).
Anonymous: "Five Prime Therapeutics Initiates Phase Patient Dosing in Phase 1 Lead-In to Phase 3, Global Registrational Trial of FPA144 in Front-Line Advanced Gastric Cancer" Five Prime, Jan. 2, 2018, p. 1-2, retrieved from the internet: Retrieved from the URL:http://investor.fiveprime.com/news-releases/news-release-details/five-prime-therapeutics-initiates-patient-dosing-phase-1-lead.
Bai et al., "GP369, an FGFR2-IIIb-specific antibody, exhibits potent antitumor activity against human cancers driven by activated FGFR2 signaling," Cancer Res., 70:7630-7639, (2010).
Beer et al., "Expression and Function of Keratinocyte Growth Factor and Activin in Skin Morphogenesis and Cutaneous Wound Repair," Journal of Investigative Dermatology Symposium Proceedings, 5:34-39 (2000).
Beer et al., "Fibroblast Growth Factor (FGF) Receptor 1-IIIb Is a Naturally Occurring Functional Receptor for FGFs That is Preferentially Expressed in the Skin and the Brain," J Biol Chem, 275:16091-16097 (2000).
Bendell et al., FPA144-001: A First Human Study of FPA144, and ADCC-enhanced, FGFR2b Isoform-selective Monoclonal Antibody in Patients with Advanced Solid Tumors ASCO Gastrointestinal Cancers Symposium, Jan. 2016, poster #140 (Year: 2016).
Byron et al., "Inhibition of Activated Fibroblast Growth Factor Receptor 2 in Endometrial Cancer Cells Induces Cell Death Despite PTEN Abrogation," Cancer Res., 68:6902-6907, 2008).
Campbell, "General properties and applications of monoclonal antibodies," Monoclonal Antibody Technology, pp. 1-32, (1984).
Carter et al., "Identification and validation of cell surface antigens for antibody targeting in oncology," Endocrine-Related Cancer, 11:659-687, (2004).
Casset, F. et al., "A Peptide Mimetic of an Anti-CD4 Monoclonal Antibody by Rational Design," Biochem. Biophys. Res. Comm., 307: 198-205 (2003).
Catenacci et al., "Phase 1 Escalation and Expansion Study of Bemarituzumab (FPA144) in Patients with Advanced Solid Tumors and FGFR2b-Selected Gastroesophageal Adenocarcinoma," J Clin Oncol, 2020, 1-10.
Catenacci, D.V.T. et al. "Updated antitumor activity and safety of FPA144, an ADCC-enhanced, FGFR2b isoform-specific monoclonal antibody, in patients with FGFR2b+ gastric cancer" 2017 ASCO Annual Meeting, Poster No. 4067, (Jun. 2, 2017).
Catenacci, D.V.T. et al. "Updated antitumor activity and safety of FPA144, an ADCC-enhanced, FGFR2b isoform-specific monoclonal antibody, in patients with FGFR2b+ gastric cancer" 2017 ASCO Annual Meeting, Abstract No. 4067, J. Clin. Oncol. 35(Suppl): Abst. 4067 (May 17, 2017).
Chao, J., "Adding bemarituzumab to chemotherapy improves outcomes in certain gastric cancers," available at: www.healio.com/news/hematology-oncology/20210120/, Jan. 20, 2021, 3 pages.
Chen, Y. et al., "Selection and Analysis of an Optimized Anti-VEGF Antibody: Crystal Structure of an Affinity-matured Fab in Complex with Antigen," J. Mol. Biol., 293: 865-881 (1999).
Cho et al., "Enhanced Expression of Keratinocyte Growth Factor and Its Receptor Correlates with Venous Invasion in Pancreatic Cancer," Am. J. Pathol., 170(6):1964-1974, doi: http://dx.doi.org/10.2353/ajpath.2007.060935, (2007).
Clarivate Analytics, Cortellis internet portal printed pages (https://www.cortellis.com/intelligence/advsearch/view.do), two pages, Jul. 20, 2018.
Clarivate Analytics, Cortellis search results for search query: (afucosyl* or non-fucosyl* or non fucosylation) and monocolonal and antibody, four pages, Jul. 20, 2018.
Davies et al., "Somatic Mutations of the Protein Kinase Gene Family in Human Lung Cancer," Cancer Res., 65:7591-7595, (2005).
Davies, J. et al., "Affinity Improvement of Single Antibody VH Domains: residues in all three hypervariable regions affect antigen binding," Immunotech., 2: 169-179 (1996).
De Moerlooze et al., "An important role for the IIIb isoform of fibroblast growth factor receptor 2 (FGFR2) in mesenchymal-epithelial signalling during mouse organogenesis," Development, 127:483-492, (2000).
De Pascalis et al., "Grafting of abbreviated complementarity determining regions containing specificity determining residues essential for ligand contact to engineer a less immunogenic humanized monoclonal antibody," Journal of Immunology, 169: 3076-3084, (2002).
Declaration of Dr. Kristen Pierce, Sep. 15, 2017.
Dr. Kristen Pierce 2017 CV.
Dutt et al., "Drug-sensitive FGFR2 mutations in endometrial carcinoma," Proc Natl Acad Sci USA, 105:8713-7, (2008).
Easton et al., "Genome-wide Association Study Identifies Novel Breast Cancer Susceptibility Locus," Nature, 447:1087-1093, (2007).
Eswarakumar, V.P. et al. "Cellular signaling by fibroblast growth factor receptors" Cytokine & Growth Factor Reviews 16: 139-149 (2005).
Fedyanin M. Yu et al., Prospects of therapeutic action on FGFR signaling pathway. Advances of molecular oncology. 2015, No. 1, pp. 27-38 entire text.
File History of U.S. Appl. No. 15/358,756, filed Nov. 22, 2016.
File History of U.S. Appl. No. 15/358,941, filed Nov. 22, 2016.
File History of U.S. Appl. No. 16/181,784, filed Nov. 6, 2018.
File History of U.S. Appl. No. 16/613,579, filed Nov. 14, 2019.
File History of U.S. Appl. No. 17/282,589, filed Apr. 2, 2021.
File History of U.S. Appl. No. 14/447,751, filed Jul. 31, 2014.
Finch and Rubin, "Keratinocyte Growth Factor Expression and Activity in Cancer: Implications For Use in Patients with Solid Tumors," Journal of the National Cancer Institute, 98:812-824 (2006).

(56) References Cited

OTHER PUBLICATIONS

Five Prime Corporate Overview, "Rewriting cancer, together," Jan. 2021, 36 pages.

Fortin, D. et al., "Distinct Fibroblast Growth Factor (FGF)/FGF Receptor Signaling Pairs Initiate Diverse Cellular Responses in the Oligodendrocyte Lineage," J. Neurosci., 25(32): 7470-7479 (2005).

Gemo, et al. "Abstract 5446: FPA144L A therapeutic antibondy for treating patients with gastric cancers bearing FGFR2 gene amplifications" Cancer Research, 74(19):1-4 (2014).

Gemo, et al. "FPA144: A Therapeutic Antibody for Treating Patients with Gastric Cancers Bearing FGFR2 Gene Amplification" AACR Abstract No. 5446, Apr. 2014.

Genbank Accession No. AAF26719, "Fibroblast growth factor receptor 2 IIIb [Ovis aries]," Nov. 17, 2000 (1 page).

Genbank Accession No. ABI81225, "Fibroblast growth factor receptor 1 IIIc [Ovis aries]," Mar. 5, 2008 (1 page).

Gong et al., "Increased in vivo effector function of human IgG4 isotype antibodies through afucosylation," Monoclonal Antibodies 8(6): 1098-1106 (2016).

Hinton, P.R. et al., An engineered human IgG1 antibody with longer serum half-life. J Immunol. (Jan. 1, 2006);176(1):346-56.

MX Application MZX/a/2019/013329, Office Action, (Oct. 9, 2023).

Naider, F. et al., Peptides in the treatment of AIDS. Current Opinion in Structural Biology, (Aug. 19, 2009); 473-82.

Tudor, D., et al., The broadly neutralizing HIV-1 IgG 2F5 elicits gp41-specific antibody-dependent cell cytotoxicity in a FcyRI-dependent manner. AIDS. (Mar. 27, 2011); 25(6):751-9.

Wainberg, Zev, et al., Bemarituzumab as first-line treatment for locally advanced or metastatic gastric/gastroesophageal junction adenocarcinoma: final analysis of the randomized phase 2 FIGHT trial, Gastric Cancer, pp. 558-570, 2024.

* cited by examiner

Dose Level 2 (n=3-6):
anti-FGFR2-IIIb 15 mg/kg D1
Oxaliplatin 85 mg/m2 D1,
Leucovorin 400 mg/m2 D1,
5-FU 2400 mg/m2 D 1-2
Every 2 weeks

Dose Level 1 (n=3-6):
anti-FGFR2-IIIb 10 mg/kg D1
Oxaliplatin 85 mg/m2 D1,
Leucovorin 400 mg/m2 D1,
5-FU 2400 mg/m2 D 1-2
Every 2 weeks

Dose Level -1 (n=3-6):
anti-FGFR2-IIIb 6 mg/kg D1
Oxaliplatin 85 mg/m2 D1,
Leucovorin 400 mg/m2 D1,
5-FU 2400 mg/m2 D 1-2
Every 2 weeks

FIG. 1

ANTI-FGFR2 ANTIBODIES IN COMBINATION WITH CHEMOTHERAPY AGENTS IN GASTRIC CANCER

CROSS-REFERENCE TO RELATED APPLICATIONS

This application is a continuation of U.S. application Ser. No. 16/613,579, filed Nov. 14, 2019, which is a national phase entry pursuant to 35 U.S.C. § 371 of International Application No. PCT/US2018/032757, filed May 15, 2018, which claims the benefit of priority of U.S. Provisional Application No. 62/507,053, filed on May 16, 2017, and U.S. Provisional Application No. 62/581,992, filed on Nov. 6, 2017, and each of which are incorporated by reference in their entirety.

FIELD

This application relates to uses of antibodies against fibroblast growth factor receptor 2 (FGFR2), including antibodies against the FGFR2 isoform FGFR2-IIIb (also known as FGFR2b), in treatment of certain cancers in combinations with mFOLFOX6 chemotherapy.

BACKGROUND

The fibroblast growth factor (FGF) family members bind to four known tyrosine kinase receptors, fibroblast growth factor receptors 1-4 (FGFR1-4) and their isoforms, with the various FGFs binding the different FGFRs to varying extents (Zhang et al., *J. Biol. Chem.* 281:15694, 2006). A protein sequence of human FGFR2 is provided in, e.g., GenBank Locus AF487553. Each FGFR consists of an extracellular domain (ECD) comprising three immunoglobulin (Ig)-like domains (D1, D2 and D3), a single transmembrane helix, and an intracellular catalytic kinase domain (Mohammadi et al., *Cytokine Growth Factor Revs*, 16:107, 2005). FGFs bind to the receptors primarily through regions in D2 and D3 of the receptors. There is a contiguous stretch of acidic amino acids in the linker between D1 and D2 called the "acid box" (AB). The region containing D1 and AB is believed to be involved in autoinhibition of the receptor, which is relieved by binding to ligand.

The FGFRs are characterized by multiple alternative splicing of their mRNAs, leading to a variety of isoforms (Ornitz et al., *J. Biol. Chem.* 271:15292, 1996; see also Swiss-Prot P21802 and isoforms P21802-1 to -20 for sequences of FGFR2 and its isoforms). Notably, there are forms containing all three Ig domains (a isoform) or only the two Ig domains D2 and D3 domains without D1 (β isoform). In FGFR1, FGFR2, and FGFR3, all forms contain the first half of D3 denoted Ma, but two alternative exons can be utilized for the second half of D3, leading to IIIb and IIIc forms. For FGFR2, these are respectively denoted FGFR2-IIIb and FGFR2-IIIc (or just FGFR2b and FGFR2c); the corresponding beta forms are denoted FGFR2(beta)IIIb and FGFR2(beta)IIIc. The FGFR2-IIIb form of FGFR2 (also denoted K-sam-II) is a high affinity receptor for both FGF1 and KGF family members (FGF7, FGF10, and FGF22) whereas FGFR2-IIIc (also denoted K-sam-I) binds both FGF1 and FGF2 well but does not bind the KGF family members (Miki et al., Proc. Natl. Acad. Sci. USA 89:246, 1992). Indeed, FGFR2-IIIb is the only receptor for KGF family members (Ornitz et al., 1996, op. cit.) and is therefore also designated KGFR.

The FGFRs and their isoforms are differentially expressed in various tissues. FGFR2-IIIb (and the IIIb forms of FGFR1 and FGFR3) is expressed in epithelial tissues, while FGFR2-IIIc is expressed in mesenchymal tissues (Duan et al., *J. Biol. Chem.* 267:16076, 1992; Ornitz et al., 1996, op. cit.). Certain of the FGF ligands of these receptors have an opposite pattern of expression. Thus, KGF subfamily members, including FGF7 (KGF), FGF10, and FGF22, bind only to FGFR2-IIIb (Zhang et al., op. cit.) and are expressed in mesenchymal tissues, and so may be paracrine effectors of epithelial cells (Ornitz et al., 1996, op. cit.). In contrast, the FGF4 subfamily members FGF4-6 bind to FGFR2-IIIc and are expressed in both epithelial and mesenchymal lineages, and so may have either autocrine or paracrine functions. Because of the expression patterns of the isoforms of FGFR2 and their ligands, FGFR2 plays a role in epithelial-mesynchymal interactions (Finch et al., *Dev. Dyn.* 203:223, 1995), so it is not surprising that knock-out of FGFR2-IIIb in mice leads to severe embryonic defects and lethality (De Moerlooze et al., *Development* 127:483, 2000).

KGF (FGF7) and KGFR (FGFR2-IIIb) are overexpressed in many pancreatic cancers (Ishiwata et al., *Am. J. Pathol.* 153: 213, 1998), and their coexpression correlates with poor prognosis (Cho et al., *Am. J. Pathol.* 170:1964, 2007). Somatic mutations of the FGFR2 gene were found in 12% of a large panel of endometrial (uterine) carcinomas, and in several tested cases were required for tumor cell survival (Dutt et al., *Proc. Natl. Acad. Sci. USA* 105:8713, 2008). In two tumors the FGFR2 mutation was found to be the same S252W substitution associated with Apert syndrome. Amplification and overexpression of FGFR2 is associated with the undifferentiated, diffuse type of gastric cancer, which has a particularly poor prognosis, and inhibition of the FGFR2 activity by small molecule compounds potently inhibited proliferation of such cancer cells (Kunii et al., *Cancer Res.* 68:2340, 2008; Nakamura et al., *Gastroenterol.* 131:1530, 2006).

Inhibition of FGFR signaling has been reported to improve anti-tumor immunity and impair metastasis in breast cancer. (See, e.g., T. Ye et al., *Breast Cancer Res. Treat.* 143: 435-446 (2014).) Anti-FGFR2 antibodies have also been tested in models of gastric cancer, for example. Particular anti-FGFR2 antibodies are described, for example, in U.S. Pat. No. 8,101,723 B2, including monoclonal antibodies that bind human FGFR2-IIIb but bind less well or do not bind to FGFR2-IIIc and vice versa. U.S. Patent Publication No. 2015-0050273 A1 describes certain afucosylated antibodies that bind to FGFR2-IIIb.

SUMMARY

The present disclosure includes, for example, methods of treating gastrointestinal cancer, such as gastric cancer, in a subject comprising administering to the subject a therapeutically effective amount of an anti-fibroblast growth factor receptor 2 (anti-FGFR2) and modified FOLFOX6 (mFOLFOX6) chemotherapy. In some embodiments, the anti-FGFR2 antibody is an anti-FGFR2-IIIb antibody. In some embodiments, the anti-FGFR2-IIIb antibody has one or more of the following properties: binds to FGFR2-IIIb with higher affinity than to FGFR2-IIIc or does not detectably bind to FGFR2-IIIc; inhibits binding of FGF2 to human FGFR2; inhibits binding of FGF7 to human FGFR2; inhibits growth of a human tumor in a mouse tumor model; induces an ADCC activity; possesses enhanced ADCC activity; is afucosylated; and is capable of increasing the number of one or more of PD-L1 positive cells, NK cells, CD3+ T cells, CD4+ T cells, CD8+ T cells, and macrophages in tumor tissue in a mouse tumor model compared to a control.

In some embodiments, the anti-FGFR2-IIIb antibody comprises heavy chain and light chain variable regions, wherein the heavy chain variable region comprises: a heavy chain hypervariable region H1 (HVR-H1) comprising the amino acid sequence of SEQ ID NO: 6; an HVR-H2 comprising the amino acid sequence of SEQ ID NO: 7; and an HVR-H3 comprising the amino acid sequence of SEQ ID NO: 8; and the light chain variable region comprises: a light chain hypervariable region L1 (HVR-L1) comprising the amino acid sequence of SEQ ID NO: 9; HVR-L2 comprising the amino acid sequence of SEQ ID NO: 10; and HVR-L3 comprising the amino acid sequence of SEQ ID NO: 11. In some embodiments, the heavy chain variable domain of the anti-FGFR2-IIIb antibody comprises an amino acid sequence at least 95% identical to the amino acid sequence of SEQ ID NO: 4. In some embodiments, the light chain variable domain of the anti-FGFR2-IIIb antibody comprises an amino acid sequence at least 95% identical to the amino acid sequence of SEQ ID NO: 5. In some embodiments, the heavy chain variable domain of the anti-FGFR2-IIIb antibody comprises the amino acid sequence of SEQ ID NO: 4. In some embodiments, the light chain variable domain of the anti-FGFR2-IIIb antibody comprises the amino acid sequence of SEQ ID NO: 5. In some embodiments, the heavy chain of the anti-FGFR2-IIIb antibody comprises an amino acid sequence at least 95% identical to the amino acid sequence of SEQ ID NO: 2. In some embodiments, the anti-FGFR2-IIIb antibody comprises an amino acid sequence at least 95% identical to the amino acid sequence of SEQ ID NO: 3. In some embodiments, the heavy chain of the anti-FGFR2-IIIb antibody comprises the amino acid sequence of SEQ ID NO: 2. In some embodiments, the light chain of the anti-FGFR2-IIIb antibody comprises the amino acid sequence of SEQ ID NO: 3. In some embodiments, the anti-FGFR2-IIIb antibody is chimeric, humanized, or human. In some embodiments, the anti-FGFR2-IIIb antibody is selected from a Fab, an Fv, an scFv, a Fab', and a (Fab')$_2$.

In some embodiments of the methods herein, the anti-FGFR2-IIIb antibody has one or more of the following properties: lacks a fucose at position Asn297; comprises a κ light chain constant region; comprises an IgG1 heavy chain constant region; has enhanced ADCC activity in vitro compared to an antibody having the same amino acid sequence that is fucosylated at position Asn297; has enhanced affinity for Fc gamma RIIIA compared to an antibody having the same amino acid sequence that is fucosylated at position Asn297; and is capable of increasing the number of one or more of PD-L1 positive cells, NK cells, CD3+ T cells, CD4+ T cells, CD8+ T cells, and macrophages in tumor tissue in a mouse tumor model compared to a control.

In some embodiments of the methods herein, the subject has a gastric cancer that is locally advanced, unresectable or metastatic. In some embodiments, the gastric cancer is gastroesophageal cancer.

In some embodiments of the methods herein, the anti-FGFR2-IIIb antibody is administered at a dose of 6-15 mg/kg, 10-15 mg/kg, 6 mg/kg, 7 mg/kg, 8 mg/kg, 9 mg/kg, 10 mg/kg, 11 mg/kg, 12 mg/kg, 13 mg/kg, 14 mg/kg, or 15 mg/kg. In some embodiments, the anti-FGFR2-IIIb antibody is administered once every 10-21 days, once every 10-15 days, once every 10 days, once every 11 days, once every 12 days, once every 13 days, once every 14 days, once every 15 days, once every 16 days, once every 17 days, once every 18 days, once every 19 days, once every 20 days, or once every 21 days. In some embodiments, the anti-FGFR2-IIIb antibody is administered at a dose of 6 mg/kg, 10 mg/kg or 15 mg/kg, wherein the anti-FGFR2-IIIb antibody is administered once every 14 days.

In some embodiments, the anti-FGFR2-IIIb antibody is administered in a dosage regime as follows: (a) at a dose of 6-15 mg/kg, wherein the anti-FGFR2-IIIb antibody is administered once every 14 days; (b) at a dose of 6 mg/kg, wherein the anti-FGFR2-IIIb antibody is administered once every 14 days; (c) at a dose of 10 mg/kg, wherein the anti-FGFR2-IIIb antibody is administered once every 14 days; or (d) at a dose of 15 mg/kg, wherein the anti-FGFR2-IIIb antibody is administered once every 14 days. In some embodiments (a) the anti-FGFR2-IIIb antibody is administered at a dose of 6-15 mg/kg, 10-15 mg/kg, 6 mg/kg, 7 mg/kg, 8 mg/kg, 9 mg/kg, 10 mg/kg, 11 mg/kg, 12 mg/kg, 13 mg/kg, 14 mg/kg, or 15 mg/kg once every 11-17 days, every 12-16 days, every 13-15 days, or every 14 days, and (b) at least one intervening dose of 3-8 mg/kg, 5-8 mg/kg, 7-8 mg/kg, 3 mg/kg, 4 mg/kg, 5 mg/kg, 6 mg/kg, 7 mg/kg, or 8 mg/kg is administered between two doses of (a), and wherein the dose of (b) is lower than the dose of (a). In some embodiments, (i) the dose of (a) is 10-15 mg/kg every 13-15 days; (ii) the dose of (a) is 15 mg/kg every 13-15 days; (iii) the dose of (b) is 5-8 mg/kg and is administered 6-8 days after at least one dose of (a) and 6-8 days before the subsequent dose of (a); (iv) the dose of (a) is 10-15 mg/kg every 13-15 days and the dose of (b) is 7-8 mg/kg and is administered 6-8 days after at least one dose of (a) and 6-8 days before the subsequent dose of (a); (v) the dose of (a) is 15 mg/kg every 14 days and the dose of (b) is 7-8 mg/kg and is administered 7 days after at least one dose of (a) and 7 days before the subsequent dose of (a); (vi) the dose of (a) is 15 mg/kg every 14 days and the dose of (b) is 7.5 mg/kg and is administered 7 days after at least one dose of (a) and 7 days before the subsequent dose of (a); and/or (vii) the dose of (b) is administered after the first administration of the dose of (a) in any of (i) through (vi). In some embodiments, the anti-FGFR2-IIIb antibody is administered at a dose of 15 mg/kg once every 14 days, while 6-8 days following the first administration of the anti-FGFR2-IIIb antibody, the anti-FGFR2-IIIb antibody is further administered at a dose of 7.5 mg/kg. In some such embodiments, the anti-FGFR2-IIIb antibody is administered at a dose of 15 mg/kg once every 14 days, while 7 days following the first administration of the anti-FGFR2-IIIb antibody, the anti-FGFR2-IIIb antibody is administered at a dose of 7.5 mg/kg. In some such embodiments, the 7.5 mg/kg dose is given only one time, i.e. between the first and second 15 mg/kg administrations.

In some embodiments of the methods herein, the mFOLFOX6 comprises administration of 85 mg/m$^2$ oxaliplatin, 400 mg/m$^2$ leucovorin, and 400 mg/m$^2$ 5-fluorouracil (5-FU) by intravenous (IV) infusion or IV bolus. In some embodiments, the mFOLFOX6 comprises administration of 85 mg/m$^2$ oxaliplatin, 400 mg/m$^2$ leucovorin, and 400 mg/m$^2$ 5-fluorouracil (5-FU) by intravenous (IV) infusion or IV bolus followed by administration of 2400 mg/m$^2$ 5-FU by IV infusion over 44-48 hours. In some embodiments, the mFOLFOX6 is administered once every 10-21 days, once every 10-15 days, once every 10 days, once every 11 days, once every 12 days, once every 13 days, once every 14 days, once every 15 days, once every 16 days, once every 17 days, once every 18 days, once every 19 days, once every 20 days, or once every 21 days. In some embodiments, the mFOLFOX6 is administered once every 14 days. In some embodiments, the mFOLFOX6 comprises administration of 85 mg/m² oxaliplatin, 400 mg/m² leucovorin, and 400 mg/m² 5-fluorouracil (5-FU) by intravenous (IV) infusion or IV bolus followed by administration of 2400 mg/m² 5-FU by IV infusion over 44-48 hours, wherein the mFOLFOX6 is administered once every 14 days.

In some embodiments of the methods herein, the anti-FGFR2-IIIb antibody and the mFOLFOX6 are administered concurrently or sequentially. In some embodiments, one or more administrations of the mFOLFOX6 are given prior to administering the anti-FGFR2-IIIb antibody. In some embodiments, two administrations of the mFOLFOX6 are given prior to administering the anti-FGFR2-IIIb antibody. In some embodiments, the anti-FGFR2-IIIB antibody is administered on the same day as the mFOLFOX6 and prior to mFOLFOX6 administration.

In some embodiments, the gastric cancer has previously been determined to overexpress FGFR2-IIIb and/or the gastric cancer has previously been determined to have an FGFR2 gene amplification. In some embodiments, the method further comprises determining whether the gastric cancer overexpresses FGFR2-IIIb and/or determining whether the gastric cancer has an FGFR2 gene amplification. In some embodiments, FGFR2-IIIb overexpression is determined at the protein level by immunohistochemistry (IHC). In some embodiments, the overexpression was previously determined or is determined by an IHC signal of 3+ in at least 10%, 20%, 30%, 40%, or 50% of tumor cells. In some embodiments, FGFR2 gene amplification was previously determined or is determined by obtaining the ratio of FGFR2 to chromosome 10 centromere (CEN10) using fluorescence in situ hybridization (FISH), wherein the FGFR2 gene is considered amplified if the FGFR2/CEN10 ratio determined by FISH is greater than or equal to 2. In some embodiments, the FGFR2 amplification was previously detected or is detected in circulating tumor DNA (ctDNA).

Some embodiments of the present disclosure encompass methods of treating locally advanced, unresectable or metastatic gastric cancer in a subject comprising administering to the subject a therapeutically effective amount of an anti-fibroblast growth factor receptor 2 IIIb (anti-FGFR2-IIIb) antibody and modified FOLFOX6 (mFOLFOX6) chemotherapy, wherein the anti-FGFR2-IIIb antibody comprises heavy chain and light chain variable regions, wherein the heavy chain variable region comprises:
(i) HVR-H1 comprising the amino acid sequence of SEQ ID NO: 6;
(ii) HVR-H2 comprising the amino acid sequence of SEQ ID NO: 7; and
(iii) HVR-H3 comprising the amino acid sequence of SEQ ID NO: 8;
and the light chain variable region comprises:
(iv) HVR-L1 comprising the amino acid sequence of SEQ ID NO: 9;
(v) HVR-L2 comprising the amino acid sequence of SEQ ID NO: 10; and
(vi) HVR-L3 comprising the amino acid sequence of SEQ ID NO: 11;
wherein the anti-FGFR2-IIIb antibody is administered intravenously at a dose of 10-15 mg/kg followed by administration of the mFOLFOX6 comprising administration of 85 mg/m² oxaliplatin, 400 mg/m² leucovorin, and 400 mg/m² 5-fluorouracil (5-FU) by IV infusion or IV bolus followed by administration of 2400 mg/m² 5-FU by IV infusion over 44-48 hours; and wherein the anti-FGFR2-IIIb and mFOLFOX6 are administered every 2 weeks. Some embodiments of the present disclosure encompass methods of treating locally advanced, unresectable or metastatic gastric cancer in a subject comprising administering to the subject a therapeutically effective amount of an anti-fibroblast growth factor receptor 2 IIIb (anti-FGFR2-IIIb) antibody and modified FOLFOX6 (mFOLFOX6) chemotherapy, wherein the anti-FGFR2-IIIb antibody comprises heavy chain and light chain variable regions, wherein the heavy chain variable region comprises:
(i) HVR-H1 comprising the amino acid sequence of SEQ ID NO: 6;
(ii) HVR-H2 comprising the amino acid sequence of SEQ ID NO: 7; and
(iii) HVR-H3 comprising the amino acid sequence of SEQ ID NO: 8;
and the light chain variable region comprises:
(iv) HVR-L1 comprising the amino acid sequence of SEQ ID NO: 9;
(v) HVR-L2 comprising the amino acid sequence of SEQ ID NO: 10; and
(vi) HVR-L3 comprising the amino acid sequence of SEQ ID NO: 11;
wherein the anti-FGFR2-IIIb antibody and mFOLFOX6 are administered every 13-15 days, and optionally wherein a single dose of 3-8 mg/kg anti-FGFR2-IIIb antibody is administered 6-8 days after the first dose of 6-15 mg/kg anti-FGFR2-IIIb antibody and before the second dose of 6-15 mg/kg anti-FGFR2-IIIb antibody. In some such embodiments, (a) the anti-FGFR2-IIIb antibody is administered intravenously at a dose of 15 mg/kg, (b) the anti-FGFR2-IIIb antibody and mFOLFOX6 are administered every 14 days on the same day, and (c) a single dose of 7.5 mg/kg anti-FGFR2-IIIb antibody is administered 7 days after the first dose of 15 mg/kg anti-FGFR2-IIIb antibody and before the second dose of 15 mg/kg anti-FGFR2-IIIb antibody.

In some embodiments herein, the gastric cancer has previously been determined to overexpress FGFR2-IIIb as indicated by an IHC signal of 3+ in at least 10% of tumor cells and/or the gastric cancer has previously been determined to have an FGFR2 gene amplification in ctDNA. In some such embodiments, the subject received two administrations of mFOLFOX6 prior to the first administration of the anti-FGFR2-IIIb antibody.

The present disclosure also encompasses compositions comprising an anti-FGFR2-IIIb antibody as described herein and each of oxaliplatin, leucovorin, and 5-FU, for example, for use in treating gastrointestinal cancer, such as gastric cancer, in a patient according to any of the above methods. In some embodiments, the compositions comprise a combination of an anti-FGFR2-IIIb antibody as described herein and at least one of oxaliplatin, leucovorin, and 5-FU. In some embodiments, the anti-FGFR2-IIIb antibody and the at least one of oxaliplatin, leucovorin, and 5-FU are in separate containers or compartments. In some such embodiments, the compositions comprise a combination of the antibody and each of oxaliplatin, leucovorin, and 5-FU in separate containers or compartments. In some embodiments, the compositions further comprise instructions for use in gastrointestinal cancer, e.g. gastric cancer, treatment.

In some embodiments of the methods or compositions herein, the anti-FGFR2-IIIb antibody has the heavy and light chain hypervariable region (HVR) H1, H2, H3, L1, L2, and L3 amino acid sequences of monoclonal antibodies GAL-FR21, GAL-FR22, or GAL-FR23, described in U.S. Pat. No. 8,101,723 B2. In some embodiments the anti-FGFR2-IIIb antibody heavy chain variable region comprises: (i) HVR-H1 comprising the amino acid sequence of SEQ ID NO: 6; (ii) HVR-H2 comprising the amino acid sequence of SEQ ID NO: 7; and (iii) HVR-H3 comprising the amino acid sequence of SEQ ID NO: 8; and the light chain variable region comprises: (iv) HVR-L1 comprising the amino acid sequence of SEQ ID NO: 9; (v) HVR-L2 comprising the amino acid sequence of SEQ ID NO: 10; and (vi) HVR-L3 comprising the amino acid sequence of SEQ ID NO: 11.

In some embodiments, the anti-FGFR2-IIIb antibody has a heavy chain variable domain that is at least 95%, such as at least 97%, at least 98%, or at least 99% identical to the amino acid sequence of SEQ ID NO:4, or that comprises the amino acid sequence of SEQ ID NO: 4. In some embodiments, the anti-FGFR2-IIIb antibody has a light chain variable domain that is at least 95%, such as at least 97%, at least 98%, or at least 99% identical to the amino acid sequence of SEQ ID NO:5, or that comprises the amino acid sequence of SEQ ID NO: 5. In some embodiments, the heavy chain variable domain is at least 95%, such as at least 97%, at least 98%, or at least 99% identical to the amino acid sequence of SEQ ID NO:4, or that comprises the amino acid sequence of SEQ ID NO: 4 and the light chain variable domain is at least 95%, such as at least 97%, at least 98%, or at least 99% identical to the amino acid sequence of SEQ ID NO:5, or that comprises the amino acid sequence of SEQ ID NO: 5. In some embodiments, the anti-FGFR2-IIIb antibody has a heavy chain that is at least 95%, such as at least 97%, at least 98%, or at least 99% identical to the amino acid sequence of SEQ ID NO: 2, or that comprises the amino acid sequence of SEQ ID NO: 2. In some embodiments, the anti-FGFR2-IIIb antibody has a light chain that is at least 95%, such as at least 97%, at least 98%, or at least 99% identical to the amino acid sequence of SEQ ID NO:3, or that comprises the amino acid sequence of SEQ ID NO: 3. In some embodiments, the heavy chain is at least 95%, such as at least 97%, at least 98%, or at least 99% identical to the amino acid sequence of SEQ ID NO:2, or that comprises the amino acid sequence of SEQ ID NO: 2 and the light chain is at least 95%, such as at least 97%, at least 98%, or at least 99% identical to the amino acid sequence of SEQ ID NO:3, or that comprises the amino acid sequence of SEQ ID NO: 3.

In some embodiments the anti-FGFR2-IIIb antibody heavy chain variable region comprises: (i) CDR1 comprising the amino acid sequence of SEQ ID NO: 16; (ii) CDR2 comprising the amino acid sequence of SEQ ID NO: 17; and (iii) CDR3 comprising the amino acid sequence of SEQ ID NO: 18; and the light chain variable region comprises: (iv) CDR1 comprising the amino acid sequence of SEQ ID NO: 20; (v) CDR2 comprising the amino acid sequence of SEQ ID NO: 21; and (vi) CDR3 comprising the amino acid sequence of SEQ ID NO: 22.

In some embodiments, the anti-FGFR2-IIIb antibody has a heavy chain variable domain that is at least 95%, such as at least 97%, at least 98%, or at least 99% identical to the amino acid sequence of SEQ ID NO:15, or that comprises the amino acid sequence of SEQ ID NO: 15. In some embodiments, the anti-FGFR2-IIIb antibody has a light chain variable domain that is at least 95%, such as at least 97%, at least 98%, or at least 99% identical to the amino acid sequence of SEQ ID NO:19, or that comprises the amino acid sequence of SEQ ID NO: 19. In some embodiments, the heavy chain variable domain is at least 95%, such as at least 97%, at least 98%, or at least 99% identical to the amino acid sequence of SEQ ID NO:15, or that comprises the amino acid sequence of SEQ ID NO: 15 and the light chain variable domain is at least 95%, such as at least 97%, at least 98%, or at least 99% identical to the amino acid sequence of SEQ ID NO:19, or that comprises the amino acid sequence of SEQ ID NO: 19.

In some embodiments the anti-FGFR2-IIIb antibody is afucosylated. In some embodiments, the antibody lacks fucose at Asn297. In some embodiments, the anti-FGFR2-IIIb antibody comprises a kappa light chain constant region. In some embodiments, the antibody comprises an IgG1 heavy chain constant region. In some embodiments, an afucosylated antibody has enhanced ADCC (antibody-dependent cell cytotoxic) activity in vitro and/or in vivo compared to an antibody having the same amino acid sequence that is fucosylated at Asn297. In some embodiments, an afucosylated antibody has enhanced affinity for Fc gamma RIIIA compared to an antibody having the same amino acid sequence that is fucosylated at position Asn297. In some embodiments, the afucosylated antibody is capable of increasing the number of one or more of PD-L1 positive cells, NK cells, CD3+ T cells, CD4+ T cells, CD8+ T cells, and macrophages in tumor tissue in a mouse xenograft and/or syngeneic tumor model compared to a control (e.g. as compared to a control antibody that does not target FGFR2).

It is to be understood that both the foregoing general description and the following detailed description are exemplary and explanatory only and are not restrictive of the claims. The section headings used herein are for organizational purposes only and are not to be construed as limiting the subject matter described. All references cited herein, including patent applications and publications, are incorporated herein by reference in their entireties for any purpose.

BRIEF DESCRIPTION OF THE DRAWINGS

FIG. 1 shows administration schedules for the dose escalation part I of the clinical trial described below in Example 1. The initial cohort is at dose level 1, and further enrollments will be at dose levels 1, 2, or −1 as shown in the figure according to analysis of the presence of dose-limiting toxicities (DLTs) as provided below in Table 2.

DESCRIPTION OF PARTICULAR EMBODIMENTS

Definitions

Figure 2:
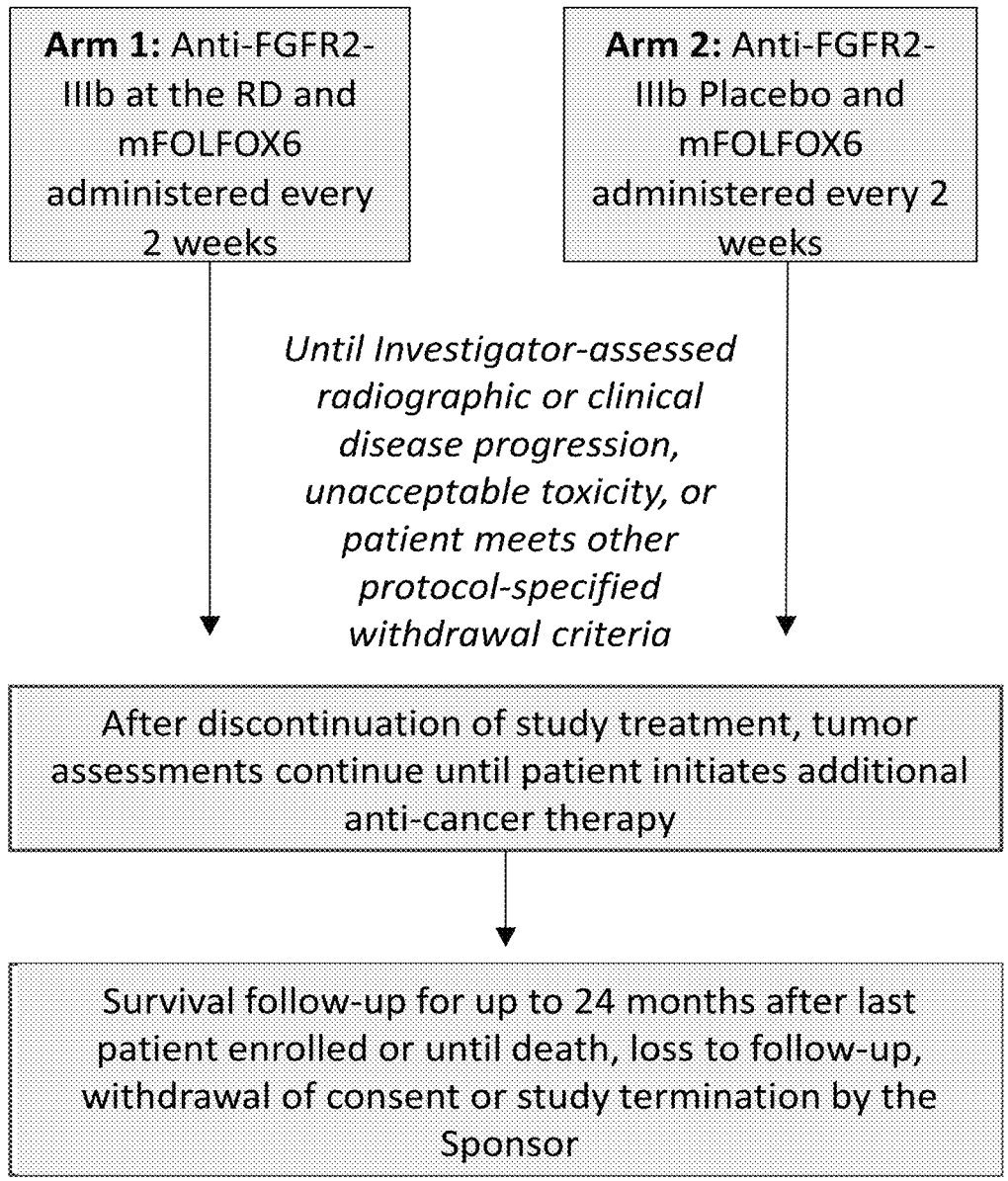
FIG. 2 provides a flow-chart showing patient assessments to be performed for part I of the clinical trial described below in Example 1.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Exemplary techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* (2nd ed., Cold Spring Harbor Laboratory Press, Cold Spring Harbor, N.Y. (1989)), among other places. In addition, exemplary techniques for chemical syntheses, chemical analyses, pharmaceutical preparation, formulation, and delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein that includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts that produce the proteins or errors due to PCR amplification.

"FGFR2" refers to human fibroblast growth factor receptor 2 including any of its alternatively spliced forms such as the IIIa, IIIb and IIIc splice forms. The term FGFR2 encompasses wild-type FGFR2 and naturally occurring mutant forms such as FGFR2 activating mutant forms such as FGFR2-S252W, which is found in some cancer cells. "FGFR2-IIIb" or "FGFR2b" are used interchangeably to refer to the human fibroblast growth factor receptor 2 IIIb splice form. An exemplary human FGFR2-IIIb sequence is shown in GenBank Accession No. NP_075259.4, dated Jul. 7, 2013. A nonlimiting exemplary mature human FGFR2-IIIb amino acid sequence is shown in SEQ ID NO: 1. "FGFR2-IIIc" or "FGFR2c" are used interchangeably to refer to the human fibroblast growth factor receptor 2 IIIc splice form. An exemplary human FGFR2-IIIc sequence is shown in GenBank Accession No. NP_000132.3, dated Jul. 7, 2013. A nonlimiting exemplary mature FGFR2-IIIc amino acid sequence is shown in SEQ ID NO: 12.

An "FGFR2 extracellular domain" or "FGFR2 ECD" refers to an extracellular domain of human FGFR2, including natural and engineered variants thereof. An example of an FGFR2 ECD is provided in SEQ ID NOs: 13.

The term "antibody" as used herein refers to a molecule comprising at least hypervariable regions (HVRs) H1, H2, and H3 of a heavy chain and L1, L2, and L3 of a light chain, wherein the molecule is capable of binding to antigen. The term antibody includes, but is not limited to, fragments that are capable of binding antigen, such as Fv, single-chain Fv (scFv), Fab, Fab', and (Fab')$_2$. The term antibody also includes, but is not limited to, chimeric antibodies, humanized antibodies, human antibodies, and antibodies of various species such as mouse, human, cynomolgus monkey, etc. It also includes antibodies conjugated to other molecules such as small molecule drugs, bispecific antibodies and multispecific antibodies.

An "anti-FGFR2" antibody refers to an antibody that specifically binds to FGFR2. An "anti-FGFR2-IIIb" antibody or "anti-FGFR2b" antibody refers to an antibody that specifically binds to FGFR2-IIIb (aka. FGFR2b). Such an antibody has a higher affinity for FGFR2-IIIb than for other isoforms of FGFR2, such as FGFR2-IIIc. In some embodiments, the antibody may not detectably bind to FGFR2-IIIc. The terms "anti-FGFR2 antibody," "anti-FGFR2-IIIb antibody" and "anti-FGFR2b antibody" specifically include afucosylated forms of such antibodies.

The term "heavy chain variable region" refers to a region comprising heavy chain HVR1, framework (FR) 2, HVR2, FR3, and HVR3. In some embodiments, a heavy chain variable region also comprises at least a portion of an FR1 and/or at least a portion of an FR4.

The term "heavy chain constant region" refers to a region comprising at least three heavy chain constant domains, $C_H1$, $C_H2$, and $C_H3$. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

The term "heavy chain" refers to a polypeptide comprising at least a heavy chain variable region, with or without a leader sequence. In some embodiments, a heavy chain comprises at least a portion of a heavy chain constant region. The term "full-length heavy chain" refers to a polypeptide comprising a heavy chain variable region and a heavy chain constant region, with or without a leader sequence.

The term "light chain variable region" refers to a region comprising light chain HVR1, framework (FR) 2, HVR2, FR3, and HVR3. In some embodiments, a light chain variable region also comprises an FR1 and/or an FR4.

The term "light chain constant region" refers to a region comprising a light chain constant domain, $C_L$. Nonlimiting exemplary light chain constant regions include λ and κ.

The term "light chain" refers to a polypeptide comprising at least a light chain variable region, with or without a leader sequence. In some embodiments, a light chain comprises at least a portion of a light chain constant region. The term "full-length light chain" refers to a polypeptide comprising a light chain variable region and a light chain constant region, with or without a leader sequence.

The term "hypervariable region" or "HVR" refers to each of the regions of an antibody variable domain that are hypervariable in sequence and/or form structurally defined loops ("hypervariable loops"). Generally, native four-chain antibodies comprise six HVRs; three in the $V_H$ (H1, H2, H3), and three in the $V_L$ (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, MD (1991)). The terms hypervariable regions (HVRs) and complementarity determining regions (CDRs) both refer to portions of the variable region that form the antigen binding regions.

"Affinity" or "binding affinity" refers to the strength of the sum total of noncovalent interactions between a single binding site of a molecule (e.g., an antibody) and its binding partner (e.g., an antigen). In some embodiments, "binding affinity" refers to intrinsic binding affinity, which reflects a 1:1 interaction between members of a binding pair (e.g., antibody and antigen). The affinity of a molecule X for its partner Y can generally be represented by the dissociation constant ($K_d$).

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *Proc. Natl. Acad. Sci.* (USA) 95:652-656 (1998). Additional antibodies with altered Fc region amino acid sequences and increased or decreased ADCC activity are described, e.g., in U.S. Pat. Nos. 7,923,538, and 7,994,290.

An antibody having an "enhanced ADCC activity" refers to an antibody that is more effective at mediating ADCC in vitro or in vivo compared to the parent antibody, wherein the antibody and the parent antibody differ in at least one structural aspect, and when the amounts of such antibody and parent antibody used in the assay are essentially the same. In some embodiments, the antibody and the parent antibody have the same amino acid sequence, but the antibody is afucosylated while the parent antibody is fucosylated. In some embodiments, ADCC activity will be determined using the in vitro ADCC assay such as disclosed in US Publication No. 2015-0050273-A1, but other assays or methods for determining ADCC activity, e.g. in an animal model etc., are contemplated. In some embodiments, an antibody with enhanced ADCC activity also has enhanced affinity for Fc gamma RIIIA In some embodiments, an antibody with enhanced ADCC activity has enhanced affinity for Fc gamma RIIIA (V158). In some embodiments, an antibody with enhanced ADCC activity has enhanced affinity for Fc gamma RIIIA (F158).

"Enhanced affinity for Fc gamma RIIIA" refers to an antibody that has greater affinity for Fc gamma RIIIA (also referred to, in some instances, as CD16a) than a parent antibody, wherein the antibody and the parent antibody differ in at least one structural aspect. In some embodiments, the antibody and the parent antibody have the same amino acid sequence, but the antibody is afucosylated while the parent antibody is fucosylated. Any suitable method for determining affinity for Fc gamma RIIIA may be used. In some embodiments, affinity for Fc gamma RIIIA is determined by a method described in U.S. Publication No. 2015-0050273-A1. In some embodiments, an antibody with enhanced affinity for Fc gamma RIIIA also has enhanced ADCC activity. In some embodiments, an antibody with enhanced affinity for Fc gamma RIIIA has enhanced affinity for Fc gamma RIIIA (V158). In some embodiments, an antibody with enhanced affinity for Fc gamma RIIIA has enhanced affinity for Fc gamma RIIIA (F158).

A "chimeric antibody" as used herein refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, a chimeric antibody comprises at least one rat variable region and at least one mouse constant region. In some embodiments, all of the variable regions of a chimeric antibody are from a first species and all of the constant regions of the chimeric antibody are from a second species.

A "humanized antibody" as used herein refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is a Fab, an scFv, a (Fab')$_2$, etc.

A "human antibody" as used herein refers to antibodies produced in humans, antibodies produced in non-human animals that comprise human immunoglobulin genes, such as XenoMouse®, and antibodies selected using in vitro methods, such as phage display, wherein the antibody repertoire is based on a human immunoglobulin sequences.

An "afucosylated" antibody or an antibody "lacking fucose" refers to an IgG1 or IgG3 isotype antibody that lacks fucose in its constant region glycosylation. Glycosylation of human IgG1 or IgG3 occurs at Asn297 (N297) as core fucosylated biantennary complex oligosaccharide glycosylation terminated with up to 2 Gal residues. In some embodiments, an afucosylated antibody lacks fucose at Asn297. These structures are designated as G0, G1 (α1,6 or α1,3) or G2 glycan residues, depending on the amount of terminal Gal residues. See, e.g., Raju, T. S., *BioProcess Int.* 1: 44-53 (2003). CHO type glycosylation of antibody Fc is described, e.g., in Routier, F. H., *Glycoconjugate J.* 14: 201-207 (1997). Within a population of antibodies, the antibodies are considered to be afucosylated if <5% of the antibodies of the population comprise fucose at Asn297.

"Effector functions" refer to biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

With reference to anti-FGFR2 antibodies, the terms "blocks binding o" or "inhibits binding o" a ligand refer to the ability to inhibit an interaction between FGFR2 and an FGFR2 ligand, such as human fibroblast growth factor 1 (FGF1) or FGF2. Such inhibition may occur through any mechanism, including direct interference with ligand binding, e.g., because of overlapping binding sites on FGFR2, and/or conformational changes in FGFR2 induced by an antibody that alter ligand affinity, or, e.g., in the case of an FGFR2 ECD or FGFR2 ECD fusion molecule, by competing for binding to FGFR2 ligands.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The term "elevated level" means a higher level of a protein in a particular tissue of a subject relative to the same tissue in a control, such as an individual or individuals who are not suffering from cancer or other condition described herein. The elevated level may be the result of any mechanism, such as increased expression, increased stability, decreased degradation, increased secretion, decreased clearance, etc., of the protein.

The terms "reduce" or "reduces" or "increase" or "increases" with respect to a protein or cell type means to change the level of that protein or cell type in a particular tissue of a subject, such as in a tumor, by at least 10%. In some embodiments, an agent, such as an anti-FGFR2 antibody, increases or reduces the level of a protein or a cell type in a particular tissue of a subject, such as a tumor, by at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% relative to the level prior to contact with the antibody.

The terms "subject" and "patient" are used interchangeably herein to refer to a human. In some embodiments, methods of treating other mammals, including, but not limited to, rodents, simians, felines, canines, equines, bovines, porcines, ovines, caprines, mammalian laboratory animals, mammalian farm animals, mammalian sport animals, and mammalian pets, are also provided.

The term "sample," as used herein, refers to a composition that is obtained or derived from a subject that contains a cellular and/or other molecular entity that is to be characterized, quantitated, and/or identified, for example based on physical, biochemical, chemical and/or physiological characteristics. An exemplary sample is a tissue sample.

The term "cancer" refers to a malignant proliferative disorder associated with uncontrolled cell proliferation, unrestrained cell growth, and decreased cell death via apoptosis. The term "gastrointestinal cancer" or "GI cancer" refers to a cancer of the gastrointestinal tract such as gastric cancer, colorectal cancer, or pancreatic adenocarcinoma. In some embodiments, the gastrointestinal cancer is "gastric cancer" or "GC," which, as used herein, includes gastroesophageal cancer.

In some embodiments, a cancer comprises an FGFR2 gene amplification, whereas in some embodiments the cancer does not comprise an FGFR2 amplification. In some embodiments, where an amplification occurs, the FGFR2 amplification comprises an FGFR2:CEN10 (chromosome 10 centromere) ratio of >3. In some embodiments, FGFR2 amplification comprises an FGFR2:CEN10 ratio of ≥2. In other embodiments, however, the FGFR2 level comprises an FGFR2:CEN10 ratio of between 1 and 2, indicating that FGFR2 is not amplified. In some embodiments, mutations or translocations may cause an FGFR2 gene amplification.

FGFR2 gene amplification may be determined using a fluorescence in situ hybridization assay (FISH), for example. FGFR2 gene amplification may also be detected by a blood-based assay, or "liquid biopsy." In some embodiments of a blood-based assay, FGFR2 gene amplification may be detected in DNA from circulating tumor cells, or "CTCs." Methods for detection and molecular characterization of CTCs are described, e.g., in Alix-Panabieres (2013) *Clinical Chemistry* 59:1 110-118. In some embodiments of a blood based assay, FGFR2 gene amplification is detected in ctDNA. The term "ctDNA" refers to "circulating tumor DNA," which is tumor-derived fragmented DNA in the bloodstream that is not associated with cells. Methods for detection and molecular characterization of ctDNA are described, e.g., in Han et al. (2017) *Genomics, Proteomics & Bioinformatics* 15:2 59-72, and include PCR-based methods and next-generation sequencing (NGS).

In some embodiments, the cancer overexpresses FGFR2-IIIb. In some embodiments, the cancer overexpresses FGFR2-IIIb to a greater extent than FGFR2-IIIc. In some embodiments, the cancer expresses FGFR2-IIIb at a normalized level that is more than 2-fold, 3-fold, 5-fold, or 10-fold greater than the normalized level of FGFR2-IIIc expression. In some embodiments, a cancer overexpresses FGFR2-IIIb but does not comprise a FGFR2 gene amplification, while in other embodiments, the cancer comprises an FGFR2 gene amplification and also overexpresses FGFR2-IIIb. Expression of FGFR2-IIIb may be determined at the protein level by immunohistochemistry (IHC), for example, of tumor samples from a patient with comparison to normal tissue. The terms "FGFR2-IIIb protein overexpression" and "FGFR2-IIIb overexpression" and the like mean elevated levels of FGFR2-IIIb protein, regardless of the cause of such elevated levels (i.e., whether the elevated levels are a result of increased translation and/or decreased degradation of protein, other mechanism, or a combination of mechanisms). In some embodiments, FGFR2-IIIb overexpression may be detected at the mRNA level using, for example, techniques such as reverse-transcriptase polymerase chain reaction (RT-PCR) analysis compared to noncancerous tissue.

The level of FGFR2 or FGFR2-IIIb expression by IHC may be determined by giving a tumor sample an IHC score on a scale of 0-3. Herein, a score of "0" is given if no reactivity is observed or if there is membranous reactivity only in <10% of tumor cells; a score of "1+" is given if there is faint or barely perceptible membranous reactivity in at least 10% of tumor cells or if the cells are reactive only in a part of their membranes; a score of "2+" is given if there is weak to moderate complete, basolateral or lateral membranous reactivity in at least 10% of tumor cells; and a score of "3+" is given if there is strong complete basolateral or lateral membranous reactivity in at least 10% of tumor cells. In some embodiments, 1+, 2+, or 3+ staining of tumor cells by IHC indicates FGFR2-IIIb overexpression. In some embodiments, 2+ or 3+ staining of tumor cells by IHC indicates FGFR2-IIIb overexpression. In some embodiments, 3+ staining of tumor cells by IHC indicates FGFR2-IIIb overexpression.

A "modified FOLFOX6" or "mFOLFOX6" chemotherapy regimen refers to a regimen in which a combination of oxaliplatin (e.g. Eloxatin®), leucovorin (e.g. leucovorin calcium or folinic acid), and 5-fluorouracil (5-FU) are each administered to a human patient by IV infusion or IV bolus over the course of about 2-8 hours and in which a further infusion of 5-FU is then administered by IV infusion over an about 2 day period, as provided in various embodiments described herein.

"Treatment," as used herein, refers to therapeutic treatment, for example, wherein the object is to reduce in severity or slow progression of the targeted pathologic condition or disorder as well as, for example, wherein the object is to inhibit recurrence of the condition or disorder. In certain embodiments, the term "treatment" covers any administration or application of a therapeutic for disease in a patient, and includes inhibiting or slowing the disease or progression of the disease; partially or fully relieving the disease, for example, by causing regression, or restoring or repairing a lost, missing, or defective function; stimulating an inefficient process; or causing the disease plateau to have reduced severity. The term "treatment" also includes reducing the severity of any phenotypic characteristic and/or reducing the incidence, degree, or likelihood of that characteristic. Those in need of treatment include those already with the disorder as well as those at risk of recurrence of the disorder or those in whom a recurrence of the disorder is to be prevented or slowed down.

The term "effective amount" or "therapeutically effective amount" refers to an amount of a drug effective to treat a disease or disorder in a subject. In certain embodiments, an effective amount refers to an amount effective, at dosages and for periods of time necessary, to achieve the desired therapeutic or prophylactic result. A therapeutically effective amount of an anti-FGFR2 antibody and chemotherapy regimen of the invention may vary according to factors such as the disease state, age, sex, and weight of the individual, and the ability of the antibody or antibodies to elicit a desired response in the individual. A therapeutically effective amount encompasses an amount in which any toxic or detrimental effects of the antibody or antibodies are outweighed by the therapeutically beneficial effects. In some embodiments, the expression "effective amount" refers to an amount of the antibody that is effective for treating the cancer.

Administration "in combination with" one or more further therapeutic agents, such as a chemotherapy regimen, includes simultaneous (concurrent) and consecutive (sequential) administration in any order.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

Additional definitions may be provided in the sections that follow.

Exemplary Anti-FGFR2 Antibodies

Exemplary anti-FGFR2 antibodies include antibodies that specifically bind FGFR2-IIIb, i.e., anti-FGFR2-IIIb antibodies. In some embodiments, the anti-FGFR2-IIIb antibodies bind FGFR2-IIIc with lower affinity than they bind to FGFR2-IIIb. In some embodiments, the anti-FGFR2-IIIb antibodies do not detectably bind to FGFR2-IIIc.

An exemplary anti-FGFR2-IIIb antibody for use in the embodiments herein is the HuGAL-FR21 antibody described in U.S. Pat. No. 8,101,723 B2, issued Jan. 24, 2012, which is specifically incorporated herein by reference. FIGS. 13 and 14 of U.S. Pat. No. 8,101,723 B2 show the amino acid sequences of the variable regions and full-length mature antibody chains of HuGAL-FR21, and are incorporated by reference herein. The heavy chain variable region sequences of antibody HuGAL-FR21, are underlined in FIG. 13 of U.S. Pat. No. 8,101,723 B2, and are specifically incorporated by reference herein. In some embodiments, the antibody is afucosylated. In some embodiments, the antibody is an IgG1 or IgG3 antibody that lacks fucose at Asn297. Additional antibodies that may be used in the embodiments herein include those described in US Patent Publication No. 2015-0050273-A1, which describes certain afucosylated anti-FGFR2-IIIb antibodies, and which is incorporated by reference herein.

In some embodiments, the anti-FGFR2-IIIb antibody comprises at least one, two, three, four, five, or six hypervariable regions (HVRs; e.g., CDRs) selected from (a) HVR-H1 comprising the amino acid sequence of SEQ ID NO: 6; (b) HVR-H2 comprising the amino acid sequence of SEQ ID NO: 7; (c) HVR-H3 comprising the amino acid sequence of SEQ ID NO: 8; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11. In some embodiments, the antibody is afucosylated. In some embodiments, the antibody is an IgG1 or IgG3 antibody that lacks fucose at Asn297.

In some embodiments, the anti-FGFR2-IIIb antibody comprises a heavy chain variable region and a light chain variable region. In some embodiments, the anti-FGFR2-IIIb antibody comprises at least one heavy chain comprising a heavy chain variable region and at least a portion of a heavy chain constant region, and at least one light chain comprising a light chain variable region and at least a portion of a light chain constant region. In some embodiments, the anti-FGFR2-IIIb antibody comprises two heavy chains, wherein each heavy chain comprises a heavy chain variable region and at least a portion of a heavy chain constant region, and two light chains, wherein each light chain comprises a light chain variable region and at least a portion of a light chain constant region. In some embodiments, the anti-FGFR2-IIIb antibody comprises a heavy chain variable region comprising the amino acid sequence of SEQ ID NO: 4 and a light chain variable region comprising the amino acid sequence of SEQ ID NO: 5. In some embodiments, the anti-FGFR2-IIIb antibody comprises a heavy chain comprising the amino acid sequence of SEQ ID NO: 2 and a light chain comprising the amino acid sequence of SEQ ID NO: 3. In some embodiments, the antibody is afucosylated. In some embodiments, the antibody is an IgG1 or IgG3 antibody that lacks fucose at Asn297.

In some embodiments, the anti-FGFR2-IIIb antibody comprises six HVRs comprising (a) HVR-H1 comprising the amino acid sequence of SEQ ID NO: 6; (b) HVR-H2 comprising the amino acid sequence of SEQ ID NO: 7; (c) HVR-H3 comprising the amino acid sequence of SEQ ID NO: 8; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11. In some embodiments, the anti-FGFR2-IIIb antibody comprises the six HVRs as described above and binds to FGFR2-IIIb. In some embodiments, the anti-FGFR-IIIb antibody does not bind to FGFR2-IIIc. In some embodiments, the antibody is afucosylated. In some embodiments, the antibody is an IgG1 or IgG3 antibody that lacks fucose at Asn297.

In one aspect, the anti-FGFR2-IIIb antibody competes with an anti-FGFR2-IIIb antibody comprising six HVRs comprising (a) HVR-H1 comprising the amino acid sequence of SEQ ID NO: 6; (b) HVR-H2 comprising the amino acid sequence of SEQ ID NO: 7; (c) HVR-H3 comprising the amino acid sequence of SEQ ID NO: 8; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11. In some embodiments, the antibody is afucosylated. In some embodiments, the antibody is an IgG1 or IgG3 antibody that lacks fucose at Asn297.

In some embodiments, the anti-FGFR2-IIIb antibody comprises at least one, at least two, or all three VH HVR sequences selected from (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8. In some embodiments, the antibody is afucosylated. In some embodiments, the antibody is an IgG1 or IgG3 antibody that lacks fucose at Asn297.

In some embodiments, the anti-FGFR2-IIIb antibody comprising at least one, at least two, or all three VL HVR sequences selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11. In some embodiments, the antibody is afucosylated. In some embodiments, the antibody is an IgG1 or IgG3 antibody that lacks fucose at Asn297.

In some embodiments, the anti-FGFR2-IIIb antibody comprises (a) a VH domain comprising at least one, at least two, or all three VH HVR sequences selected from (i) HVR-H1 comprising the amino acid sequence of SEQ ID NO: 6, (ii) HVR-H2 comprising the amino acid sequence of SEQ ID NO: 7, and (iii) HVR-H3 comprising an amino acid sequence selected from SEQ ID NO: 8; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 11. In some embodiments, the antibody is afucosylated. In some embodiments, the antibody is an IgG1 or IgG3 antibody that lacks fucose at Asn297.

In some embodiments, the anti-FGFR2-IIIb antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 4. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR2-IIIb antibody comprising that sequence retains the ability to bind to FGFR2-IIIb. In certain embodiments, such an anti-FGFR2-IIIb antibody retains the ability to selectively bind to FGFR2-IIIb without detectably binding to FGFR2-IIIc. In certain embodiments, a total of 1 to 10 amino acids have been substituted, inserted and/or deleted in SEQ ID NO: 4. In certain embodiments, substitutions, insertions, or deletions occur in regions outside the HVRs (i.e., in the FRs). Optionally, the anti-FGFR2-IIIb antibody comprises the VH sequence in SEQ ID NO: 5, including post-translational modifications of that sequence. In a particular embodiment, the VH comprises one, two or three HVRs selected from: (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8. In some embodiments, the antibody is afucosylated. In some embodiments, the antibody is an IgG1 or IgG3 antibody that lacks fucose at Asn297.

In some embodiments, the anti-FGFR2-IIIb antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 5. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR2-IIIb antibody comprising that sequence retains the ability to bind to FGFR2-IIIb. In certain embodiments, the anti-FGFR2-IIIb antibody retains the ability to selectively bind to FGFR2-IIIb without binding to FGFR2-IIIc. In certain embodiments, a total of 1 to 10 amino acids have been substituted, inserted and/or deleted in SEQ ID NO: 5. In certain embodiments, the substitutions, insertions, or deletions occur in regions outside the HVRs (i.e., in the FRs). Optionally, the anti-FGFR2-IIIb antibody comprises the VL sequence in SEQ ID NO: 4, including post-translational modifications of that sequence. In a particular embodiment, the VL comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11. In some embodiments, the antibody is afucosylated. In some embodiments, the antibody is an IgG1 or IgG3 antibody that lacks fucose at Asn297.

In some embodiments, the anti-FGFR2-IIIb antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 4 and a light chain variable domain (VL) having at least 90%, 91%, 92%, 93%, 94%, 95%, 96%, 97%, 98%, 99%, or 100% sequence identity to the amino acid sequence of SEQ ID NO: 5. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, and a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR2-IIIb antibody comprising that sequence retains the ability to bind to FGFR2-IIIb. In certain embodiments, such an anti-FGFR2-IIIb antibody retains the ability to selectively bind to FGFR2-IIIb without binding to FGFR2-IIIc. In certain embodiments, a total of 1 to 10 amino acids have been substituted, inserted and/or deleted in SEQ ID NO: 4. In certain embodiments, a total of 1 to 10 amino acids have been substituted, inserted and/or deleted in SEQ ID NO: 5. In certain embodiments, substitutions, insertions, or deletions occur in regions outside the HVRs (i.e., in the FRs). Optionally, the anti-FGFR2-IIIb antibody comprises the VH sequence in SEQ ID NO: 4 and the VL sequence of SEQ ID NO: 5, including post-translational modifications of one or both sequence. In a particular embodiment, the VH comprises one, two or three HVRs selected from: (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8; and the VL comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11. In some embodiments, the antibody is afucosylated. In some embodiments, the antibody is an IgG1 or IgG3 antibody that lacks fucose at Asn297.

In some embodiments, the anti-FGFR2-IIIb antibody a VH as in any of the embodiments provided above, and a VL as in any of the embodiments provided above. In one embodiment, the antibody comprises the VH and VL sequences in SEQ ID NO: 4 and SEQ ID NO: 5, respectively, including post-translational modifications of those sequences. In some embodiments, the antibody is afucosylated. In some embodiments, the antibody is an IgG1 or IgG3 antibody that lacks fucose at Asn297.

In some embodiments, the anti-FGFR2-IIIb antibody comprises a heavy chain sequence having at least 90%, 91%, 92%, 93%, 94%, 95%, 96%, 97%, 98%, 99%, or 100% sequence identity to the amino acid sequence of SEQ ID NO: 2. In certain embodiments, a heavy chain sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR2-IIIb antibody comprising that sequence retains the ability to bind to FGFR2-IIIb. In certain embodiments, such an anti-FGFR2-IIIb antibody retains the ability to selectively bind to FGFR2-IIIb without detectably binding to FGFR2-IIIc. In certain embodiments, a total of 1 to 10 amino acids have been substituted, inserted and/or deleted in SEQ ID NO: 2. In certain embodiments, substitutions, insertions, or deletions occur in regions outside the HVRs (i.e., in the FRs). Optionally, the anti-FGFR2-IIIb antibody heavy chain comprises the VH sequence in SEQ ID NO: 2, including post-translational modifications of that sequence. In a particular embodiment, the heavy chain comprises one, two or three HVRs selected from: (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8. In some embodiments, the antibody is afucosylated. In some embodiments, the antibody is an IgG1 or IgG3 antibody that lacks fucose at Asn297.

In some embodiments the anti-FGFR2-IIIb antibody comprises a light chain having at least 90%, 91%, 92%, 93%, 94%, 95%, 96%, 97%, 98%, 99%, or 100% sequence identity to the amino acid sequence of SEQ ID NO: 3. In certain embodiments, a light chain sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR2-IIIb antibody comprising that sequence retains the ability to bind to FGFR2-IIIb. In certain embodiments, such an anti-FGFR2-IIIb antibody retains the ability to selectively bind to FGFR2-IIIb without detectably binding to FGFR2-IIIc. In certain embodiments, a total of 1 to 10 amino acids have been substituted, inserted and/or deleted in SEQ ID NO: 3. In certain embodiments, the substitutions, insertions, or deletions occur in regions outside the HVRs (i.e., in the FRs). Optionally, the anti-FGFR2-IIIb antibody light chain comprises the VL sequence in SEQ ID NO: 3, including post-translational modifications of that sequence. In a particular embodiment, the light chain comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11. In some embodiments, the antibody is afucosylated. In some embodiments, the antibody is an IgG1 or IgG3 antibody that lacks fucose at Asn297.

In some embodiments, the anti-FGFR2-IIIb antibody comprises a heavy chain sequence having at least 90%, 91%, 92%, 93%, 94%, 95%, 96%, 97%, 98%, 99%, or 100% sequence identity to the amino acid sequence of SEQ ID NO: 2 and a light chain sequence having at least 90%, 91%, 92%, 93%, 94%, 95%, 96%, 97%, 98%, 99%, or 100% sequence identity to the amino acid sequence of SEQ ID NO: 3. In certain embodiments, a heavy chain sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR2-IIIb antibody comprising that sequence retains the ability to bind to FGFR2-IIIb. In certain embodiments, such an anti-FGFR2-IIIb antibody retains the ability to selectively bind to FGFR2-IIIb without detectably binding to FGFR2-IIIc. In certain embodiments, a light chain sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR2-IIIb antibody comprising that sequence retains the ability to bind to FGFR2-IIIb. In certain embodiments, such an FGFR2-IIIb antibody retains the ability to selectively bind to FGFR2-IIIb without detectably binding to FGFR2-IIIc. In certain embodiments, a total of 1 to 10 amino acids have been substituted, inserted and/or deleted in SEQ ID NO: 2. In certain embodiments, a total of 1 to 10 amino acids have been substituted, inserted and/or deleted in SEQ ID NO: 3. In certain embodiments, substitutions, insertions, or deletions occur in regions outside the HVRs (i.e., in the FRs). Optionally, the anti-FGFR2-IIIb antibody heavy chain comprises the VH sequence in SEQ ID NO: 2, including post-translational modifications of that sequence and the anti-FGFR2-IIIb antibody light chain comprises the VL sequence in SEQ ID NO: 3, including post-translational modifications of that sequence. In a particular embodiment, the heavy chain comprises one, two or three HVRs selected from: (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8; and the light chain comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11. In some embodiments, the antibody is afucosylated. In some embodiments, the antibody is an IgG1 or IgG3 antibody that lacks fucose at Asn297.

Additional exemplary anti-FGFR2 antibodies are the GAL-FR22 and GAL-FR23 antibodies described in U.S. Pat. No. 8,101,723 B2, incorporated by reference herein. The light and heavy chain variable regions of GAL-FR22, for example, are provided as SEQ ID NOs: 7 and 8 in U.S. Pat. No. 8,101,723 B2, while the Kabat CDRs and the light and heavy chain variable regions are also provided in FIG. 16 of that patent, which are incorporated by reference herein. The GAL-FR21, GAL-FR22 and GAL-FR23 producing hybridomas are deposited at the American Type Culture Collection, PO Box 1549, Manassas Va., USA, 20108, as ATCC Numbers 9586, 9587, and 9408, on November 6, November 6, and Aug. 12, 2008, respectively. Thus, in some embodiments, the FGFR2 antibody is an antibody comprising the amino acid sequence of an antibody obtained from one of those three hybridoma strains.

The heavy and light chain variable regions of GAL-FR22 are also presented herein as SEQ ID NOs: 39 and 43, while the Kabat CDRs are presented herein as SEQ ID NOs: 40-42 and 44-46. Thus, in some embodiments the anti-FGFR2-IIIb antibody heavy chain variable region comprises: (i) CDR1 comprising the amino acid sequence of SEQ ID NO: 40; (ii) CDR2 comprising the amino acid sequence of SEQ ID NO: 41; and (iii) CDR3 comprising the amino acid sequence of SEQ ID NO: 42; and the light chain variable region comprises: (iv) CDR1 comprising the amino acid sequence of SEQ ID NO: 44; (v) CDR2 comprising the amino acid sequence of SEQ ID NO: 45; and (vi) CDR3 comprising the amino acid sequence of SEQ ID NO: 46.

In some embodiments, the anti-FGFR2 antibody comprises an anti-FGFR2-IIIb antibody in which the heavy chain variable domain that is at least 95%, such as at least 97%, at least 98%, or at least 99% identical to the amino acid sequence of SEQ ID NO:39, or that comprises the amino acid sequence of SEQ ID NO: 39. In some embodiments, the anti-FGFR2 antibody comprises an anti-FGFR2-IIIb antibody in which the light chain variable domain is at least 95%, such as at least 97%, at least 98%, or at least 99% identical to the amino acid sequence of SEQ ID NO: 43, or that comprises the amino acid sequence of SEQ ID NO: 43. In some embodiments, the heavy chain variable domain is at least 95%, such as at least 97%, at least 98%, or at least 99% identical to the amino acid sequence of SEQ ID NO:39, or that comprises the amino acid sequence of SEQ ID NO: 39 and the light chain variable domain is at least 95%, such as at least 97%, at least 98%, or at least 99% identical to the amino acid sequence of SEQ ID NO:43, or that comprises the amino acid sequence of SEQ ID NO: 43. In some embodiments, the antibody is an IgG1 or IgG3 antibody that lacks fucose at Asn297.

In any of the methods described herein, the anti-FGFR2 antibody may be a humanized antibody, chimeric antibody, or human antibody. In any of the compositions or methods described herein, the anti-FGFR2 antibody may be selected from a Fab, an Fv, an scFv, a Fab', and a (Fab')2. In any of the compositions or methods described herein, the anti-FGFR2 antibody may be selected from an IgA, an IgG, and an IgD. In any of the compositions or methods described herein, the anti-FGFR2 antibody may be an IgG. In any of the methods described herein, the antibody may be an IgG1 or IgG3.

Exemplary Properties of Antibodies

In some embodiments, the anti-FGFR2-IIIb antibody binds to FGFR2-IIIb with higher affinity than to FGFR2-IIIc or does not detectably bind to FGFR2-IIIc; inhibits binding of FGF2 to human FGFR2; and/or inhibits binding of FGF7 to human FGFR2. Binding of antibody to FGFR2 and inhibition of binding between FGFR2 and FGFs can be assessed, for example, by ELISA assays, as described in U.S. Pat. No. 8,101,723, or, for example, by a chip-based assay as described in Example 2 of WO 2015/-17600. In some embodiments, the antibody induces an ADCC activity, and in some embodiments possesses enhanced ADCC activity, for example, as described in WO 2015/-17600. ADCC activity, for example, may be determined as described in Example 3 of WO 2015/-17600. In some embodiments, the antibody may inhibit growth of a human tumor in a mouse model, for example, as shown in Example 1 of International Application No. PCT/US2016/063332. In some embodiments, the anti-FGFR2-IIIb antibody is capable of increasing the number of one or more of PD-L1 positive cells, NK cells, CD3+ T cells, CD4+ T cells, CD8+ T cells, and macrophages in tumor tissue in a mouse tumor model compared to a control, for example, as described in Example 2 of International Application No. PCT/US2016/063332.

Afucosylated Anti-FGFR2 Antibodies

In some embodiments, anti-FGFR2 antibodies, for example the anti-FGFR2-IIIb antibodies as described above, have a carbohydrate structure that lacks fucose attached (directly or indirectly) to an Fc region (i.e., afucosylated antibodies), i.e, the antibodies are afucosylated. In some embodiments, the afucosylated antibody is an IgG1 or IgG3 antibody that lacks fucose at Asn297.

Herein, antibodies are considered to be afucosylated when a plurality of such antibodies comprises at least 95% afucosylated antibodies. The amount of fucose may be determined by calculating the average amount of fucose within the sugar chain at Asn297 relative to the sum of all glycostructures attached to Asn 297 (e.g., complex, hybrid and high mannose structures). Nonlimiting exemplary methods of detecting fucose in an antibody include MALDI-TOF mass spectrometry (see, e.g., WO 2008/077546), HPLC measurement of released fluorescently labeled oligosaccharides (see, e.g., Schneider et al., "N-Glycan analysis of monoclonal antibodies and other glycoproteins using UHPLC with fluorescence detection," Agilent Technologies, Inc. (2012); Lines, J. Pharm. Biomed. Analysis, 14: 601-608 (1996); Takahasi, J. Chrom., 720: 217-225 (1996)), capillary electrophoresis measurement of released fluorescently labeled oligosaccharides (see, e.g., Ma et al., Anal. Chem., 71: 5185-5192 (1999)), and HPLC with pulsed amperometric detection to measure monosaccharide composition (see, e.g., Hardy, et al., Analytical Biochem., 170: 54-62 (1988)).

Asn297 refers to the asparagine residue located at about position 297 in the Fc region (EU numbering of Fc region residues); however, in a given antibody sequence, Asn297 may also be located about ±3 amino acids upstream or downstream of position 297, i.e., between positions 294 and 300, due to minor sequence variations in antibodies. In an anti-FGFR2-IIIb antibody described herein, Asn297 is found in the sequence QYNST (positions 292-296 of SEQ ID NO:

2), and is in bold and underlined in the Table of Sequences shown below, SEQ ID NO: 2.

Fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "afucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing afucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as cell lines lacking a functional alpha-1,6-fucosyltransferase gene, FUT8, e.g., knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Anti-FGFR2 antibodies herein may also have bisected oligosaccharides, e.g., in which a biantennary oligosaccharide attached to the Fc region of the antibody is bisected by GlcNAc. Such antibodies may have reduced fucosylation and/or improved ADCC function. Examples of such antibodies are described, e.g., in WO 2003/011878 (Jean-Mairet et al.); U.S. Pat. No. 6,602,684 (Umana et al.); and US 2005/0123546 (Umana et al.). In some embodiments, anti-FGFR2 antibodies have at least one galactose residue in the oligosaccharide attached to the Fc region. Such antibodies may have improved CDC function. Such antibodies are described, e.g., in WO 1997/30087 (Patel et al.); WO 1998/58964 (Raju, S.); and WO 1999/22764 (Raju, S.).

In some embodiments of the invention, an afucosylated anti-FGFR2 antibody mediates ADCC in the presence of human effector cells more effectively than an antibody with the same amino acid sequence that comprises fucose. Generally, ADCC activity may be determined using the in vitro ADCC assay disclosed in U.S. Patent Publication No. 2015-0050273 A1, but other assays or methods for determining ADCC activity, e.g. in an animal model etc., are contemplated.

In some embodiments, the anti-FGFR2 antibody comprises the heavy and light chain sequences of SEQ ID NOs: 2 and 3. In some embodiments, the antibody comprising the heavy and light chain sequences of SEQ ID NOs: 2 and 3 is afucosylated.

Exemplary Antibody Constant Regions

In some embodiments, an anti-FGFR2 described herein comprises one or more human constant regions. In some embodiments, the human heavy chain constant region is of an isotype selected from IgA, IgG, and IgD. In some embodiments, the human light chain constant region is of an isotype selected from κ and λ.

In some embodiments, an antibody described herein comprises a human IgG constant region. In some embodiments, when effector function is desirable, an antibody comprising a human IgG1 heavy chain constant region or a human IgG3 heavy chain constant region is selected. In some embodiments, an antibody described herein comprises a human IgG1 constant region. In some embodiments, an antibody described herein comprises a human IgG1 constant region, wherein N297 is not fucosylated. In some embodiments, an antibody described herein comprises a human IgG1 constant region and a human κ light chain.

Throughout the present specification and claims unless explicitly stated or known to one skilled in the art, the numbering of the residues in an immunoglobulin heavy chain is that of the EU index as in Kabat et al., *Sequences of Proteins of Immunological Interest,* 5th Ed. Public Health Service, National Institutes of Health, Bethesda, Md. (1991), expressly incorporated herein by reference. The "EU index as in Kabat" refers to the residue numbering of the human IgG1 EU antibody.

In certain embodiments, an antibody of the invention comprises a variant Fc region has at least one amino acid substitution compared to the Fc region of a wild-type IgG or a wild-type antibody. In certain embodiments, the variant Fc region has two or more amino acid substitutions in the Fc region of the wild-type antibody. In certain embodiments, the variant Fc region has three or more amino acid substitutions in the Fc region of the wild-type antibody. In certain embodiments, the variant Fc region has at least one, two or three or more Fc region amino acid substitutions described herein. In certain embodiments, the variant Fc region herein will possess at least about 80% homology with a native sequence Fc region and/or with an Fc region of a parent antibody. In certain embodiments, the variant Fc region herein will possess at least about 90% homology with a native sequence Fc region and/or with an Fc region of a parent antibody. In certain embodiments, the variant Fc region herein will possess at least about 95% homology with a native sequence Fc region and/or with an Fc region of a parent antibody.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibodies with certain improved properties.

Antibodies may also have amino-terminal leader extensions. For example, one or more amino acid residues of the amino-terminal leader sequence are present at the amino-terminus of any one or more heavy or light chains of an antibody. An exemplary amino-terminal leader extension comprises or consists of three amino acid residues, VHS, present on one or both light chains of an antibody.

The in vivo or serum half-life of human FcRn high affinity binding polypeptides can be assayed, e.g., in transgenic mice, in humans, or in non-human primates to which the polypeptides with a variant Fc region are administered. See also, e.g., Petkova et al. *International Immunology* 18(12): 1759-1769 (2006).

Exemplary Chimeric Antibodies

In certain embodiments, an anti-FGFR2 antibody provided herein is a chimeric antibody. Certain chimeric antibodies are described, e.g., in U.S. Pat. No. 4,816,567; and Morrison et al., (1984) *Proc. Natl. Acad. Sci. USA*, 81: 6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

Nonlimiting exemplary chimeric antibodies include chimeric antibodies against FGFR2 comprising heavy chain HVR1, HVR2, and HVR3, and/or light chain HVR1, HVR2, and HVR3 sequences described herein.

In some embodiments, a chimeric antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, a chimeric antibody described herein comprises a human IgG constant region. In some embodiments, a chimeric antibody described herein comprises a human IgG4 heavy chain constant region. In some embodiments, a chimeric antibody described herein comprises a human IgG4 constant region and a human κ light chain.

As noted above, whether or not effector function is desirable may depend on the particular method of treatment intended for an antibody. Thus, in some embodiments, when effector function is desirable, a chimeric antibody comprising a human IgG1 heavy chain constant region or a human IgG3 heavy chain constant region is selected. In some embodiments, when effector function is not desirable, a chimeric antibody comprising a human IgG4 or IgG2 heavy chain constant region is selected. In some embodiments, a chimeric antibody described herein comprises a human IgG1 constant region wherein N297 is not fucosylated. In some embodiments, a chimeric antibody described herein comprises a human IgG1 constant region and a human κ light chain.

Exemplary Humanized Antibodies

In some embodiments, humanized antibodies that bind FGFR2 are used. Humanized antibodies are useful as therapeutic molecules because humanized antibodies reduce or eliminate the human immune response to non-human antibodies (such as the human anti-mouse antibody (HAMA) response), which can result in an immune response to an antibody therapeutic, and decreased effectiveness of the therapeutic.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs or CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, (2008) *Front. Biosci.* 13: 1619-1633, and are further described, e.g., in Riechmann et al., (1988) *Nature* 332:323-329; Queen et al., (1989) *Proc. Natl Acad. Sci. USA* 86: 10029-10033; U.S. Pat. Nos. 5,821,337, 7,527,791, 6,982,321, and 7,087,409; Kashmiri et al., (2005) *Methods* 36:25-34 (describing SDR (a-CDR) grafting); Padlan, (1991) *Mol. Immunol.* 28:489-498 (describing "resurfacing"); Dall'Acqua et al., (2005) *Methods* 36:43-60 (describing "FR shuffling"); and Osbourn et al., (2005) *Methods* 36:61-68 and Klimka et al., (2000) *Br. I Cancer*, 83:252-260 (describing the "guided selection" approach to FR shuffling).

Human framework regions that may be used for humanization include but are not limited to: framework regions selected using the "best-fit" method (see, e.g., Sims et al. (1993) *J. Immunol.* 151: 2296); framework regions derived from the consensus sequence of human antibodies of a particular subgroup of light or heavy chain variable regions (see, e.g., Carter et al. (1992) *Proc. Natl. Acad. Sci. USA,* 89:4285; and Presta et al. (1993) *J. Immunol,* 151:2623); human mature (somatically mutated) framework regions or human germline framework regions (see, e.g., Almagro and Fransson, (2008) *Front. Biosci.* 13:1619-1633); and framework regions derived from screening FR libraries (see, e.g., Baca et al., (1997) *J. Biol. Chem.* 272: 10678-10684 and Rosok et al., (1996) *J. Biol. Chem.* 271: 22611-22618).

In some embodiments, humanized antibodies comprise one or more human constant regions. In some embodiments, the human heavy chain constant region is of an isotype selected from IgA, IgG, and IgD. In some embodiments, the human light chain constant region is of an isotype selected from κ and λ.

In some embodiments, a humanized antibody described herein comprises a human IgG constant region. In some embodiments, when effector function is desirable, the antibody comprises a human IgG1 heavy chain constant region or a human IgG3 heavy chain constant region. In some embodiments, a humanized antibody described herein comprises a human IgG1 constant region. In some embodiments, a humanized antibody described herein comprises a human IgG1 constant region wherein N297 is not fucosylated. In some embodiments, a humanized antibody described herein comprises a human IgG1 constant region and a human κ light chain.

Human Antibodies

Human anti-FGFR2 antibodies can be made by any suitable method. Nonlimiting exemplary methods include making human antibodies in transgenic mice that comprise human immunoglobulin loci. See, e.g., Jakobovits et al., *Proc. Natl. Acad. Sci. USA* 90: 2551-55 (1993); Jakobovits et al., *Nature* 362: 255-8 (1993); Lonberg et al., *Nature* 368: 856-9 (1994); and U.S. Pat. Nos. 5,545,807; 6,713,610; 6,673,986; 6,162,963; 5,545,807; 6,300,129; 6,255,458; 5,877,397; 5,874,299; and 5,545,806.

Nonlimiting exemplary methods also include making human antibodies using phage display libraries. See, e.g., Hoogenboom et al., *J. Mol. Biol.* 227: 381-8 (1992); Marks et al., *J. Mol. Biol.* 222: 581-97 (1991); and PCT Publication No. WO 99/10494.

In some embodiments, a human antibody comprises one or more human constant regions. In some embodiments, the human heavy chain constant region is of an isotype selected from IgA, IgG, and IgD. In some embodiments, the human light chain constant region is of an isotype selected from κ and λ. In some embodiments, a human antibody described herein comprises a human IgG constant region. In some embodiments, a human antibody described herein comprises a human IgG4 heavy chain constant region. In some such embodiments, a human antibody described herein comprises an S241P mutation in the human IgG4 constant region. In some embodiments, a human antibody described herein comprises a human IgG4 constant region and a human κ light chain.

In some embodiments, when effector function is desirable, a human antibody comprising a human IgG1 heavy chain constant region or a human IgG3 heavy chain constant region is selected. In some embodiments, when effector function is not desirable, a human antibody comprising a human IgG4 or IgG2 heavy chain constant region is selected. In some embodiments, a humanized antibody described herein comprises a human IgG1 constant region wherein N297 is not fucosylated. In some embodiments, a humanized antibody described herein comprises a human IgG1 constant region and a human κ light chain.

Exemplary Antibody Conjugates

In some embodiments, an anti-FGFR2 antibody is conjugated to a label and/or a cytotoxic agent. As used herein, a label is a moiety that facilitates detection of the antibody and/or facilitates detection of a molecule to which the antibody binds. Nonlimiting exemplary labels include, but are not limited to, radioisotopes, fluorescent groups, enzymatic groups, chemiluminescent groups, biotin, epitope tags, metal-binding tags, etc. One skilled in the art can select a suitable label according to the intended application.

As used herein, a cytotoxic agent is a moiety that reduces the proliferative capacity of one or more cells. A cell has reduced proliferative capacity when the cell becomes less able to proliferate, for example, because the cell undergoes apoptosis or otherwise dies, the cell fails to proceed through the cell cycle and/or fails to divide, the cell differentiates, etc. Nonlimiting exemplary cytotoxic agents include, but are not limited to, radioisotopes, toxins, and chemotherapeutic agents. One skilled in the art can select a suitable cytotoxic according to the intended application.

In some embodiments, a label and/or a cytotoxic agent is conjugated to an antibody using chemical methods in vitro. Nonlimiting exemplary chemical methods of conjugation are known in the art, and include services, methods and/or reagents commercially available from, e.g., Thermo Scientific Life Science Research Produces (formerly Pierce; Rockford, IL), Prozyme (Hayward, CA), SACRI Antibody Services (Calgary, Canada), AbD Serotec (Raleigh, NC), etc. In some embodiments, when a label and/or cytotoxic agent is a polypeptide, the label and/or cytotoxic agent can be expressed from the same expression vector with at least one antibody chain to produce a polypeptide comprising the label and/or cytotoxic agent fused to an antibody chain. One skilled in the art can select a suitable method for conjugating a label and/or cytotoxic agent to an antibody according to the intended application.

Nucleic Acid Molecules Encoding Antibodies

Nucleic acid molecules comprising polynucleotides that encode one or more chains of an antibody are provided. In some embodiments, a nucleic acid molecule comprises a polynucleotide that encodes a heavy chain or a light chain of an antibody. In some embodiments, a nucleic acid molecule comprises both a polynucleotide that encodes a heavy chain and a polynucleotide that encodes a light chain, of an antibody. In some embodiments, a first nucleic acid molecule comprises a first polynucleotide that encodes a heavy chain and a second nucleic acid molecule comprises a second polynucleotide that encodes a light chain.

In some such embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an antibody comprises a nucleotide sequence that encodes a leader sequence, which, when translated, is located at the N terminus of the heavy chain or light chain. As discussed above, the leader sequence may be the native heavy or light chain leader sequence, or may be another heterologous leader sequence.

Nucleic acid molecules may be constructed using recombinant DNA techniques conventional in the art. In some embodiments, a nucleic acid molecule is an expression vector that is suitable for expression in a selected host cell.

Antibody Expression and Production

Vectors

Vectors comprising polynucleotides that encode antibody heavy chains and/or light chains are provided. Vectors comprising polynucleotides that encode antibody heavy chains and/or light chains are also provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NSO cells. Exemplary such vectors are described, e.g., in Running Deer et al., *Biotechnol. Prog.* 20:880-889 (2004).

In some embodiments, a vector is chosen for in vivo expression of antibody heavy chains and/or antibody light chains in animals, including humans. In some such embodiments, expression of the polypeptide is under the control of a promoter that functions in a tissue-specific manner. For example, liver-specific promoters are described, e.g., in PCT Publication No. WO 2006/076288.

Host Cells

In various embodiments, antibody heavy chains and/or light chains may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S and DG44 cells; PER.C6® cells (Crucell); and NSO cells. In some embodiments, antibody heavy chains and/or light chains may be expressed in yeast. See, e.g., U.S. Publication No. US 2006/0270045 A1. In some embodiments, a particular eukaryotic host cell is selected based on its ability to make desired post-translational modifications to the antibody heavy chains and/or light chains. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., *Molecular Cloning, A Laboratory Manual, 3rd ed.* Cold Spring Harbor Laboratory Press (2001). Nucleic acids may be transiently or stably transfected in the desired host cells, according to any suitable method.

In some embodiments, one or more polypeptides may be produced in vivo in an animal that has been engineered or transfected with one or more nucleic acid molecules encoding the polypeptides, according to any suitable method.

Purification of Antibodies

Antibodies may be purified by any suitable method. Such methods include, but are not limited to, the use of affinity matrices or hydrophobic interaction chromatography. Suitable affinity ligands include the antigen and ligands that bind antibody constant regions. For example, a Protein A, Protein G, Protein A/G, or an antibody affinity column may be used to bind the constant region and to purify an antibody. Hydrophobic interactive chromatography, for example, a butyl or phenyl column, may also suitable for purifying some polypeptides. Many methods of purifying polypeptides are known in the art.

Cell-Free Production of Antibodies

In some embodiments, an antibody is produced in a cell-free system. Nonlimiting exemplary cell-free systems are described, e.g., in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

Modified FOLFOX6

The chemotherapy regimen modified FOLFOX6 (mFOLFOX6) comprises a regimen in which a combination of oxaliplatin (e.g. Eloxatin®), leucovorin (e.g. leucovorin calcium or folinic acid), and 5-fluorouracil (5-FU) are each administered intravenously in succession over about a 2-day total period. Modified FOLFOX6 has been used as a first line treatment for advanced gastric cancer. A randomized Phase 3 trial comparing mFOLFOX6 with 5-FU/LV/cisplatin (FLP) in the treatment of 220 patients with gastric cancer reported a statistically insignificant improved time-to-progression; however, mFOLFOX6 was associated with meaningful reductions in Grade 3/4 adverse events, including neutropenia, anemia, and peripheral neuropathy. (Al-Batran et al., *J. Clin. Oncol.* 26: 1435-42 (2008).) Subsequent studies have confirmed the safety and efficacy of mFOLFOX6 in advanced gastric cancer. (B. Keam, *BMC Cancer*, 8: 148 (2008).)

In some embodiments, a combination of oxaliplatin (e.g. Eloxatin®), leucovorin (e.g. leucovorin calcium or folinic acid), and 5-fluorouracil (5-FU) are each administered by IV infusion or IV bolus over the course of about 2-8 hours and a further infusion of 5-FU is then administered by IV infusion over an about 44-48-hour period. In some embodiments, the mFOLFOX6 regimen comprises: oxaliplatin administered on day 1 at 50-100 mg/m$^2$ by IV, for example, over 2 hours, then leucovorin administered on day 1 at 100-400 mg/m$^2$ by IV, for example, over 2 hours, then 5-FU administered at 100-400 mg/m$^2$ by IV bolus or IV infusion, all on day 1, and followed by further 5-FU IV infusion of 2000-2500 mg/m$^2$ over 44-48 hours, such as 46 hours. In some embodiments, the mFOLFOX6 regimen comprises: oxaliplatin administered on day 1 at 75-100 mg/m$^2$ by IV, for example, over 2 hours, then leucovorin administered on day 1 at 200-400 mg/m$^2$ by IV, for example, over 2 hours, then 5-FU administered at 200-400 mg/m$^2$ by IV bolus or IV infusion, all on day 1, and followed by further 5-FU IV infusion of 2200-2400 mg/m$^2$ over 44-48 hours, such as 46 hours. In some embodiments, the mFOLFOX6 regimen comprises: oxaliplatin administered on day 1 at 75-90 mg/m$^2$ by IV, for example, over 2 hours, then leucovorin administered on day 1 at 300-400 mg/m$^2$ by IV, for example, over 2 hours, then 5-FU administered at 300-400 mg/m$^2$ by IV bolus or IV infusion, all on day 1, and followed by further 5-FU IV infusion of 2200-2400 mg/m$^2$ over 44-48 hours, such as 46 hours.

In some embodiments, the mFOLFOX6 regimen comprises: oxaliplatin administered on day 1 at 85 mg/m$^2$ by IV, for example, over 2 hours, then leucovorin administered on day 1 at 400 mg/m$^2$ by IV, for example, over 2 hours, then 5-FU administered at 400 mg/m$^2$ by IV bolus or IV infusion, all on day 1, and followed by further 5-FU IV infusion of 2400 mg/m$^2$ over 44-48 hours, such as 46 hours. For example, a starting dose for mFOLFOX6 as first line gastric cancer treatment may include 85 mg/m$^2$ of oxaliplatin, 350 mg of calcium folinate (folinic acid), a 400-mg/m$^2$ dose of fluorouracil, followed by a 2400-mg/m$^2$ dose of fluorouracil infused over 46 hours.

In some embodiments, the mFOLFOX6 regimen may be administered once every 10 to 21 days, such as once every 10-15 days, once every 10 days, once every 11 days, once every 12 days, once every 13 days, once every 14 days, once every 15 days, once every 16 days, once every 17 days, once every 18 days, once every 19 days, once every 20 days, or once every 21 days.

In some embodiments, the mFOLFOX6 may be administered once every "2 weeks," which, as used in the context of a general dosage regime herein, means once every 14 days plus or minus 3 days, or once every 11-17 days.

Therapeutic Compositions and Methods

Methods of Treating Cancer

In some embodiments, methods for treating cancer are provided, comprising administering an effective amount of an anti-FGFR2 antibody, such as an anti-FGFR2-IIIb antibody as described herein, in combination with a modified FOLFOX6 chemotherapy regimen (mFOLFOX6). In some embodiments, the cancer is a gastrointestinal (GI) cancer such as gastric cancer, colorectal cancer, and pancreatic adenocarcinoma. In some embodiments, the cancer is unresectable, locally advanced, or metastatic gastric cancer.

In some embodiments of the methods, the anti-FGFR2-IIIb antibody is administered at a dose of 6-15 mg/kg, 10-15 mg/kg, 6 mg/kg, 7 mg/kg, 8 mg/kg, 9 mg/kg, 10 mg/kg, 11 mg/kg, 12 mg/kg, 13 mg/kg, 14 mg/kg, or 15 mg/kg. In some embodiments, the anti-FGFR2-IIIb antibody is administered once every 7-21 days, once every 7-15 days, once every 7-10 days, once every 10-14 days, once every 11-17 days, once every 12-16 days, once every 13-15 days, once every 7 days, once every 8 days, once every 9 days, once every 10 days, once every 11 days, once every 12 days, once every 13 days, once every 14 days, once every 15 days, once every 16 days, once every 17 days, once every 18 days, once every 19 days, once every 20 days, or once every 21 days. In some embodiments, the anti-FGFR2-IIIb antibody may be administered once every 2 weeks, meaning once every 14 days plus or minus 3 days, or once every 11-17 days.

In some embodiments, the anti-FGFR2-IIIb antibody is administered in a dosage regime of 6-15 mg/kg every 2 weeks. In some embodiments, the anti-FGFR2-IIIb antibody is administered in a dosage regime of 6-15 mg/kg every 13-15 days. In some embodiments, the anti-FGFR2-IIIb antibody is administered in a dosage regime of 6-15 mg/kg every 14 days. In some embodiments, the anti-FGFR2-IIIb antibody is administered in a dosage regime of 6, 10, or 15 mg/kg every 2 weeks. In some embodiments, the anti-FGFR2-IIIb antibody is administered in a dosage regime of 6, 10, or 15 mg/kg every 13-15 days. In some embodiments, the anti-FGFR2-IIIb antibody is administered in a dosage regime of 6, 10, or 15 mg/kg every 14 days.

In some embodiments, a dosage regime is used in which two doses are administered 2 weeks apart, and an intervening booster dose is administered at a time in between those two doses, wherein the intervening booster dose is lower than the two doses. Dosing in such a regime may help to maintain the antibody in circulation at a reasonable or relatively steady concentration over time. For example, if the concentration of antibody in circulation following a dose falls to a trough about a week after administration, then giving a lower booster dose at or near that trough point followed by another regular dose about a week after the booster dose can help to steady the overall concentration of antibody in circulation over time and prevent the concentration from falling too low in between doses.

Accordingly, in some embodiments, the anti-FGFR2-IIIb antibody is administered in a dosage regime of 6-15 mg/kg every 2 weeks, and an intervening booster dose, which is at a lower dose than the 6-15 mg/kg dose, is administered 1 week (meaning 7 plus or minus 2 days or 5-9 days) after the first of two 6-15 mg/kg doses and 1 week (i.e. 5-9 days) before the second of the two 6-15 mg/kg doses. In some such embodiments, the booster dose is 3-8 mg/kg. In some embodiments, the booster dose is half the dose of the immediately preceding and following doses. In some embodiments, the anti-FGFR2-IIIb antibody is administered in a dosage regime of 6-15 mg/kg every 2 weeks and an intervening booster dose of 3-8 mg/kg is administered 6-8 days after the first of two 6-15 mg/kg doses and 6-8 days before the second of the two 6-15 mg/kg doses. In some embodiments, the anti-FGFR2-IIIb antibody is administered in a dosage regime of 10-15 mg/kg every 2 weeks and an intervening booster dose of 5-8 mg/kg is administered 6-8 days after the first of two 10-15 mg/kg doses and 6-8 days before the second of the two 10-15 mg/kg doses. In some embodiments, the anti-FGFR2-IIIb antibody is administered in a dosage regime of 15 mg/kg every 2 weeks and an intervening booster dose of 7-8 mg/kg is administered 6-8 days after the first of two 15 mg/kg doses and 6-8 days before the second of the two 15 mg/kg doses. In some embodiments, the anti-FGFR2-IIIb antibody is administered in a dosage regime of 15 mg/kg every 13-15 days and an intervening booster dose of 7-8 mg/kg is administered 6-8 days after the first of two 15 mg/kg doses and 6-8 days before the second of the two 15 mg/kg doses. In some embodiments, the anti-FGFR2-IIIb antibody is administered in a dosage regime of 15 mg/kg every 14 days and an intervening booster dose of 7-8 mg/kg is administered 6-8 days after the first of two 15 mg/kg doses and 6-8 days before the second of the two 15 mg/kg doses. In some embodiments, the anti-FGFR2-IIIb antibody is administered in a dosage regime of 15 mg/kg every 14 days and an intervening booster dose of 7-8 mg/kg is administered 7 days after the first of two 15 mg/kg doses and 7 days before the second of the two 15 mg/kg doses. In some of the above embodiments, the booster dose is given only once, e.g. only between the first and second dose administrations of the antibody to the patient. In other embodiments, it is given only twice, e.g. between the first and second and the second and third dose administrations of the antibody.

In some embodiments, the anti-FGFR2-IIIb antibody is administered in a dosage regime of 15 mg/kg every 14 days and an intervening booster dose of 7.5 mg/kg is administered 7 days after the first of two 15 mg/kg doses and 7 days before the second of the two 15 mg/kg doses. In some embodiments, the anti-FGFR2-IIIb antibody is administered at a dose of 15 mg/kg once every 14 days, starting on day 1, and 7 days following the first administration of the anti-FGFR2-IIIb antibody (i.e. on day 8), the anti-FGFR2-IIIb antibody is administered at a booster dose of 7.5 mg/kg. In some such embodiments, the booster dose of 7.5 mg/kg is given only once, e.g. between the first and second 15 mg/kg antibody administrations only.

The anti-FGFR2-IIIb antibody and the mFOLFOX6 may be administered concurrently, such as on the same day, for example with the antibody being infused by IV prior to the start of the mFOLFOX6 regimen, or they may be dosed sequentially, such as on different days. In some embodiments, the mFOLFOX6 is administered at least once or at least twice prior to beginning treatment with the anti-FGFR2-IIIb antibody. In some embodiments, both the antibody and the mFOLFOX6 are administered once every 7-21 days, once every 7-15 days, once every 7-10 days, once every 10-14 days, once every 11-17 days, once every 12-16 days, once every 13-15 days, once every 7 days, once every 8 days, once every 9 days, once every 10 days, once every 11 days, once every 12 days, once every 13 days, once every 14 days, once every 15 days, once every 16 days, once every 17 days, once every 18 days, once every 19 days, once every 20 days, or once every 21 days. In some embodiments, the anti-FGFR2-IIIb and the mFOLFOX6 may be administered once every 2 weeks, meaning once every 14 days plus or minus 3 days, or once every 11-17 days.

In some embodiments, the anti-FGFR2-IIIb antibody comprises heavy chain and light chain variable regions, wherein the heavy chain variable region comprises:
  (i) HVR-H1 comprising the amino acid sequence of SEQ ID NO: 6;
  (ii) HVR-H2 comprising the amino acid sequence of SEQ ID NO: 7; and
  (iii) HVR-H3 comprising the amino acid sequence of SEQ ID NO: 8;
  and the light chain variable region comprises:
  (iv) HVR-L1 comprising the amino acid sequence of SEQ ID NO: 9;
  (v) HVR-L2 comprising the amino acid sequence of SEQ ID NO: 10; and
  (vi) HVR-L3 comprising the amino acid sequence of SEQ ID NO: 11;
and the anti-FGFR2-IIIb antibody is administered intravenously at a dose of 10-15 mg/kg followed by administration of the mFOLFOX6 comprising administration of 85 mg/m$^2$ oxaliplatin, 400 mg/m$^2$ leucovorin, and 400 mg/m$^2$ 5-fluorouracil (5-FU) by IV infusion or IV bolus followed by administration of 2400 mg/m$^2$ 5-FU by IV infusion over 44-48 hours; and the anti-FGFR2-IIIb and mFOLFOX6 are administered every 2 weeks, In some embodiments, the subject has gastric cancer comprising an FGFR2 gene amplification, whereas in some embodiments the cancer does not comprise an FGFR2 amplification. In some embodiments, fluorescence in situ hybridization (FISH) is used to assess gene amplification, such as with probes to the FGFR2 gene locus and the chromosome 10 centromere. In some embodiments, where an amplification occurs, the FGFR2 amplification comprises an FGFR2:CEN10 (chromosome 10 centromere) ratio of >3. In some embodiments, FGFR2 amplification comprises an FGFR2:CEN10 ratio of ≥2. In other embodiments, however, the FGFR2 level comprises an FGFR2:CEN10 ratio of between 1 and 2, indicating that FGFR2 is not amplified.

In some embodiments, the subject has gastric cancer overexpressing FGFR2, or overexpressing FGFR2-IIIb. In some embodiments, the cancer overexpresses FGFR2-IIIb to a greater extent than FGFR2-IIIc. In some embodiments, the cancer does not comprise a gene amplification, yet FGFR2-IIIb is overexpressed, while in other embodiments the cancer comprises both an FGFR2 gene amplification and overexpression of FGFR2-IIIb. In some embodiments, a cancer comprising FGFR2 amplification expresses FGFR2-IIIb at a normalized level that is more than 2-fold, 3-fold, 5-fold, or 10-fold greater than the normalized level of FGFR2-IIIc expression. In some embodiments, the expression levels are normalized to GUSB. In some embodiments, overexpression is mRNA overexpression. In some embodiments, overexpression is protein overexpression. In some embodiments, a point mutation or translocation may cause an overexpression of FGFR2.

In some embodiments, FGFR2 or FGFR2-IIIb overexpression is determined by immunohistochemistry (IHC). For example, the overexpression may be determined by an IHC signal of 1+, 2+, or 3+ in at least 10% of tumor cells, such as in at least 20%, 30%, 40%, or 50% of tumor cells. For example, in some such embodiments, patients to be treated may have, for instance, an IHC signal for FGFR2-IIIb of 2+ or 3+ in at least 10% of tumor cells (e.g. in cell membranes). In some embodiments, a patient may have 3+ signal in at least 10% of tumor cells. In some embodiments, a patient may have at least 1+ signal in at least 10% of tumor cells.

In some embodiments, the FGFR2 or FGFR2-IIIb overexpression may be reported as an "H score." To determine an H score, first membrane staining intensity may be determined for cells in a fixed field, such as via IHC to obtain scores of 0, 1+, 2+, or 3+ and the H score can be calculated using the formula as follows: 1×(% of cells visualized with IHC intensity of 1+)+2×(% of cells visualized with IHC intensity of 2+)+3×(% of cells visualized with IHC intensity of 3+). Theoretically, an H score may range from 0 to 300 and equals 300 if all of the cells in the visual field have IHC staining of 3+. In some embodiments, the patient to be treated has a starting H score for FGFR2, such as FGFR2-IIIb, of >20, such as >30, >40, >50, or >100, or a range of 20-300, 20-100, 20-50, 20-40, or 20-30. In some embodiments, the patient has an H score of >10 or is within a range of 10-20 or 15-20. In other embodiments, the patient has an H score of 0-10, which may indicate a lack of overexpression.

In some embodiments, the cancer, e.g. gastric cancer, has already been determined to overexpress FGFR2-IIIb and/or to carry an FGFR2 gene amplification. In other embodiments, the methods herein assess either or both of the FGFR2IIIb expression and FGFR2 gene amplification status before treatment is given, for example, to determine whether treatment with an anti-FGFR2-IIIb antibody is warranted. In some embodiments, the methods herein are used to treat gastric cancer which has been determined (a) to overexpress FGFR2-IIIb as indicated by an IHC signal of 2+ or 3+ in at least 10% of tumor cells and/or (b) to have FGFR2 gene amplification in ctDNA. In some embodiments, the methods herein are used to treat gastric cancer which has been determined (a) to overexpress FGFR2-IIIb as indicated by an IHC signal of 3+ in at least 10% of tumor cells and/or (b) to have FGFR2 gene amplification in ctDNA.

Routes of Administration, Carriers, and Additional Pharmaceutical Compositions

In various embodiments, antibodies may be administered in vivo by various routes, including, but not limited to, oral, intra-arterial, parenteral, intranasal, intravenous, intramuscular, intracardiac, intraventricular, intratracheal, buccal, rectal, intraperitoneal, intradermal, topical, transdermal, and intrathecal, or otherwise by implantation or inhalation. The subject antibodies may be formulated into preparations in solid, semi-solid, liquid, or gaseous forms; including, but not limited to, tablets, capsules, powders, granules, ointments, solutions, suppositories, enemas, injections, inhalants, and aerosols. A nucleic acid molecule encoding an antibody may be coated onto gold microparticles and delivered intradermally by a particle bombardment device, or "gene gun," as described in the literature (see, e.g., Tang et al., *Nature* 356:152-154 (1992)). The appropriate formulation and route of administration may be selected according to the intended application.

In various embodiments, compositions comprising antibodies are provided in formulations with a wide variety of pharmaceutically acceptable carriers (see, e.g., Gennaro, *Remington: The Science and Practice of Pharmacy with Facts and Comparisons: Drugfacts Plus*, 20$^{th}$ ed. (2003); Ansel et al., *Pharmaceutical Dosage Forms and Drug Delivery Systems*, 7$^{th}$ ed., Lippencott Williams and Wilkins (2004); Kibbe et al., *Handbook of Pharmaceutical Excipients*, 3$^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

Compositions comprising an anti-FGFR2 antibody as described herein and one or more of the chemotherapy agents of mFOLFOX 6, oxaliplatin, leucovorin, and 5-FU, as described herein, are also provided herein. In some embodiments, the FGFR2 inhibitor and the chemotherapy agents are each comprised within separate containers or within separate compartments of a single container, for example, such that they are not mixed together. In some embodiments, the compositions comprise instructions for use, such as instructions for use in cancer treatment.

EXAMPLES

The examples discussed below are intended to be purely exemplary of the invention and should not be considered to limit the invention in any way. The examples are not intended to represent that the experiments below are all or the only experiments performed.

Example 1: A Phase 3, Randomized, Double-Blind, Placebo-Controlled Study of an Anti-FGFR2-IIIb Antibody in Combination with Modified FOLFOX6 in Patients with Previously Untreated Advanced Gastric or Gastroesophageal Cancer, Preceded by a Phase 1 Dose-Finding, Safety Run-in Phase Protocol Synopsis The following protocol will be run at up to 250 different study centers globally. The study will be conducted tin two parts, part 1: the Phase 1 dose-finding, safety run-in phase, and part 2: the Phase 3 study.

The primary objectives of Part 1 are: (a) to determine the recommended dose (RD) of anti-FGFR2-IIIb when given in combination with a fixed dose of infusional 5-fluorouracil, leucovorin, and oxaliplatin (mFOLFOX6) in patients with advanced gastrointestinal (GI) tumors, and (b) to evaluate the safety profile of escalating doses of anti-FGFR2-IIIb when given in combination with mFOLFOX6 in patients with GI tumors. The secondary objectives of Part 1 are: (a) to evaluate the safety and tolerability of longer term exposure to anti-FGFR2-IIIb when given in combination with mFOLFOX6 in patients with GI tumors, (b) to characterize the pharmacokinetic (PK) profile of anti-FGFR2-IIIb when given in combination with mFOLFOX6 in patients with GI tumors, and (c) to characterize the immunogenicity of anti-FGFR2-IIIb. Part 1 will also characterize the pharmacodynamic (PD) profile of anti-FGFR2-IIIb, when given in combination with mFOLFOX6, through evaluation of exploratory biomarkers in blood and hair follicle samples from patients with GI tumors.

The primary end-point for part I will be: incidence of Grade 2 or higher adverse events (AEs) assessed as related to anti-FGFR2-IIIb by the Investigator and clinical laboratory abnormalities defined as dose-limiting toxicities (DLTs). The secondary end-points for part 1 will be: (a) incidence of AEs, clinical laboratory abnormalities, corneal and retinal findings, and electrocardiogram (ECG) abnormalities, (b) PK parameters of anti-FGFR2-IIIb, such as area under serum concentration-time curve (AUC), maximum serum concentration ($C_{max}$), trough serum concentration ($C_{trough}$), clearance (CL), terminal half-life ($t_{1/2}$), volume of distribution, and accumulation ratio, will be derived from the serum concentration-time profiles when appropriate and applicable, and (c) immune response against anti-FGFR2-IIIb as determined by immunogenicity testing. This part may also explore biomarkers in blood and hair follicle samples.

In Part 2, the primary objective is to evaluate the clinical benefit of anti-FGFR2-IIIb, when given in combination with mFOLFOX6 compared to placebo and mFOLFOX6, through analysis of progression-free survival (PFS) in patients with FGFR2b-selected gastric or gastroesophageal cancer (hereafter referred to as gastric cancer or GC). The secondary objectives are (a) to evaluate the clinical benefit of anti-FGFR2-IIIb, when given in combination with mFOLFOX6 compared to placebo and mFOLFOX6, through analysis of overall survival (OS) in patients with FGFR2b-selected GC, (b) to evaluate the safety and tolerability of anti-FGFR2-IIIb when given in combination with mFOLFOX6 compared to placebo and mFOLFOX6 in patients with FGFR2b-selected GC, (c) to characterize the PK profile of anti-FGFR2-IIIb when given in combination with mFOLFOX6 in patients with FGFR2b-selected GC, (d) characterize the immunogenicity of anti-FGFR2-IIIb, and (e) to characterize the PD profile of anti-FGFR2-IIIb, when given in combination with mFOLFOX6 compared to placebo and mFOLFOX6, through analysis of the immune cell infiltrate and other exploratory biomarkers in pre-treatment and on-treatment tumor biopsies. The study may also (a) evaluate the clinical benefit of anti-FGFR2-nib, when given in combination with mFOLFOX6 compared to placebo and mFOLFOX6, through analysis of PFS based on Blinded Independent Review Committee (BIRC) assessment of progression, (b) evaluate the clinical benefit of anti-FGFR2-IIIb, when given in combination with mFOLFOX6 compared to placebo and mFOLFOX6, through analysis of objective response rate (ORR) in patients with FGFR2b selected GC, (c) evaluate the clinical benefit of anti-FGFR2-IIIb, when given in combination with mFOLFOX6 compared to placebo and mFOLFOX6, through analysis of ORR based on BIRC assessment of progression, (d) evaluate the clinical benefit of anti-FGFR2-IIIb, when given in combination with mFOLFOX6 compared to placebo and mFOLFOX6, through analysis of one year OS in patients with FGFR2b-selected GC, (e) evaluate the clinical benefit of anti-FGFR2-IIIb, when given in combination with mFOLFOX6 compared to placebo and mFOLFOX6, through analysis of duration of response (DOR) in patients with FGFR2b-selected GC, (f) explore the association between FGFR2 status (in tumor tissue and/or blood-based biopsy [ctDNA] assay) with clinical outcome, (g) explore the concordance between FGFR2 status in tumor tissue and FGFR2 amplification using a blood-based biopsy (ctDNA) assay, (h) characterize the PD profile of anti-FGFR2-IIIb, when given in combination with mFOLFOX6 compared to placebo and mFOLFOX6, through evaluation of exploratory biomarkers in blood samples from patients with FGFR2b-selected GC, and (i) assess patient reported outcomes (PROs) and quality of life (QOL) outcomes in patients with FGFR2b-selected GC receiving anti-FGFR2-IIIb when given in combination with mFOLFOX6 compared to placebo and mFOLFOX6.

The endpoints for Part 2 include the primary end-point PFS, defined as time from randomization until the date of radiologically progressive disease based on Investigator assessment (per RECIST v.1.1) or death from any cause, whichever comes first, and various secondary endpoints. Secondary endpoints include: (a) OS, defined as time from randomization date until death from any cause, (b) objective response based on Investigator assessment of tumor lesions per RECIST v1.1, (c) incidence of AEs, clinical laboratory abnormalities, corneal and retinal findings, and ECG abnormalities, (d) PK parameters of anti-FGFR2-IIIb at the RD when administered in combination with mFOLFOX6, such as AUC, $C_{max}$, $C_{trough}$, CL, $t_{1/2}$, volume of distribution, and accumulation ratio, will be derived from the serum concentration-time profiles when appropriate and applicable, (e) immune response as determined by immunogenicity testing, and (f) levels of immune cell infiltrate and other exploratory biomarkers in pre-treatment and on-treatment tumor biopsy samples. The study may also evaluate: (a) one year OS, defined as the proportion of patients who receive at least one dose of anti-FGFR2-IIIb and are alive one year later, (b) DOR limited to patients with a response as determined by the Investigator per RECIST v1.1 and defined as the time of first response as determined by the Investigator per RECIST v1.1 to progression or death, whichever comes first, (c) correlation between identified FGFR2 status in tumor tissue and/or blood-based biopsy (ctDNA) assay and objective response per RECIST v1.1, (d) correlation between identified FGFR2 status in tumor tissue and FGFR2 amplification in blood-based biopsy (ctDNA) assay, (e) exploratory blood-based biomarkers, and (f) change from baseline in QoL as measured by EQ-5D-5L and the EORTC QLQ-C30.

The study design is as follows. The study is a 2-part, multicenter study to evaluate the safety, tolerability, PK, PD, and efficacy of anti-FGFR2-IIIb when given in combination with mFOLFOX6. The study will include an open-label, Part 1 dose escalation and a randomized, double-blind, placebo-controlled, Part 2 study in patients with FGFR2b+ gastric cancer. Part 1 consists of a minimum of 2 planned dosing cohorts of anti-FGFR2-IIIb in combination with mFOLFOX6 in eligible patients with advanced GI tumors to determine the RD of anti-FGFR2-IIIb to be administered in combination with mFOLFOX6. Part 2 consists of two expansion arms (1:1 randomization) with the aim of evaluating the safety and efficacy of anti-FGFR2-IIIb at the RD in combination with mFOLFOX6 compared to placebo and mFOLFOX6 in patients with FGFR2b-selected advanced GC (as determined by prospective immunohistochemistry (IHC) analysis of FGFR2b expression and/or a blood-based assay demonstrating FGFR2 amplification). Patients will be enrolled into either Part 1 or Part 2 of the study, but not both. After an initial screening period of up to 14 days (2 weeks), patients will be treated with mFOLFOX6 (with or without anti-FGFR2-IIIb) every 2 weeks in 14-day cycles. Patients may have initiated or received mFOLFOX6 chemotherapy prior to enrollment into Part 1, but eligibility requires that the patient be a candidate to receive at least 2 additional cycles of mFOLFOX6 chemotherapy (there is no upper limit on the number of FOLFOX cycles patients in Part 1 may have received, or they may not have received any). Each patient enrolled into Part 1 will be observed for 28 days for safety assessments and occurrence of dose-limiting toxicities (DLT Period). Upon completion of the DLT Period, patients may continue receiving anti-FGFR2-IIIb in combination with mFOLFOX6 at the Investigator's discretion. Additional treatments may be administered every 2 weeks in 14-day cycles until Investigator-assessed radiographic or clinical disease progression, unacceptable toxicity, or until the patient meets any of the other protocol-specified withdrawal criteria. There is no maximum number of doses of anti-FGFR2-IIIb. Ongoing administration of the mFOLFOX6 regimen beyond the DLT Period will be according to regional standard of care. In Part 2, patients whose tumor is positive for FGFR2b by IHC (score of 2+ or 3+) or blood, have completed 2 cycles of mFOLFOX6 chemotherapy as standard first line therapy for advanced stage gastric cancer, and have signed the informed consent, will be randomized 1:1 to be treated with anti-FGFR2-IIIb in combination with mFOLFOX6 or placebo and mFOLFOX6 every 2 weeks in 14-day cycles at an RD selected after assessment of data obtained in Part 1. Enrolled patients may continue treatment every 2 weeks in 14-day cycles until Investigator-assessed radiographic or clinical disease progression, unacceptable toxicity, or until the patient meets any of the other protocol-specified withdrawal criteria. All treatment decisions will be made by the Investigator using local assessments. After discontinuation of study treatment for reasons other than progression or withdrawal of consent, tumor assessments will continue until the patient initiates additional anti-cancer therapy. In addition, patients in both Part 1 and Part 2 will undergo long-term follow-up for survival by clinic visit or by telephone approximately every 3 months±28 days after the EOT visit until up to 24 months after the last patient is enrolled into the study, or until death, loss to follow-up, withdrawal of consent or study termination by the Sponsor (whichever occurs first).

Part 1 is an open-label dose-escalation study of anti-FGFR2-IIIb given in combination with mFOLFOX6. Patients eligible for Part 1 have unselected GI cancer (with or without FGFR2b overexpressing tumors) with unresectable, locally advanced, or metastatic disease, and are candidates to receive both anti-FGFR2-IIIb and mFOLFOX6 chemotherapy. FGFR2 status will be determined retrospectively by IHC and blood-based biopsy (ctDNA) assay. Patients enrolled into Part 1 will be treated with escalating doses of anti-FGFR2-IIIb in combination with a fixed-dose backbone chemotherapy regimen of mFOLFOX6 every 2 weeks in 14-day cycles, as follows:

Anti-FGFR2-IIIb Administration: anti-FGFR2-IIIb IV is administered every 2 weeks on Day 1 of each cycle prior to administration of mFOLFOX6 chemotherapy. Anti-FGFR2-IIIb will be administered as an approximately 30 minute IV infusion via a peripheral vein or central venous catheter with in-line filter.

Backbone Chemotherapy Regimen: Administration of mFOLFOX6 chemotherapy will commence on Day 1 of each treatment cycle and after administration of anti-FGFR2-IIIb (following a 30-minute rest). The mFOLFOX6 regimen is administered every 2 weeks as follows: oxaliplatin 85 mg/m$^2$ IV infusion over 120 minutes, leucovorin 400 mg/m$^2$ IV infusion over 120 minutes, followed by fluorouracil (5 FU) 400 mg/m$^2$ IV bolus, followed by 5-FU 2400 mg/m$^2$ as a continuous IV infusion over 46 hours. The administration of oxaliplatin does not require pre-hydration. Premedication with anti-emetics, such as serotonin antagonists with or without dexamethasone, may be used where clinically indicated at the discretion of the Investigator per local standard of care. Dose Levels (Part 1) In Part 1, two dose cohorts of anti-FGFR2-IIIb are anticipated in a standard 3+3 dose escalation design, with a minimum of 3 patients enrolled into each cohort. The anticipated dose levels are: Dose level 1:10 mg/kg anti-FGFR2-IIIb, Dose level 2: 15 mg/kg anti-FGFR2-IIIb Dose level-1: 6 mg/kg anti-FGFR2-IIIb (only if dose reduction is required from Dose Level 1).

All dose escalation decisions will be based on an assessment of DLTs, overall safety, and tolerability, and will be made after the last patient enrolled in each cohort has completed the 28-day DLT Period (completion of 2 treatment cycles). Dose escalation decisions will be agreed upon by the Cohort Review Committee (CRC), consisting of the Sponsor and Investigators. Review of safety and PK parameters may inform decisions to add cohorts with alternative dose levels in order to reach an optimal target exposure. Dose Level-1 will only be enrolled if ≥2 DLTs are observed at Dose Level 1. DLTs are defined below.

Dose escalation decisions will be based on the following algorithm: if none of the 3 patients in a cohort have DLTs, the next cohort may be opened; if 1/3 patients in a cohort shows DLTs, enroll 3 more patients in the same cohort; if 2/3 or 3/3 patients in a cohort show DLTs, stop enrollment and enter 3 more patients in cohort below (i.e. at the lower dose level) of only 3 had been in the previous cohort, if 1/6 patients in a cohort show DLTs, open the next cohort, and if 2/6 or greater show DLTs, stop enrollment and enter 3 more patients at the dose level below if only 3 patients had ben entered n that cohort.

The RD of anti-FGFR2-IIIb for Part 2 will be identified by the CRC based on an evaluation of the overall safety, tolerability, and PK. The RD, therefore, may or may not be the same as the identified maximum tolerated dose (MTD). For example, if the MTD is not reached, or if data from subsequent cycles of treatment from Part 1 provide additional insight on the safety profile, then the RD may be a different, though not higher, dose than the MTD. The MTD is defined as the maximum dose at which <33% of patients experience a DLT during the DLT Period. If a DLT is observed in 1 of 3 patients at a given dose level, then 3 additional patients will be enrolled at that same dose level. Dose escalation may continue until 2 of 3 to 6 patients treated at a dose level experience a DLT (dose level not to exceed 15 mg/kg). The next lower dose will then be considered the MTD. Once the MTD or RD has been reached, up to 6 additional patients will be added, to further explore the safety and PK at this dose level. The total enrollment for Part 1 will, therefore, be approximately 9 to 12 patients. Any patient who does not receive 2 doses of anti-FGFR2-IIIb in combination with mFOLFOX6 during the DLT Period will be considered unevaluable and the patient will be replaced. The replaced patient may continue on study after discussion with the Sponsor. No more than 2 doses of anti-FGFR2-IIIb or 2 cycles of mFOLFOX6 should be administered during the 28-day DLT Period. On completion of the DLT Period, patients may continue receiving anti-FGFR2-IIIb in combination with mFOLFOX6, administered every 2 weeks in 14-day cycles until Investigator-assessed radiographic or clinical disease progression, unacceptable toxicity, or until the patient meets any of the other protocol-specified withdrawal criteria. Dose modification criteria for anti-FGFR2-IIIb and mFOLFOX6 are described below. In the case of discontinuation of mFOLFOX6 chemotherapy administration for any reason prior to disease progression (e.g., cumulative toxicity or completion of mFOLFOX6 chemotherapy per regional practice), anti-FGFR2-IIIb may be continued as monotherapy and administered every 2 weeks until Investigator-assessed radiographic or clinical disease progression, unacceptable toxicity, or until the patient meets any of the other protocol-specified withdrawal criteria. In the event a cycle of mFOLFOX6 is delayed beyond 14 days due to chemotherapy-related toxicity, anti-FGFR2-IIIb administration should not be delayed and may continue to be administered every 2 weeks. Initiation of a new cycle of mFOLFOX6 following a dosing delay should be synchronized with administration of an anti-FGFR2-IIIb infusion where possible (but is not a study requirement).

In the case of discontinuation of anti-FGFR2-IIIb for any reason prior to disease progression (e.g., cumulative toxicity), mFOLFOX6 chemotherapy may continue to be administered in accordance with local regional practice, or until Investigator-assessed radiographic or clinical disease progression, unacceptable toxicity, or the patient meets any of the other protocol-specified withdrawal criteria Patients will be enrolled into Part 2 with the objective of characterizing the safety and efficacy of anti-FGFR2-IIIb combined with mFOLFOX6 compared to placebo and mFOLFOX6 in an FGFR2b-selected gastric cancer patient population. Enrollment into Part 2 will begin only once an RD for anti-FGFR2-IIIb, which will not exceed 15 mg/kg, has been identified by the CRC in Part 1. Part 2 is double-blind and will consist of a total of up to approximately 360 FGFR2b-selected gastric cancer patients randomized 1:1 to receive one of two treatment arms: Arm 1: anti-FGFR2-IIIb at the RD and mFOLFOX6 administered every 2 weeks, or Arm 2: Placebo and mFOLFOX6 administered every 2 weeks. Opening of Part 2 for enrollment will be at the discretion of the Sponsor. Patients with gastric cancer with unresectable, locally advanced, or metastatic disease who are eligible for first-line mFOLFOX6 chemotherapy and have received 2 cycles of mFOLFOX6 will be enrolled into Part 2 of the study. Patients will be selected for enrollment based on FGFR2b overexpression and/or FGFR2 amplification, as determined by a validated IHC or blood-based biopsy (ctDNA) assay, respectively. Patients who do not demonstrate either FGFR2b overexpression using IHC or amplification using a blood-based biopsy (ctDNA) assay will not be eligible for enrollment; however, positivity based on one or both of the assays is adequate to meet eligibility requirements (e.g., positive by blood-based biopsy [ctDNA] assay, but negative by IHC). Enrolled patients may continue treatment every 2 weeks in 14-day cycles until Investigator-assessed radiographic or clinical disease progression, unacceptable toxicity, or until the patient meets any of the other protocol-specified withdrawal criteria. All treatment decisions will be made by the Investigator using local.

The inclusion criteria are as follows. Patients enrolling into either Part 1 or Part 2 of the study must be ≥18 years of age; have disease that is unresectable, locally advanced, or metastatic; Eastern Cooperative Oncology Group (ECOG) performance status of 0 to 1; must provide tumor tissue for determination of FGFR2 status; provide informed consent; and satisfy all other eligibility criteria described below. Patients enrolling into Part 1 (Dose-Escalation Safety Run-in) of the study must also meet the following inclusion criteria: Histologically or cytologically confirmed gastrointestinal malignancy for which mFOLFOX6 is considered an appropriate treatment (e.g., gastric cancer, colorectal carcinoma, pancreatic adenocarcinoma). No more than 2 prior chemotherapy regimens for metastatic disease (not including prior adjuvant chemotherapy with 5-FU and/or oxaliplatin). Patient must be a candidate for at least 2 cycles of mFOLFOX6 chemotherapy.

Patients enrolling into Part 2 (Dose-Expansion) of the study must also meet the following inclusion criteria: Histologically documented gastric or gastroesophageal junction adenocarcinoma. FGFR2b overexpression as determined by IHC and/or FGFR2 amplification as determined by blood-based biopsy (ctDNA) assay. No prior chemotherapy for metastatic or unresectable disease (except as noted in Inclusion Criteria #20 for mFOLFOX6). No prior platinum-based chemotherapy (except as noted in Inclusion Criteria #20 for mFOLFOX6). If prior adjuvant or neo-adjuvant therapy (chemotherapy and/or chemoradiation) has been received, more than 6 months must have elapsed between the end of adjuvant therapy and enrollment.

A patient must be a candidate for mFOLFOX6 chemotherapy and have received 2 cycles of mFOLFOX6 chemotherapy prior to study enrollment (but not to exceed 2 cycles). Patients enrolling into either Part 1 or Part 2 will be excluded if they have untreated or symptomatic central nervous system (CNS) metastases; impaired cardiac function or clinically significant cardiac disease; elevated QTcF; peripheral sensory neuropathy≥Common Terminology Criteria for Adverse Events (CTCAE) grade 2; positive HER2 status; or other condition that may increase the risk associated with study participation. No waivers of these inclusion or exclusion criteria will be granted.

In Part 1, anti-FGFR2-IIIb will be supplied in a sterile vial for dilution into an intravenous bag for administration by the study site over approximately 30 minutes every 14 days (+/−3 days) until Investigator-assessed radiographic or clinical disease progression, unacceptable toxicity, or other cause for protocol-specified study withdrawal.

In Part 2, blinded IP (anti-FGFR2-IIIb/placebo) will be supplied and administered in a similar fashion to open-label anti-FGFR2-IIIb in Part 1.

Oxaliplatin, 5-FU, and leucovorin will be supplied to each site as per routine institutional practice. The mFOLFOX6 regimen will be administered every 14 days (+/−3 days) until Investigator-assessed radiographic or clinical disease progression, unacceptable toxicity, or other cause for protocol-specified study withdrawal. Refer to the most current regional package insert for preparation and complete prescribing information.

Blood samples will be collected to evaluate PK parameters of anti-FGFR2-IIIb, such as AUC, $C_{max}$, $C_{trough}$, CL, $t_{1/2}$, volume of distribution, and accumulation ratio. In Part 1, blood samples will be collected at the time points outlined below to measure serum levels of anti-FGFR2-IIIb in all enrolled patients. In Part 2, blood samples will be collected for the first 60 patients randomized into Part 2 at the time points outlined below. For Part 1 and Part 2, blood samples for anti-anti-FGFR2-IIIb antibodies will be collected at the timepoints specified.

Tumor response assessment will be performed both by the Investigator and by blinded central radiology review per RECIST v.1.1 guidelines. Full details around independent review by a BIRC will be listed in an Independent Imaging Review Charter.

Efficacy measures will include tumor assessments consisting of clinical examination and appropriate imaging techniques, preferably computed tomography (CT) scans of the chest, abdomen, and pelvis with appropriate slice thickness per RECIST guidelines; other assessments (magnetic resonance imaging [MiII], X ray, positron emission tomography [PET], and ultrasound) may be performed, if required. Tumor assessments will be performed at Screening (within 2 weeks of Cycle 1 Day 1 in Part 1 and Part 2), then every 6 weeks from the first dose, for 24 weeks, and then approximately every 12 weeks thereafter. Once an initial complete response (CR) or partial response (PR) is noted, confirmatory scans must be performed 4 to 6 weeks later.

Safety measures will include AEs, hematology, clinical chemistry, urinalysis, vital signs, body weight, concomitant medications/procedures, ECOG performance status, targeted physical examinations, ECGs, and ophthalmology examinations. An independent Data Monitoring Committee (DMC) will evaluate safety study data (AE and SAEs) on a regular basis throughout the entire treatment phase in Part 2.

In Part 1: Tumor tissue submitted for evaluation of FGFR2 status will be retrospectively analyzed for FGFR2b overexpression using IHC. Samples for blood-based biopsy (ctDNA) assay will be collected prior to the first dose of study drug (Cycle 1 Day 1) and analyzed retrospectively for FGFR2 amplification. Blood samples for exploratory biomarker analysis will be collected prior to dosing on Day 1 of Cycles 1 and 2, at 48 hours following the Cycle 1 Day 1 and Cycle 2 Day 1 doses (Day 3), prior to dosing on Cycle 3 Day 1 for patients who continue treatment beyond the 28-day DLT Period, and at the EOT visit. Hair follicle samples will be collected prior to dosing on Cycle 1 Day 1, Cycle 3 Day 1, and Cycle 5 Day 1, and at the EOT visit from all patients for whom sampling is possible.

In Part 2: Tumor tissue will be submitted for evaluation of FGFR2 status and will be prospectively analyzed for FGFR2b overexpression using IHC. Blood samples for ctDNA assessment will be analyzed prospectively for FGFR2 amplification. In addition, blood-based biopsy (ctDNA) assays will be collected longitudinally every 6 weeks from the first dose for 24 weeks, and then approximately every 12 weeks thereafter, and analyzed retrospectively for FGFR2 amplification. A sample will also be collected at the EOT visit for all Part 2 patients. A sample will also be collected at the EOT visit for all Part 2 patients. Blood samples for exploratory biomarker analysis will be collected prior to dosing on Day 1 of Cycles 1 and 2, at 48 hours following the Cycle 1 Day 1 and Cycle 2 Day 1 doses (Day 3), prior to dosing on Cycle 3 Day 1, and at the EOT visit.

Fresh tumor biopsies, mandatory as feasible, will be performed before treatment and on-treatment within 7 days prior to Cycle 3 Day 1 (and at least 24 hours prior to dosing) for up to 30 patients randomized into Part 2. Feasibility at each time point will be assessed by the Investigator and should include a consideration of patient safety. If the Investigator assesses that a biopsy is not feasible, then this determination must be recorded in the source documents. For patients who have had a biopsy acquired within 12 weeks prior to enrollment, that sample may fulfill the requirement for a fresh pre-treatment biopsy provided adequate sample is available for PD analysis (a single paraffin-embedded block or approximately 10 slides). Patients in Part 2 may also have an optional on-treatment biopsy upon documented tumor response and/or optional post-treatment biopsy upon documented tumor progression after discussion with the Sponsor.

The total enrollment planned for this study is up to approximately 372 patients. Up to approximately 12 patients evaluable for any dose limiting toxicity, per standard 3+3 design, will be enrolled into Part 1. For Part 2, efficacy and tolerability will be examined by enrollment of up to approximately 360 patients with FGFR2b-selected gastric cancer, randomized 1:1 to receive anti-FGFR2-IIIb in combination with mFOLFOX6 or placebo and mFOLFOX6. Eligible patients will be stratified according to geographic region (US and EU vs Asia vs Rest of World), prior treatment status (de novo vs adjuvant/neo-adjuvant), and measurable disease status (measurable vs non-measurable).

In Part 1, all analyses will be descriptive and will be presented by dose group and overall as appropriate. Descriptive statistics will include number of observations, mean, standard deviation, median, range, and inter-quartile range for continuous variables, and the number and percent for categorical variables; 95% confidence intervals will be presented where appropriate. In Part 2, the primary efficacy analysis is the comparison of PFS in patients treated with anti-FGFR2-IIIb in combination with mFOLFOX6 or placebo and mFOLFOX6. The primary endpoint, PFS, is defined as time from randomization until the date of radiologically progressive disease based on Investigator assessment (per RECIST v.1.1) or death from any cause, whichever comes first. The secondary efficacy endpoints include OS and ORR. There will be an interim analysis and primary analysis for PFS and both are event-based analyses. Only futility test of PFS will be conducted at the interim analysis after 48 events (50% of target 96 PFS events for primary analysis of PFS) observed in the enrolled patients to exclude HR >0.806 for the combination of anti-FGFR2-IIIb and mFOLFOX6 compared with placebo and mFOLFOX6. It is estimated that the interim analysis will occur approximately 20 months from the 1st patient enrolled. The primary analysis of PFS will be conducted when at least 96 PFS events have been observed in the first 156 enrolled patients, and will be performed using the intent-to-treat (ITT) population. The primary analysis will include only radiographic progression events as determined by the Investigator per RECIST V.1.1 and deaths. The primary analysis of PFS will be conducted using a stratified log-rank 2-sided test with a 0.05 level of significance. The stratification factors will be the same used to stratify the randomization schedule as documented in the interactive voice and Web response system (IXRS). If the p-value for the stratified log-rank test is statistically significant (<0.05 two-sided) and the HR is <1, the null hypothesis of no difference in PFS will be rejected and it will be inferred that PFS is statistically prolonged in the group receiving anti-FGFR2-IIIb in combination with mFOLFOX6 compared with the group receiving placebo and mFOLFOX6. The median PFS and the associated 95% confidence interval for each treatment arm will be estimated using the Kaplan-Meier method. The hazard ratio ($HR = \lambda_{anti\text{-}FGFR2\text{-}IIIb+\ mFOLFOX6} / \lambda_{mFOLFOX6}$) will be estimated using a Cox regression model with treatment group as the only main effect and stratifying by the same stratification factors as were used for the log-rank test. An unstratified HR will also be presented.

Analyses of secondary endpoints including OS and ORR will be conducted when the primary endpoint, PFS, is statistically significant, and formal hypotheses of OS and ORR will be tested hierarchically at a level of 0.05. The OS will be tested first and if it is significant, the ORR will be tested next. The type I error rate of testing primary and secondary endpoints will be in a control by employing this fixed-sequence testing procedure at a level of 0.05. There will be an interim and final analysis for OS planned if the test for PFS is statistically significant. The interim analysis of OS will be conducted at the time of primary analysis of PFS. Should OS be analyzed, analysis of OS at the interim (i.e., when at least 96 PFS events have been observed), and at the end (i.e., when 249 deaths have been observed) will be performed on the ITT population. The hypothesis testing of OS will be conducted using a stratified log-rank 2-sided test with a 0.05 level of significance. The group sequential method will be used to allocate type I error rate based on O'Brien-Fleming boundary and type II error rate based on the Gamma family with parameter −4 at the interim and final analysis of OS. The stratification factors will be the same used to stratify the randomization schedule as documented in the IXRS. The median OS and the associated 95% confidence interval for each treatment arm will be estimated using the Kaplan-Meier method. The HR will be estimated using a Cox regression model with treatment group as the only main effect and stratifying by the same stratification factors as were used for the log-rank test. An unstratified HR will also be presented. The ORR is defined as the proportion of patients with partial or complete response as defined by the Investigator per RECIST v.1.1. The primary analysis of ORR will be performed among the patients with baseline measurable disease. In the analysis of ORR, patients who do not have any post-baseline adequate tumor assessments will be counted as non-responders. Formal hypothesis testing of ORR will be performed using the stratified Cochran-Mantel-Haenszel test. The stratification factors will be the same used to stratify the randomization schedule as documented in the IXRS.

Power and Sample Size: This study is designed to provide adequate power for primary analysis of PFS. Based on a median PFS (mPFS) for patients receiving placebo and mFOLFOX6 of 6 months, approximately 156 patients (randomized 1:1) with a target of 96 PFS events are required to demonstrate a hazard ratio (HR) of 0.5 for mPFS with a power of 90% (2-sided $\alpha=0.05$) for the combination of anti-FGFR2-IIIb and mFOLFOX6 compared with placebo and mFOLFOX6 after 24 months of accrual and 6 months of follow up. Assuming an exponential distribution of PFS, this corresponds to an increase in mPFS from 6 months to 12 months. In the current design, the minimum observed effect that would result in statistical significance for PFS is a 50% improvement (HR=0.67) from 6 to 9 months. This study is also powered for primary analysis of OS. Based on a median OS (mOS) for patients receiving placebo and mFOLFOX6 of 10 months, enrollment of the study will continue to up to approximately 360 patients with a target of 249 death events to demonstrate an HR of 0.7 for mOS with a power of 80% at the overall type I error level of 0.05 for the combination of anti-FGFR2-IIIb and mFOLFOX6 compared to placebo and mFOLFOX6 after 36 months of accrual and 10 months of follow-up after enrollment of the last patient. Assuming an exponential distribution of OS, this corresponds to an increase of 43% in median OS from 10 months to 14.3 months. In the current design, the minimum observed effect that would result in statistical significance for OS at the final analysis is a 28% improvement (HR=0.78) from 10 to 12.8 months.

Safety Analysis: The analyses of safety will include all patients who receive any study drug (anti-FGFR2-IIIb and mFOLFOX6 or placebo and mFOLFOX6) throughout the study duration and provide any post-treatment safety information. All AEs will be coded using the Medical Dictionary for Regulatory Activities (MedDRA). The Investigator will classify the severity of AEs using the CTCAE v 4.03. A treatment emergent adverse event (TEAE) is defined as any event with an onset date on or after date of first dose of study drug, or any event present before treatment that worsens after treatment. Only TEAEs with an onset date prior to date of last dose+30 days will be tabulated in summary tables. The number and percentage of patients who experience AEs will be summarized by system organ class, preferred term, relationship to study drug, and severity for each treatment group. A by-patient listing will be provided for those patients who experience an SAE, including death, or experience an AE associated with early withdrawal from the study or discontinuation from study drug. Clinical laboratory data will be summarized by the type of laboratory test. The number and percentage of patients who experience abnormal (ie, outside of reference ranges) and/or clinically significant abnormalities after study drug administration will be presented for each clinical laboratory measurement. For each clinical laboratory measurement, descriptive statistics will be provided for baseline and all subsequent post-treatment scheduled visits. Changes from baseline to the posttreatment visits will also be provided. Descriptive statistics of vital signs will also be provided in a similar manner. In addition, shift from baseline in CTCAE grade (where applicable) and by high/low flags (where CTCAE grades are not defined) will be presented by treatment group. No formal comparisons of safety endpoints are planned.

PK Analysis: PK parameters will be estimated using non-compartmental analysis, though compartment analysis may be employed if appropriate.

Detailed Protocol

1. Introduction

Anti-FGFR2-IIIb Background

The role of the fibroblast growth factor (FGF) receptor (FGFR) pathway in cancer is well known. FGFs can stimulate the transformation and proliferation of tumor cells and stimulate angiogenesis. There are 22 known human FGFs with the expression of individual FGFs generally restricted to specific tissues, cell types, and/or developmental stage. FGF signaling is mediated by a family of transmembrane tyrosine kinase receptors encoded by four distinct genes producing FGF receptor subtypes termed FGFR1-4 (Turner and Grose 2010).

FGFR2 has two splicing variants, b and c. In general, FGFR2b is expressed in tissues of epithelial origin (e.g., stomach, skin) (Miki 1992). The major ligands signaling through FGFR2b are FGF7, FGF10 and FGF22. Alteration in signaling in the FGF/FGFR2 pathway (e.g., overexpression of FGFR2b protein or amplification of FGFR2 gene) has been associated with gastric, breast, and other cancers, and appears to portend a worse prognosis (Wu 2013, Turner and Grose 2010). In fact, as early as 1990, subsets of patients with gastric cancer (~3 to 9%) and breast cancer (1 to 2%) were noted to have amplification of the FGFR2 gene, which resides on chromosome 10q26. In gastric cancer, FGFR2 amplification leads to high-level expression of the FGR2b receptor on the surface of the cells.

An FGFR2b-Specific Antibody

Anti-FGFR2-IIIb is a humanized monoclonal antibody (IgG1 isotype) specific to the human FGFR2b receptor (NCBI reference sequence ID NP_001138385.1) that blocks FGF ligand binding to the receptor. Anti-FGFR2-IIIb is directed against the third Ig region of the FGFR2b receptor isoform, the region that is alternatively spliced and regulates ligand specificity. This antibody is glycosylated, but is produced in a Chinese hamster ovary (CHO) cell line that lacks the FUT8 gene (α1,6-Fucosyltransferase) and therefore lacks a core fucose in the polysaccharide portion of the antibody. The absence of the core fucose results in higher affinity for the Fc receptor FcγRIIIa compared to the fucosylated molecule and potentially enhances immune cell-mediated tumor cell killing (Shinkawa 2003). The antibody has thus been glycoengineered for enhanced antibody-dependent cell-mediated cytotoxicity (ADCC) (Gemo 2014). Anti-FGFR2-IIIb inhibits FGF ligand-stimulated FGFR2b phosphorylation and cell proliferation in cell culture in FGFR2b overexpressing gastric and breast cancer cell lines. Anti-FGFR2-IIIb also inhibits tumor growth in FGFR2b overexpressing gastric and breast xenograft models. The 3 potential mechanisms of action of anti-FGFR2-IIIb thus include blocking ligand binding and downstream signaling, decreasing expression of the FGFR2b driver protein, and enhancing ADCC.

Anti-FGFR2-IIIb can produce complete and durable tumor growth inhibition in FGFR2b-overexpressing and FGFR2 gene-amplified gastric cancer xenografts in immune-compromised mice where FGFR2b is considered a driver of tumor growth (Gemo 2014). In addition, anti-FGFR2-IIIb demonstrates recruitment of NK cells and concomitant tumor growth inhibition in the 4T1 syngeneic tumor model with modest expression of FGFR2b. These data suggest that ADCC may be efficacious in patients without FGFR2 gene amplification with moderate FGFR2b overexpression, and that ADCC activity may be a major contributor to the mechanism of action in these patients.

Additionally, since anti-FGFR2-IIIb is specific for the FGFR2b receptor, it does not interfere with signaling of the other FGFs/FGFRs, including FGFR2c. In contrast to the FGFR tyrosine kinase inhibitors (TKIs), anti-FGFR2-IIIb does not inhibit FGF23 signaling. FGF23 is a ligand involved in calcium/phosphate metabolism. Thus, treatment with anti-FGFR2-IIIb is not expected to cause significant dose-limiting hyperphosphatemia associated with the FGFR TKIs (Andre 2013, Brown 2005, Dienstmann 2014, Sequist 2014).

mFOLFOX6

Infusional 5-fluorouracil, leucovorin, and oxaliplatin (mFOLFOX6) is an approved chemotherapy agent and is a standard of care for first-line treatment of metastatic gastric cancer. 5-FU is the main chemotherapeutic agent used for the treatment of gastric cancer around the world and is frequently combined with other therapies after research showed improved clinical outcomes resulting from 5-FU combination chemotherapies (Keam 2008). The standard treatment, Adrucil® also known as 5-fluorouracil (5-FU), is a commonly used chemotherapeutic agent that is currently indicated to treat colorectal cancers, breast cancer, gastric cancer, and pancreatic cancer.

Anti-FGFR2-IIIb and mFOLFOX6 Starting Dose Justification

A starting dose of 10 mg/kg anti-FGFR2-IIIb administered as an IV infusion every 2 weeks in 28-day cycles is planned for Part 1 of this dose escalation safety run-in study. In the prior Phase I clinical study, dose escalation was performed in patients with solid tumors (n=19) and gastric cancer patients (n=8). During the dose escalation, there were no dose limiting toxicities (DLTs) at any dose level and therefore no maximum tolerated dose (MTD) of anti-FGFR2-IIIb was identified. The 15 mg/kg was chosen as the expansion dose based on preclinical modeling of target drug concentrations and observed tolerability as well as evidence of observed efficacy. At 15 mg/kg every 2 weeks dosing, it is expected to achieve anti-FGFR2-IIIb trough concentration at steady state ($C_{trough\ ss}$) of 60 μg/mL in majority of patients, which was derived from the mouse efficacy study using the OCUM2 FGFR2-amplified gastric cancer xenograft model.

Based on published data from population PK analyses, no clinically significant differences were observed in the PK by race for antibody therapeutics including bevacizumab (Genentech Inc.), trastuzumab (Genentech Inc.), pertuzumab (Genentech Inc. 2016), and ramucirumab (Eli Lilly and Company). Importantly, the clinical data from the ongoing anti-FGFR2-IIIb study supports that a 10 mg/kg dose is tolerable in humans. Anti-FGFR2-IIIb has also shown a tolerable safety profile in the first-in-human study, with 53 patients treated at doses up to 15 mg/kg.

The starting dose for mFOLFOX6 includes 85 mg/m$^2$ of oxaliplatin, 350 mg of calcium folinate (folinic acid), a 400-mg/m$^2$ dose of fluorouracil, and a 2400-mg/m$^2$ dose of fluorouracil. Oxaliplatin and calcium folinate are administered concomitantly via IV infusion using a 3-way tap/Y-site connector. The smaller dose of fluorouracil is administered via IV bolus, and the larger dose of fluorouracil is administered via IV infusion over the course of 46 hours. mFOLFOX6 is administered every 14 days.

Rationale for Part 2 Pre-Screening

Anti-FGFR2-IIIb is an antibody designed to recognize the FGFR2b receptor when expressed on gastric tumors. The current hypothesis is that the presence of FGFR2b will be an important predictor of how patients with FGFR2b-selected gastric or gastroesophageal cancer (in Part 2) will respond. This is based on the preclinical observation that only tumors that overexpressed FGFR2b responded to anti-FGFR2-IIIb treatment in xenograft studies), as well as early results from the ongoing first-in-human study indicating a higher degree of anti-FGFR2-IIIb activity in FGFR2b-positive patients.

Patients in Part 2 will be selected for enrollment based on FGFR2b overexpression and/or FGFR2 amplification, as determined by a validated IHC (score of 2+ or 3+) or blood-based biopsy assay, respectively. Patients who do not demonstrate either FGFR2b overexpression using IHC or amplification using a blood-based biopsy assay will not be eligible for enrollment; however, positivity based on one or both of the assays is adequate to meet eligibility requirements (e.g., positive by blood-based biopsy assay, but negative by IHC).

Patients in Part 2 will be naïve to prior chemotherapy for metastatic or unresectable disease; if prior adjuvant or neo-adjuvant therapy (chemotherapy and/or chemoradiation) has been received, more than 6 months must have elapsed between the end of adjuvant therapy and enrollment. These patients will have disease that is unresectable, locally advanced, or metastatic, and therefore are expected to begin treatment (mFOLFOX6) shortly after their diagnosis.

As the IHC results may require up to several weeks to complete, patients who are negative by the blood-based assay would face a delay in beginning their chemotherapy treatment while waiting for their eligibility to be confirmed by IHC. For this reason, all patients entering the study will be required to have received 2 cycles of mFOLFOX6 at the time of enrollment. Patients cannot have received more than 2 cycles or less than 2 cycles, as this could lead to an imbalance in treatment among study participants and potentially confound interpretation of the study results. It is anticipated that IHC results can be obtained during the time it will take to administer the first 2 cycles of mFOLFOX6. During this time, patients are not yet enrolled in the study, and thus mFOLFOX6 will be administered according to local practice, and adverse events are not to be recorded as part of the study. Patients will provide pre-screening informed consent for the blood and IHC assays. If the IHC results are positive, the patient would complete the second course of mFOLFOX6, enter the screening period, and if all other eligibility criteria are satisfied including providing informed consent, would then enroll into the study. If the IHC results are negative, and the blood-based biopsy was also negative, the patient is ineligible to participate in the study.

Rationale for Tumor Biopsy and Blood Assessments

Patients in Part 2 of this trial are required to have both a tissue result and a blood result; therefore, a patient is not eligible if they cannot provide both tissue and blood plasma. Patients who do not demonstrate either FGFR2b overexpression using IHC or amplification using a blood-based biopsy assay will not be eligible for enrollment; however, positivity based on one or both of the assays is adequate to meet eligibility requirements (e.g., positive by blood-based biopsy assay, but negative by IHC). The blood test will reveal DNA amplification of FGFR2, while the IHC test will show the extent of protein expression. Five Prime has developed an anti-FGFR2b antibody for nonclinical use, whose sensitivity and specificity to detect FGFR2b by IHC has been optimized.

In studies evaluating gastric cancer samples, FGFR2 amplification has been uniformly associated with significant FGFR2b surface expression, as detected by IHC (Gemo 2014). The antitumor effect of anti-FGFR2-IIIb that was observed in preclinical testing was predicated upon the overexpression of FGFR2b in the tumor cell lines. Patients without overexpression of FGFR2b are unlikely to see a significant benefit from treatment with anti-FGFR2-IIIb and mFOLFOX6. The selection of patients with FGFR2b-positive tumors for treatment with anti-FGFR2-IIIb is supported by data from the ongoing Phase 1, first-in-human study of anti-FGFR2-IIIb. Study Objectives and Endpoints Part 1: Primary Objectives To determine the recommended dose (RD) of anti-FGFR2-IIIb when given in combination with a fixed dose of infusional 5-fluorouracil, leucovorin, and oxaliplatin (mFOLFOX6) in patients with advanced gastrointestinal (GI) tumors.

To evaluate the safety profile of escalating doses of anti-FGFR2-IIIb when given in combination with mFOLFOX6 in patients with GI tumors.

Part 1: Secondary Objectives

To evaluate the safety and tolerability of longer term exposure to anti-FGFR2-IIIb when given in combination with mFOLFOX6 in patients with GI tumors.

To characterize the pharmacokinetic (PK) profile of anti-FGFR2-IIIb when given in combination with mFOLFOX6 in patients with GI tumors.

To characterize the immunogenicity of anti-FGFR2-IIIb.

Part 1: Exploratory Objectives

To characterize the pharmacodynamic (PD) profile of anti-FGFR2-IIIb, when given in combination with mFOLFOX6, through evaluation of exploratory biomarkers in blood and hair follicle samples from patients with GI tumors.

Part 2: Primary Objectives

To evaluate the clinical benefit of anti-FGFR2-IIIb, when given in combination with mFOLFOX6 compared to placebo and mFOLFOX6, through analysis of progression-free survival (PFS) in patients with FGFR2b-selected gastric or gastroesophageal cancer (hereafter referred to as gastric cancer or GC).

Part 2: Secondary Objectives

To evaluate the clinical benefit of anti-FGFR2-IIIb, when given in combination with mFOLFOX6 compared to placebo and mFOLFOX6, through analysis of overall survival (OS) in patients with FGFR2b-selected GC.

To evaluate the safety and tolerability of anti-FGFR2-IIIb when given in combination with mFOLFOX6 compared to placebo and mFOLFOX6 in patients with FGFR2b-selected GC.

To characterize the PK profile of anti-FGFR2-IIIb when given in combination with mFOLFOX6 in patients with FGFR2b-selected GC.

To characterize the immunogenicity of anti-FGFR2-IIIb.

To characterize the PD profile of anti-FGFR2-IIIb, when given in combination with mFOLFOX6 compared to placebo and mFOLFOX6, through analysis of the immune cell infiltrate and other exploratory biomarkers in pre-treatment and on-treatment tumor biopsies.

Part 2: Exploratory Objectives

To evaluate the clinical benefit of anti-FGFR2-IIIb, when given in combination with mFOLFOX6 compared to placebo and mFOLFOX6, through analysis of PFS based on Blinded Independent Review Committee (BIRC) assessment of progression.

To evaluate the clinical benefit of anti-FGFR2-IIIb, when given in combination with mFOLFOX6 compared to placebo and mFOLFOX6, through analysis of objective response rate (ORR) in patients with FGFR2b-selected GC.

To evaluate the clinical benefit of anti-FGFR2-IIIb, when given in combination with mFOLFOX6 compared to placebo and mFOLFOX6, through analysis of ORR based on BIRC assessment of progression.

To evaluate the clinical benefit of anti-FGFR2-IIIb, when given in combination with mFOLFOX6 compared to placebo and mFOLFOX6, through analysis of one year OS in patients with FGFR2b-selected GC.

To evaluate the clinical benefit of anti-FGFR2-IIIb, when given in combination with mFOLFOX6 compared to placebo and mFOLFOX6, through analysis of duration of response (DOR) in patients with FGFR2b-selected GC.

To explore the association between FGFR2 status (in tumor tissue and/or blood-based biopsy) with clinical outcome.

To explore the concordance between FGFR2 status in tumor tissue and FGFR2 amplification using a blood-based biopsy.

To characterize the PD profile of anti-FGFR2-IIIb, when given in combination with mFOLFOX6 compared to placebo and mFOLFOX6, through evaluation of exploratory biomarkers in blood samples from patients with FGFR2b-selected GC.

To assess patient reported outcomes (PROs) and quality of life (QOL) outcomes in patients with FGFR2b-selected GC receiving anti-FGFR2-IIIb when given in combination with mFOLFOX6 compared to placebo and mFOLFOX6.

Part 1: Primary Study Endpoints

The incidence of Grade 2 or higher adverse events (AEs) assessed as related to anti-FGFR2-IIIb by the Investigator and clinical laboratory abnormalities defined as dose-limiting toxicities (DLTs).

Part 1: Secondary Endpoints

The incidence of AEs, clinical laboratory abnormalities, corneal and retinal findings, and electrocardiogram (ECG) abnormalities.

PK parameters of anti-FGFR2-IIIb, such as area under serum concentration-time curve (AUC), maximum serum concentration (Cmax), trough serum concentration (Ctrough), clearance (CL), terminal half-life (t½), volume of distribution, and accumulation ratio, will be derived from the serum concentration-time profiles when appropriate and applicable.

To evaluate immune response as determined by immunogenicity testing.

Part 1: Exploratory Endpoints

Exploratory biomarkers in blood and hair follicle samples.

Part 2: Primary Endpoints

PFS, defined as time from randomization until the date of radiologically progressive disease based on Investigator assessment (per RECIST v.1.1) or death from any cause, whichever comes first.

Part 2: Secondary Endpoints

OS, defined as time from randomization date until death from any cause.

Objective response rate (ORR) based on Investigator assessment of tumor lesions per RECIST v1.1.

Incidence of AEs, clinical laboratory abnormalities, corneal and retinal findings, and electrocardiogram (ECG) abnormalities.

PK parameters of anti-FGFR2-IIIb at the RD when administered in combination with mFOLFOX6, such as AUC, Cmax, Ctrough, CL, t½, volume of distribution, and accumulation ratio, will be derived from the serum concentration-time profiles when appropriate and applicable.

Immune response as determined by immunogenicity testing.

Levels of immune cell infiltrate and other exploratory biomarkers in pre-treatment and on-treatment tumor biopsy samples.

Part 2: Exploratory Endpoints

One year OS, defined as the proportion of patients who receive at least one dose of anti-FGFR2-IIIb and are alive one year later.

DOR limited to patients with a response as determined by the Investigator per RECIST v1.1 and defined as the time of first response as determined by the Investigator per RECIST v1.1 to progression or death, whichever comes first.

The correlation between identified FGFR2 status in tumor tissue and/or blood-based biopsy and objective response per RECIST v1.1.

The correlation between identified FGFR2 status in tumor tissue and FGFR2 amplification in blood-based biopsy.

Exploratory Biomarkers in Blood Samples.

Change from baseline in QoL as measured by EQ-5D-5L and the EORTC QLQ-C30.

Overall Design and Plan of the Study

Overview

This is a 2-part, multicenter study to evaluate the safety, tolerability, PK, PD, and efficacy of anti-FGFR2-IIIb when given in combination with mFOLFOX6. The study will include an open-label, Part 1 dose escalation safety run-in and a randomized, double-blind, placebo-controlled, Part 2 dose expansion.

Part 1 consists of a minimum of 2 planned dosing cohorts of anti-FGFR2-IIIb in combination with mFOLFOX6 in eligible patients with advanced GI tumors to determine the RD of anti-FGFR2-IIIb to be administered in combination with mFOLFOX6. Part 2 consists of 2 expansion arms (1:1 randomization) with the aim of evaluating the safety and efficacy of anti-FGFR2-IIIb at the RD in combination with mFOLFOX6 compared to placebo and mFOLFOX6 in patients with FGFR2b-selected advanced GC (as determined by prospective IHC analysis of FGFR2b expression and/or a blood-based assay demonstrating FGFR2 amplification). Patients will be enrolled into either Part 1 or Part 2 of the study, but not both.

After an initial screening period of up to 14 days (2 weeks), patients will be treated with mFOLFOX6 (with or without anti-FGFR2-IIIb) every 2 weeks in 14-day cycles. Patients may have initiated or received mFOLFOX6 chemotherapy prior to enrollment into Part 1, but eligibility requires that the patient be a candidate to receive at least 2 additional cycles of mFOLFOX6 chemotherapy (there is no upper limit on the number of FOLFOX cycles patients in Part 1 may have received, or they may not have received any).

Each patient enrolled into Part 1 will be observed for 28 days for safety assessments and occurrence of dose-limiting toxicities (DLT Period). Upon completion of the DLT Period, patients may continue to receive treatments at the Investigator's discretion. Additional treatments may be administered every 2 weeks in 14-day cycles thereafter as clinically indicated.

In Part 2, patients whose tumor is positive for FGFR2b by IHC or blood, who have completed 2 cycles of mFOLFOX chemotherapy as standard first line therapy for advanced stage gastric cancer, and who have signed the informed consent, will be randomized 1:1 to be treated with anti-FGFR2-IIIb in combination with mFOLFOX6 or placebo in combination with mFOLFOX6 every 2 weeks in 14-day cycles at an RD selected after assessment of data obtained in Part 1.

Initial Screening Period

Part 1

The screening period begins when patients sign the informed consent form (ICF). All patients will undergo screening assessments within 14 days (2 weeks) prior to the first dose of anti-FGFR2-IIIb. Any AEs unrelated to study procedures that occur after signing of the informed consent form and before administration of the first anti-FGFR2-IIIb dose will not be collected during this period. Patients may have initiated or received mFOLFOX6 chemotherapy prior to enrollment into Part 1, but eligibility requires that the patient be a candidate to receive at least 2 additional cycles of mFOLFOX6 chemotherapy (there is no upper limit on the number of FOLFOX cycles patients in Part 1 may have received, or they may not have received any).

Part 2

In Part 2, patients will be enrolled whose tumor is positive for FGFR2b by IHC or blood, who have completed 2 cycles of mFOLFOX chemotherapy as standard first line therapy for advanced stage gastric cancer, and who have signed the informed consent and met other eligibility criteria.

Eligibility for Part 2 will be evaluated in 2 steps: a Pre-Screening Period involving only testing for FGFR2b positivity by IHC and blood; and a Screening Period in which all remaining eligibility criteria are confirmed.

Randomization
Part 1
Part 1 is an open-label study. Patients who are determined to be eligible will be enrolled sequentially.
Part 2
During the Pre-screening Period, patients will be tested for FGFR2b positivity. Patients who test positive by one or both methods (IHC and/or blood) will then enter the Screening Period. (Note: if the blood test is positive, there is no need to wait for IHC results, as the patient is eligible at that point, and should begin the Screening Period).

Patients who meet eligibility will be randomized 1:1 to placebo in combination with mFOLFOX6 or anti-FGFR2-IIIb in combination with mFOLFOX6.
Part 1 (Dose Escalation Safety Run-in)
Part 1 is an open-label dose-escalation study of anti-FGFR2-IIIb when given in combination with mFOLFOX6. Patients eligible for Part 1 have unselected GI cancer (with or without FGFR2b overexpressing tumors) with unresectable, locally advanced, or metastatic disease, and are candidates to receive both anti-FGFR2-IIIb and mFOLFOX6 chemotherapy. FGFR2 status will be determined retrospectively by IHC and blood-based biopsy.

Patients enrolled into Part 1 will be treated with escalating doses of anti-FGFR2-IIIb in combination with a fixed-dose backbone chemotherapy regimen of mFOLFOX6 every 2 weeks in 14-day cycles, as follows:
Anti-FGFR2-IIIb Administration:
Anti-FGFR2-IIIb IV is administered every 2 weeks on Day 1 of each cycle prior to administration of mFOLFOX6 chemotherapy. Anti-FGFR2-IIIb will be administered as an approximately 30-minute IV infusion via a peripheral vein or central venous catheter with in-line filter.
Backbone Chemotherapy Regimen:
Administration of mFOLFOX6 chemotherapy will commence on Day 1 of each treatment cycle and after administration of anti-FGFR2-IIIb (following a 30-minute rest). The mFOLFOX6 regimen is administered every 2 weeks as follows:
Oxaliplatin 85 mg/m$^2$ IV infusion over 120 minutes, leucovorin 400 mg/m$^2$ IV infusion over 120 minutes, followed by fluorouracil (5-FU) 400 mg/m$^2$ IV bolus, followed by 5-FU 2400 mg/m$^2$ as a continuous IV infusion over 46 hours.

The administration of oxaliplatin does not require pre-hydration. Premedication with anti-emetics, such as serotonin antagonists with or without dexamethasone, may be used where clinically indicated at the discretion of the Investigator per local standard of care.
Dose Levels (Part 1)
In Part 1, two dose cohorts of anti-FGFR2-IIIb are anticipated in a standard 3+3 dose escalation design, with a minimum of 3 patients enrolled into each cohort. The anticipated dose levels are:

| | |
|---|---|
| Dose Level 1 | 10 mg/kg anti-FGFR2-IIIb |
| Dose Level 2 | 15 mg/kg anti-FGFR2-IIIb |
| Dose Level −1 | 6 mg/kg anti-FGFR2-IIIb (if dose reduction is required from starting Dose Level 1) |

All dose escalation decisions will be based on an assessment of DLTs, overall safety, and tolerability, and will be made after the last patient enrolled in each cohort has completed the 28-day DLT Period (completion of 2 treatment cycles). Dose escalation decisions will be agreed upon by the Cohort Review Committee (CRC), consisting of the Sponsor and Investigators. Review of safety and PK parameters may inform decisions to add cohorts with alternative dose levels in order to reach an optimal target exposure. Dose Level-1 will only be enrolled if ≥2 DLTs are observed at Dose Level 1.

The algorithm shown in Table 2 will be used for Part 1 dose escalation decisions:

TABLE 2

Dose Escalation

| Number of Patients with DLTs | Action |
|---|---|
| 0/3 | Open next cohort |
| 1/3 | Enroll 3 more patients in same cohort |
| ≥2/3 | Stop enrollment. Enter 3 more patients at dose level below, if only 3 were previously entered |
| 1/6 | Open next cohort |
| ≥2/6 | Stop enrollment. Enter 3 more patients at dose level below, if only 3 were previously entered to demonstrate that ≤1 of 6 patients experience DLT |

The RD of anti-FGFR2-IIIb for Part 2 will be identified by the CRC based on an evaluation of the overall safety, tolerability, and PK. The RD, therefore, may or may not be the same as the identified maximum tolerated dose (MTD). For example, if the MTD is not reached, or if data from subsequent cycles of treatment from Part 1 provide additional insight on the safety profile, then the RD may be a different, though not higher, dose than the MTD.

The MTD is defined as the maximum dose at which <33% of patients experience a DLT during the DLT Period. If a DLT is observed in 1 of 3 patients at a given dose level, then 3 additional patients will be enrolled at that same dose level. Dose escalation may continue until 2 of 3 to 6 patients treated at a dose level experience a DLT (dose level not to exceed 15 mg/kg). The next lower dose will then be considered the MTD.

Once the MTD or RD has been reached, 3 additional patients will be added, to further explore the safety and PK at this dose level. The total enrollment for Part 1 will, therefore, be approximately 9 to 12 patients.

Any patient who does not receive exactly 2 doses of anti-FGFR2-IIIb in combination with mFOLFOX6 during the DLT Period will be considered unevaluable and the patient will be replaced. The replaced patient may continue on study after discussion with the Sponsor. No more than 2 doses of anti-FGFR2-IIIb or 2 cycles of mFOLFOX6 should be administered during the 28-day DLT Period.

On completion of the DLT Period, patients may continue receiving anti-FGFR2-IIIb in combination with mFOLFOX6, administered every 2 weeks in 14-day cycles until Investigator-assessed radiographic or clinical disease progression, unacceptable toxicity, or until the patient meets any of the other protocol-specified withdrawal criteria. There is no maximum number of doses of anti-FGFR2-IIIb. Ongoing administration of the mFOLFOX6 regimen beyond the DLT Period will be according to regional standard of care.

In the case of discontinuation of mFOLFOX6 chemotherapy administration for any reason prior to disease progression (e.g., cumulative toxicity or completion of mFOLFOX6 chemotherapy per regional practice), anti-FGFR2-IIIb may be continued as monotherapy and administered every 2 weeks until Investigator-assessed radiographic or clinical disease progression, unacceptable toxicity, or until the patient meets any of the other protocol-specified withdrawal criteria. In the event a cycle of mFOLFOX6 is delayed beyond 14 days due to chemotherapy-related toxicity, anti-FGFR2-IIIb administration should not be delayed and may continue to be administered every 2 weeks. Initiation of a new cycle of mFOLFOX6 following a dosing delay should be synchronized with administration of an anti-FGFR2-IIIb infusion where possible (but is not a study requirement).

In the case of discontinuation of anti-FGFR2-IIIb for any reason prior to disease progression (e.g., cumulative toxicity), mFOLFOX6 chemotherapy may continue to be administered in accordance with local regional practice, or until Investigator-assessed radiographic or clinical disease progression, unacceptable toxicity, or the patient meets any of the other protocol-specified withdrawal criteria.

Part 2: Randomized, Double-Blind Dose Expansion

Patients will be enrolled into Part 2 with the objective of characterizing the safety and efficacy of anti-FGFR2-IIIb combined with mFOLFOX6 compared to placebo and mFOLFOX6 in an FGFR2b-selected gastric cancer patient population. Enrollment into Part 2 will begin only once an RD for anti-FGFR2-IIIb, which will not exceed 15 mg/kg, has been identified by the CRC in Part 1.

Part 2 is double-blind and will consist of a total of up to approximately 360 FGFR2b-selected gastric cancer patients randomized 1:1 to receive one of two treatment arms:

Arm 1: anti-FGFR2-IIIb at the RD and mFOLFOX6 administered every 2 weeks; or

Arm 2: Placebo and mFOLFOX6 administered every 2 weeks

Opening of Part 2 for enrollment will be at the discretion of the Sponsor.

Patients with gastric cancer with unresectable, locally advanced, or metastatic disease who are eligible for first-line mFOLFOX6 chemotherapy and have received 2 cycles of mFOLFOX6 will be enrolled into Part 2 of the study. Patients will be selected for enrollment based on FGFR2b overexpression and/or FGFR2 amplification, as determined by a validated IHC or blood-based biopsy assay, respectively.

Enrolled patients may continue treatment every 2 weeks in 14-day cycles until Investigator-assessed radiographic or clinical disease progression, unacceptable toxicity, or until the patient meets any of the other protocol-specified withdrawal criteria. All treatment decisions will be made by the Investigator using local assessments. After discontinuation of study treatment for reasons other than progression or withdrawal of consent, tumor assessments will continue until the patient initiates additional anti-cancer therapy. In addition, patients in both Part 1 and Part 2 will undergo long-term follow-up for survival by clinic visit or by telephone approximately every 3 months±28 days after the EOT visit until up to 24 months after the last patient is enrolled into the study, or until death, loss to follow-up, withdrawal of consent or study termination by the Sponsor (whichever occurs first).

In the case of discontinuation of mFOLFOX6 chemotherapy administration for any reason prior to disease progression (e.g., cumulative toxicity or completion of mFOLFOX6 chemotherapy per regional practice), IP may be continued as monotherapy and administered every 2 weeks until Investigator-assessed radiographic or clinical disease progression, unacceptable toxicity, or until the patient meets any of the other protocol-specified withdrawal criteria. In the event a cycle of mFOLFOX6 is delayed beyond 14 days due to chemotherapy-related toxicity, IP administration should not be delayed and may continue to be administered every 2 weeks. Initiation of a new cycle of mFOLFOX6 following a dosing delay should be synchronized with administration of an IP infusion where possible (but is not a study requirement).

In the case of discontinuation of IP for any reason prior to disease progression (e.g., cumulative toxicity), mFOLFOX6 chemotherapy may continue to be administered in accordance with local regional practice, or until Investigator-assessed radiographic or clinical disease progression, unacceptable toxicity, or the patient meets any of the other protocol-specified withdrawal criteria.

Study Schema

The study schema is shown in FIG. 1 (Part 1) and FIG. 2 (Part 2).

Rationale for the Study Design

This is a 2-part, multicenter study to evaluate the safety, tolerability, PK, PD, and efficacy of anti-FGFR2-IIIb when given in combination with mFOLFOX6. The study will include an open-label, Part 1 dose escalation safety run-in and a randomized, double-blind, placebo-controlled, Part 2 dose expansion.

Part 1 is a dose-escalation safety run-in study of anti-FGFR2-IIIb when given in combination with mFOLFOX6. A standard 3+3 design will be used. Patients enrolled into Part 1 will be treated with escalating doses of anti-FGFR2-IIIb in combination with a fixed-dose backbone chemotherapy regimen of mFOLFOX6 every 2 weeks in 14-day cycles. Each patient enrolled into Part 1 will be observed for 28 days for safety assessments and occurrence of dose-limiting toxicities (DLT Period) and an RD will be selected for Part 2 after assessing the data.

Patients eligible for Part 1 have unselected GI cancer (with or without FGFR2b overexpressing tumors) with unresectable, locally advanced, or metastatic disease, and are candidates to receive both anti-FGFR2-IIIb and mFOLFOX6 chemotherapy. FGFR2 status will be determined retrospectively by IHC and blood-based biopsy.

In Part 2, selected patients will be randomized 1:1 to be treated with anti-FGFR2-IIIb and mFOLFOX6 or placebo and mFOLFOX6 every 2 weeks in 14-day cycles. Patients in Part 2 must have completed exactly 2 cycles of mFOLFOX6 (no more and no less).

Measuring the PFS, ORR, and OS in patients with FGFR2b-selected gastric cancer in randomized patients may highlight the clinical benefit of anti-FGFR2-IIIb when given in combination with mFOLFOX6 compared to placebo and mFOLFOX6.

Study Eligibility and Withdrawal Criteria
Planned Number of Patients and Study Centers In Part 1, 2 dose cohorts of anti-FGFR2-IIIb are anticipated in a standard 3+3 dose escalation design, with a minimum of 3 patients enrolled into each cohort. Once the MTD or RD has been reached, 3 additional patients will be added, to further explore the safety and PK at this dose level. The total enrollment for Part 1 will, therefore, be approximately 9 to 12 patients.

In Part 2, up to approximately 360 FGFR2b-selected gastric cancer patients will be randomized 1:1 to be treated with anti-FGFR2-IIIb in combination with mFOLFOX6 or placebo in combination with mFOLFOX6 every 2 weeks in 14-day cycles at an RD selected after assessment of data obtained in Part 1. Opening of Part 2 for enrollment will be at the discretion of the Sponsor.

The total enrollment planned for this study is approximately 372 patients.

The study will be conducted at up to 250 global study centers.

Inclusion Criteria for all Cohorts

Patients enrolling into either Part 1 or Part 2 of the study must meet all of the following inclusion criteria:
1) Disease that is unresectable, locally advanced, or metastatic
2) Understand and sign an Institutional Review Board (IRB)/Independent Ethics Committee (IEC)-approved informed consent form (ICF) prior to any study-specific evaluation
3) Life expectancy of at least 3 months
4) Eastern Cooperative Oncology Group (ECOG) performance status of 0 to 1
5) Age≥18 years at the time the ICF is signed
6) Negative serum β-human chorionic gonadotropin (β-hCG) pregnancy test≤72 hours prior to enrollment (women of childbearing potential only)
7) In sexually active patients (women of child bearing potential and males), willingness to use 2 effective methods of contraception, of which 1 must be a physical barrier method (condom, diaphragm, or cervical/vault cap) until 6 months after the last dose of anti-FGFR2-IIIb. Other effective forms of contraception include:

Permanent sterilization (hysterectomy and/or bilateral oophorectomy, or bilateral tubal ligation with surgery, or vasectomy) at least 6 months prior to Screening Women of childbearing potential that are on stable oral contraceptive therapy or intrauterine or implant device for at least 90 days prior to the study, or abstain from sexual intercourse as a way of living
8) Adequate hematological and biological function, confirmed by the following laboratory values:

Bone Marrow Function
Absolute neutrophil count (ANC) $1.5\times10^9$/L
Platelets>$100\times10^9$/L
Hemoglobin ≥9 g/dL Hepatic Function
Aspartate aminotransferase (AST) and alanine aminotransferase (ALT) ≤3×upper limit of normal (ULN); if liver metastases, then ≤5×ULN
Bilirubin≤1.5×ULN Renal Function
Calculated creatinine clearance≥50 mL/min
9) Patients on full-dose anticoagulants must be on a stable dose of warfarin and have an in-range international normalized ratio (INR) within the therapeutic range for the patient's condition or be on a stable dose of low molecular weight heparin
10) Measurable or non-measurable disease
11) Tumor tissue for determination of FGFR2 status Patients enrolling into Part 1 (Dose-Escalation Safety Run-in) of the study must also meet the following inclusion criteria:

Histologically or cytologically confirmed gastrointestinal malignancy for which mFOLFOX6 is considered an appropriate treatment (e.g., gastric cancer, colorectal carcinoma, pancreatic adenocarcinoma)

No more than 2 prior chemotherapy regimens for metastatic disease (not including prior adjuvant chemotherapy with 5-FU and/or oxaliplatin).

Patient must be a candidate for at least 2 cycles of mFOLFOX6 chemotherapy.

Patients enrolling into Part 2 (Dose-Expansion) of the study must also meet the following inclusion criteria:
1) Histologically documented gastric or gastroesophageal junction adenocarcinoma
2) FGFR2b overexpression as determined by IHC and/or FGFR2 amplification as determined by blood-based biopsy
3) No prior chemotherapy for metastatic or unresectable disease (except as noted in Inclusion Criteria #20 for mFOLFOX6)
4) No prior platinum-based chemotherapy (except as noted in Inclusion Criteria #20 for mFOLFOX6)
5) If prior adjuvant or neo-adjuvant therapy (chemotherapy and/or chemoradiation) has been received, more than 6 months must have elapsed between the end of adjuvant therapy and enrolment
6) Patient must be a candidate for mFOLFOX6 chemotherapy and have received 2 cycles of mFOLFOX6 chemotherapy prior to study enrollment (but not more than 2 cycles)

Exclusion Criteria for all Cohorts

Patients enrolling into either Part 1 or Part 2 will be excluded if any of the following criteria apply:

Untreated or symptomatic central nervous system (CNS) metastases. Patients with asymptomatic CNS metastases are eligible provided they have been clinically stable for at least 4 weeks and do not require intervention such as surgery, radiation, or any corticosteroid therapy for management of symptoms related to CNS disease Impaired cardiac function or clinically significant cardiac disease, including any of the following:

Unstable angina pectoris≤6 months prior to enrollment
Acute myocardial infarction≤6 months prior to enrollment
New York Heart Association class II-IV congestive heart failure
Uncontrolled hypertension (as defined as >160/90 despite optimal medical management)
Cardiac arrhythmia requiring anti-arrhythmic therapy other than beta blockers or digoxin
Active coronary artery disease
7) QTcF>450 msec for males or >470 msec for women
8) Peripheral sensory neuropathy≥Common Terminology Criteria for Adverse Events (CTCAE) grade 2
9) Active infection requiring systemic treatment or any uncontrolled infection≤14 days prior to enrollment
10) Known human immunodeficiency virus (HIV) or acquired immunodeficiency syndrome (AIDS)-related illness, or history of chronic hepatitis B or C
11) History of interstitial lung disease (e.g., pneumonitis or pulmonary fibrosis)
12) Evidence or history of bleeding diathesis or coagulopathy
13) Any investigational agent or therapy ≤28 days prior to enrollment
14) Radiotherapy≤28 days of enrollment. Patients must be recovered from all radiotherapy-related toxicities. No radiopharmaceuticals (strontium, samarium) within 8 weeks of enrollment
15) Prior treatment with any selective inhibitor (e.g., AZD4547, BGJ398, JNJ-42756493, BAY1179470) of the FGF-FGFR pathway
16) Ongoing adverse effects from prior treatment>NCI CTCAE Grade 1 (with the exception of Grade 2 alopecia)
17) Participation in another therapeutic clinical study within 28 days of enrollment or during this clinical study 18) Corneal defects, corneal ulcerations, keratitis, keratoconus, history of corneal transplant, or other known abnormalities of the cornea that may, in the opinion of an ophthalmologist, pose a risk with anti-FGFR2-IIIb treatment
19) Positive HER2 status (as defined by a positive IHC test of 3+ or IHC of 2+ with positive FISH). HER2 status is based on scoring guidelines for gastric cancer (HercepTest).
20) Major surgical procedures are not allowed ≤28 days prior to enrollment. Surgery requiring local/epidural anesthesia must be completed at least 72 hours before enrollment. In all cases the patient must be sufficiently recovered and stable before treatment administration
21) Women who are pregnant or breastfeeding (unless the patient is willing to interrupt breastfeeding during study drug administration and then resume 6 months after study discontinuation); women of childbearing potential must not consider getting pregnant during the study
22) Presence of any serious or unstable concomitant systemic disorder incompatible with the clinical study (e.g., substance abuse, psychiatric disturbance, or uncontrolled intercurrent illness including active infection, arterial thrombosis, and symptomatic pulmonary embolism)
23) Presence of any other condition that may increase the risk associated with study participation (e.g., dihydropyrimidine deficiency or pleural effusion) or may interfere with the interpretation of study results, and, in the opinion of the Investigator, would make the patient inappropriate for entry into the study
24) Known allergy or hypersensitivity to components of the anti-FGFR2-IIIb formulation including polysorbate or to platinum-containing medications, fluorouracil, or leucovorin
25) History of prior malignancy except another malignancy that in the Investigator's opinion would not affect the determination of study treatment effect No waivers of these inclusion or exclusion criteria will be granted.

Patient Withdrawal and Replacement

A patient must be discontinued from protocol-prescribed therapy if any of the following apply:
Consent withdrawal at the request of the patient or their legally authorized representative
Progression of patient's disease as assessed by the Investigator.
Any event that would pose an unacceptable safety risk to the patient
A concurrent illness that would affect assessments of the clinical status to a significant degree
A positive pregnancy test at any time during the study
At the specific request of the Sponsor or its authorized representative (e.g., if the study is terminated for reasons of patient safety)

Patient Identification and Enrollment

Patients must be able to provide written informed consent and meet all inclusion criteria and none of the exclusion criteria. No waivers of inclusion or exclusion criteria will be granted by the Investigator and Sponsor or its designee for any patient enrolled in the study. Before enrolling a patient, all eligibility criteria must be satisfied. Patients who qualify for Part 1 of the study will be enrolled into the first available cohort. A patient may be enrolled into either Part 1 or Part 2 of the study, but not both.

In Part 2, patients first undergo Pre-screening in which both a blood-based biopsy assay and a tissue test are required. Patients who are determined to be FGFR2 positive may immediately enter the Screening Period (i.e., patients with positive blood test results need not wait for IHC results (see Table 3). Patients in Part 2 must also have completed 2, but not more than 2, cycles of mFOLFOX6.

TABLE 3

Eligibility Based on FGFR2b Results

| FGFR2 Amplification[a] (using a blood-based biopsy [ctDNA] assay)[b] | IHC FGFR2B Overexpression (using a tissue based IHC Assay)[a] (tissue test for FGFR2b protein)[c] | Eligibility |
|---|---|---|
| Blood (+) | Positive | Eligible |
| Blood (−) | Positive | Eligible |
| Blood (+) | Negative | Eligible |
| Blood (−) | Negative | Ineligible |

[a]Both tests will be carried out at central laboratories.
[b]Requires 2 × 10 mL
[c]IHC: Minimum of 5 slides required. A score of 2+ or 3+ will be considered positive.

In both Parts 1 and 2, the Investigator may repeat qualifying laboratory tests and vital signs/ECGs prior to enrollment if a non-qualifying finding is considered an error or an acute finding is likely to meet eligibility criteria on repeat testing. Hematology and blood chemistry test results must be obtained within 72 hours of dosing to confirm eligibility.

Study Drug

Identity

In Part 1, anti-FGFR2-IIIb will be supplied in a sterile vial for dilution into an intravenous bag for administration by the study site over approximately 30 minutes every 14 days (+/−3 days) until Investigator-assessed radiographic or clinical disease progression, unacceptable toxicity, or other cause for protocol-specified study withdrawal.

In Part 2, placebo will be supplied by an unblinded site pharmacist. Participants will be randomly assigned in a [1:1] ratio to receive blinded IP (anti-FGFR2-IIIb/placebo). Investigators will remain blinded to each participant's assigned study treatment throughout the course of the study. In order to maintain this blind, the unblinded pharmacist will be responsible for the reconstitution and dispensation of all study treatment. In the event of a Quality Assurance audit, the auditor(s) will be allowed access to unblinded study treatment records at the site(s) to verify that randomization/dispensing has been done accurately.

Oxaliplatin, 5-FU, and leucovorin will be supplied to each site as per routine institutional practice. The mFOLFOX6 regimen will be administered every 14 days (+/−3 days) until Investigator-assessed radiographic or clinical disease progression, unacceptable toxicity, or other cause for protocol-specified study withdrawal. Refer to the most current regional package insert for preparation and complete prescribing information.

Administration 1. mFOLFOX6

Oxaliplatin, 5-FU, and leucovorin will be supplied to each site as per routine institutional practice. The mFOLFOX6 regimen will be administered every 14 days (+/−3 days) until disease progression, unacceptable toxicity, or other cause for protocol-specified study withdrawal.

The starting dose for mFOLFOX6 includes 85 mg/m$^2$ of oxaliplatin, 350 mg of calcium folinate (folinic acid), a 400 mg/m$^2$ dose of fluorouracil, and a 2400 mg/m$^2$ dose of fluorouracil. Oxaliplatin and calcium folinate are administered concomitantly via IV infusion using a 3-way tap/Y-site connector. The smaller dose of fluorouracil is administered via IV bolus, and the larger dose of fluorouracil is administered via IV infusion over the course of 46 hours. mFOLFOX6 may be administered every 14 days.

Refer to the most current package insert for preparation and complete prescribing information.

2. Open-Label Anti-FGFR2-IIIb (Part 1) and Blinded IP (Part 2)

Anti-FGFR2-IIIb will be administered only to patients in this study using procedures described in this protocol. The dose of anti-FGFR2-IIIb is based on body weight at Cycle 1 Day 1 and adjusted if the patient's weight changes >10% from Cycle 1 Day 1.

A pharmacist (or other responsible person) will prepare the solution for administration. After calculating the number of vials, based on the patient's weight, the study drug product will be diluted in a 0.9% sodium chloride solution. Prepared anti-FGFR2-IIIb should be administered hours after preparation (ambient temperature). Anti-FGFR2-IIIb will be administered under medical supervision over approximately 30-minute IV infusion with in-line filter via a peripheral vein or central venous catheter. For Part 2, the pharmacist, who will be unblinded to treatment assignment, will supply placebo.

Infusion of anti-FGFR2-IIIb must be stopped, reduced, interrupted, or discontinued earlier. If a patient experiences an infusion reaction, the patient's vital signs (temperature, blood pressure, pulse, and respiration rate) should be monitored during the infusion as well as every 30 minutes after the infusion for a minimum of 2 hours and until resolution of the infusion reaction.

Patients will receive 2 doses of anti-FGFR2-IIIb, 2 weeks apart for the duration of study participation. In Part 1, on completion of the DLT period if treatment is tolerated without disease progression, patients may continue receiving anti-FGFR2-IIIb in combination with mFOLFOX6, administered every 2 weeks in 14-day cycles until Investigator-assessed radiographic or clinical disease progression, unacceptable toxicity, or until the patient meets any of the other protocol-specified withdrawal criteria.

Starting Dose and Dose Modifications

3. Part 1: Dose-Escalation Safety Run-in

Patients enrolled into Part 1 will be treated with escalating doses of anti-FGFR2-IIIb in combination with a fixed-dose backbone chemotherapy regimen of mFOLFOX6 every 2 weeks in 14-day cycles, as described above.

Dose Modification Criteria

4. Open-Label Anti-FGFR2-IIIb (Part 1) and Blinded IP (Part 2)

Part 1 and Part 2:

Dose reductions for anti-FGFR2-IIIb may be permitted for patients on treatment beyond the DLT Period in Part 1 or any patient in Part 2 per the guidelines outlined in Table 4. If dose reductions or interruptions that do not fall within these guidelines are being considered by the Investigator, these will require discussion with and approval by the Sponsor or designee.

TABLE 4

Dose Modification Guidelines for anti-FGFR2-IIIb

| Toxicity Grade | Anti-FGFR2-IIIb Dose | Dose Schedule |
|---|---|---|
| 1 or 2 | Continue 100% of dose | No delay or missed dose required |
| 3 or 4 (first occurrence) | Continue 100% of starting dose following recovery to Baseline or Grade 1 | Delay or miss dose |

TABLE 4-continued

Dose Modification Guidelines for anti-FGFR2-IIIb

| Toxicity Grade | Anti-FGFR2-IIIb Dose | Dose Schedule |
|---|---|---|
| 3 or 4 (second occurrence) | Continue at one dose level lower than previous dose following recovery to Baseline or Grade 1 | Delay or miss dose |
| 3 or 4 (third occurrence) | Permanently discontinue dosing of anti-FGFR2-IIIb | N/A |

Patients may resume the study drug if the event returns to Baseline or ≤Grade 1 in accordance with the guidelines outlined in Table 4.

There is a ±3-day window for the scheduled dosing visits. Patients should not have 2 consecutive doses of anti-FGFR2-IIIb within 7 days. The first dose of each cycle is considered Day 1 of each cycle. Cycles will repeat every 14 days unless there is a treatment delay.

Intra-patient dose escalation above the starting dose for each patient will not be permitted. If a patient's dose is decreased for a reason that is no longer relevant, dose escalation to the originally assigned dose may occur after discussion and approval by the Sponsor.

5. mFOLFOX6

Part 1 and Part 2: Patients should be closely monitored for mFOLFOX6 toxicity. Dose adjustments for 5-FU and oxaliplatin may be permitted for patients on treatment, but patients who require dose adjustments or delay of any component of mFOLFOX during the DLT period will not be considered evaluable unless the dose adjustment or delay is due to an AE deemed related to anti-FGFR2-IIIb, in which case the AE will be considered a DLT (see below for DLT definition). Beyond the DLT Period in Part 1 or any patient in Part 2, dose adjustments for any component of mFOLFOX are permitted per the guidelines outlined in the protocol.

In the event that oxaliplatin administration is discontinued for any reason prior to disease progression, 5-FU/leucovorin therapy may continue on an every-2-week schedule until disease progression, unacceptable toxicity, or other cause for study withdrawal.

Dose adjustments for mFOLFOX6 toxicity are shown in Table 5.

TABLE 5

Dose Reductions and Delays for FOLFOX Chemotherapy

| Toxicity at the Start of Subsequent Cycles of Therapy | Grade | Oxaliplatin | 5-FU |
|---|---|---|---|
| WBC | <3.000/mm³ | Hold until resolution | |
| Neutrophils | <1.000/mm³ | | |
| Platelets | <100.000/mm³ | | |
| Diarrhea | ≥1 | | |
| Mucositis | ≥1 | | |
| Any other non-hematological toxicity | ≥2 | | |
| Hand/foot syndrome | 3-4 | 100% | STOP |
| Neurotoxicity | ≥3 | STOP | 100% |

| Previous Toxicity (after resolution) | Grade | Oxaliplatin | 5-FU |
|---|---|---|---|
| Neutropenia > 5 days | 4 | 75% | 100% |
| Febrile neutropenia | 4 | | |
| Thrombocytopenia | 3-4 | | |
| Diarrhea | 3 | 100% | 75% |
| Diarrhea | 4 | 100% | 50% |

TABLE 5-continued

Dose Reductions and Delays for FOLFOX Chemotherapy

| Stomatitis | 3 | 100% | 75% |
|---|---|---|---|
| Stomatitis | 4 | 100% | 50% |
| Myocardial ischemia | — | 100% | STOP |

Adapted from protocol for: Loupakis F, Cremolini C, Masi G, et al. Initial therapy with FOLFOXIRI and bevacizumab for metastatic colorectal cancer. *N Engl J Med* 2014; 371:1609-18. DOI: 10.1056/NEJMoa1403108.

Dose-Limiting Toxicity

DLTs are defined as any of the following events that occur during the first 28 days of treatment and are assessed by the Investigator as related to anti-FGFR2-IIIb. As applicable, events will be classified according to the NCI CTCAE (Version 4.03).

ANC<$0.5\times10^9$/L>5 days duration or febrile neutropenia (i.e., ANC<$1.0\times10^9$/L with a single temperature of >38.3° C., or fever ≥38° C. for more than 1 hour). Use of G-CSF is permitted per institutional standards Platelets<$25\times10^9$/L or platelets<$50\times10^9$/L with bleeding requiring medical intervention Prolonged (>7 days) Grade 3 thrombocytopenia Grade 4 anemia (i.e., life-threatening consequences; urgent intervention indicated)

Any Grade 2 or greater ophthalmologic AE that does not resolve within 7 days

AST/ALT>3×ULN and concurrent total bilirubin>2× ULN not related to liver involvement with cancer Any non-hematological AE Grade 3 or greater (except nausea, vomiting, and diarrhea if well controlled by systemic medication). Grade 3 or 4 lab values that are not of clinical significance per Investigator and Sponsor agreement will not be considered DLTs.

Any anti-FGFR2-IIIb related adverse event which results in a dose reduction or delay by at least 4 days of any component of mFOLFOX6

Recommended Dose (RD) and Maximum Tolerated Dose (MTD)

Toxicity at Lowest Dose Level

If the MTD is unexpectedly exceeded at the first dose level of anti-FGFR2-IIIb (10 mg/kg Q2W), then decisions on how to proceed will be based on safety, tolerability, and PK data; and will be agreed on between the Investigators and Sponsor.

Dose Level-1 (anti-FGFR2-IIIb 6 mg/kg Q2W; 3 to 6 subjects) will only be enrolled if ≥2 DLTs are observed at Dose Level 1.

Dose Escalation within a Cohort

In Part 1, intra-patient dose escalation will not be permitted.

In Part 2, patients will be treated at the RD as determined from Part 1, and dose escalation will not be allowed.

Dose Interruptions During Study Drug Infusion

Infusion of anti-FGFR2-IIIb must be stopped if any AE ≥Grade 3 occurs during the infusion. If bronchospasm or dyspnea occurs in a patient during infusion, the infusion should be stopped. Symptoms of infusion reactions may include: fever, chills, rigors, urticaria, hypotension and hypertension with headache, wheeze, breathlessness, hypoxia, and pulmonary infiltrates.

In addition, at the Investigator's discretion, the infusion rate may be reduced or stopped if a less severe AE (Grade 1 or 2) occurs during the infusion. If a Grade 3 or less severe AE resolves within 4 hours, the infusion may be restarted at half the previous rate. If the same AE appears again with the same severity at any time during the restarted infusion, the infusion should be discontinued, and no further dosing of study drug will occur without consultation with the Sponsor or Sponsor's designee.

If a patient experiences an infusion reaction prior to completion of the infusion, the infusion must be stopped, and the patient should be promptly managed and monitored according to signs and symptoms, and local clinical protocol until there is a complete resolution of the event. For patients whose infusion-associated events were either Grade 1 or 2, and completely resolved on the day of the infusion, the infusion may be resumed at the discretion of the Investigator at a slower rate with premedication. All subsequent infusions for that patient should then be administered at the reduced rate of infusion with pre-medications. Pre-medications may include medications such as corticosteroids, diphenhydramine, acetaminophen and/or bronchodilators as indicated. Anti-FGFR2-IIIb will be permanently discontinued for patients who have experienced Grade 3 or above infusion-associated adverse events, and for patients who have recurrent infusion-associated reactions after restarting the infusion despite pre-medications and slower infusion.

If a patient experiences an infusion reaction, the patient's vital signs (temperature, blood pressure, pulse, and respiration rate) should be monitored during the infusion, as well as every 30 minutes after the infusion for a minimum of 2 hours and until resolution of the infusion reaction.

Dose interruptions and delays resulting from mFOLFOX6 toxicity are described in Table 5 (see product labels for leucovorin, 5-FU, and oxaliplatin).

Parameters and Methods of Assessment

Safety Parameters

Safety measures will include AEs, hematology, clinical chemistry, urinalysis, vital signs, body weight, concomitant medications/procedures, ECOG performance status, targeted physical examinations, ECGs, and ophthalmology examinations.

1.1 Tumor Analysis for Patient Selection 1.1.1 Part 1

Patients eligible for Part 1 have unselected GI cancer (with or without FGFR2b overexpressing tumors) with unresectable, locally advanced, or metastatic disease, and are candidates to receive both anti-FGFR2-IIIb and mFOLFOX6 chemotherapy. FGFR2 status will be determined retrospectively by IHC and blood-based biopsy.

1.1.2 Part 2

Patients in Part 2 of this study must consent to tumor tissue analysis and blood sample analysis. Patients will be selected for enrollment based on FGFR2b overexpression and/or FGFR2 amplification, as determined by a validated IHC or blood-based biopsy assay, respectively. Patients who do not demonstrate either FGFR2b overexpression using IHC or amplification using a blood-based biopsy assay will not be eligible for enrollment; however, positivity based on one or both of the assays is adequate to meet eligibility requirements (e.g., positive by blood-based biopsy assay, but negative by IHC). It is the responsibility of each Investigator to obtain an adequate tumor specimen for analysis of FGFR2b overexpression for enrollment. Tumor slide or tumor block specimen processing, labeling, and shipping instructions are detailed in the Lab Manual that will be distributed with the specimen collection kit.

Third-party laboratories will perform the FGFR2b expression and FGFR2 amplification analysis using a validated IHC and blood-based assay, respectively.

For Part 2, once tumor and blood specimens are received, analysis will be performed as efficiently as possible, and results will be communicated back to the Investigator or designee.

1.2 Fresh Tumor Biopsies for Pharmacodynamic Analysis 1.2.1 Part 2 Only

Tumor biopsy samples are also being collected to evaluate the pharmacodynamic effect of anti-FGFR2-IIIb on the tumor microenvironment. These biopsy samples will be obtained before treatment and on-treatment to examine immune infiltrates and expression of selected tumor markers. An optional biopsy may also be obtained of tumors that have responded and/or progressed on or after treatment to understand mechanisms of resistance. Tumor biopsy samples may be assessed for the expression of immune or disease-related genes and/or proteins, as well as for the presence of immune cell populations using a variety of methodologies including but not limited to IHC, qRT-PCR, genetic mutation detection, and fluorescent in situ hybridization (FISH). These samples may also undergo RNA sequencing to determine the effect of anti-FGFR2-IIIb on gene expression pathways as well as identified gene expression signatures associated with response or resistance to response. These analyses may help predict future response to treatment. Other methods of tumor biomarker expression are also being evaluated.

A fresh biopsy at a primary tumor or metastatic tumor site is mandatory, as feasible, for up to 30 patients randomized into Part 2 at Screening (at least 24 hours prior to dosing) and on treatment within 7 days prior to Cycle 3 Day 1 (and at least 24 hours prior to dosing). For patients who have had a biopsy acquired within the 12 weeks prior to enrollment, this sample may fulfill the requirement for a fresh pre-treatment biopsy provided adequate sample is available for PD analysis (a single paraffin-embedded block or approximately 10 slides).

Patients in Part 2 may also have an optional on-treatment biopsy upon documented tumor response, within 28 (±7) days post tumor assessment. Patients in Part 2 may also have an optional post-treatment biopsy at the EOT visit upon documented tumor progression. In each case, consultation with the Sponsor should take place before the biopsy occurs. Both biopsies are optional.

The feasibility of acquiring a fresh tumor sample at each time point will be assessed by the Investigator and should include a consideration of patient safety. If the Investigator assesses that a biopsy is not feasible, then this determination must be recorded in the source documents.

Biopsied lesions may become inflamed, bleed, or change dimensions, which could result in inaccurate tumor measurements. Therefore, it is strongly recommended not to use the biopsied lesion as a target lesion when assessing the response by RECIST v 1.1 criteria. These biopsy samples should be excisional, incisional or core needle. Fine needle aspirates or other cytology specimens are insufficient for downstream biomarker analyses. Tumor tissue specimens in the form of a paraffin embedded block or unstained slides will be submitted for central IHC assessment.

1.3 Tumor Assessments

Tumor assessments should consist of clinical examination and appropriate imaging techniques (preferably CT scans with appropriate slice thickness per RECIST v1.1); other assessments (MRI, radiograph, PET, and ultrasound) may be performed if required. The same methods used to detect lesions at baseline are to be used to follow the same lesions throughout the clinical study. Screening tumor scan must be within 2 weeks of the start of treatment on Cycle 1 Day 1.

Tumor response assessment will be performed both by the Investigator and by blinded central radiology review per RECIST 1.1 guidelines.

Tumor scans will be performed at Screening (within 2 weeks of Cycle 1 Day 1 in Part 1 and Part 2) and within 7 days prior to the start of Cycle 4 Day 1, Cycle 7 Day 1, Cycle 10 Day 1, Cycle 13 Day 1, and then approximately every 12 weeks. If initial CR or PR is noted, confirmatory scans must be performed 4 to 6 weeks later.

After discontinuation of study treatment for reasons other than progression or withdrawal of consent, tumor assessments will continue until the patient initiates additional anti-cancer therapy or progresses.

1.3.1 Blood-Based Biopsy (ctDNA)

In Part 1, samples for blood-based biopsy (ctDNA) assay will be collected prior to the first dose of study drug (Cycle 1 Day 1) and analyzed retrospectively for FGFR2 amplification.

In Part 2, a pre-screening blood-based biopsy (ctDNA) assay will be done. This sample will be analyzed prospectively for FGFR2 amplification. In addition, blood-based biopsy (ctDNA) assays will be collected longitudinally every 6 weeks from the first dose for 24 weeks, and then approximately every 12 weeks thereafter, and analyzed retrospectively for FGFR2 amplification. A sample will also be collected at the EOT visit for all Part 2 patients.

1.4 Pharmacodynamic Biomarker Analysis Using Hair Follicles

In Part 1 only, hair follicles (approximately 10, if available) from either eyebrows or scalp will be collected from all patients for whom sampling is possible. Hair follicles are known to express the FGFR2b receptor and alterations in levels of FGFR2b and downstream signaling may be used to correlate the dose of anti-FGFR2-IIIb required to effectively block FGFR2b receptors and downstream signaling and may help provide guidance in choosing the RD for Part 2 of the study.

1.5 Pharmacodynamic Biomarker Analysis Using Blood

Serum samples for exploratory biomarker analysis of the FGFR pathway (for example: FGF7, FGF10) will be collected from all patients prior to dosing at the timepoints specified in Appendix 3.

1.6 Blood Sample for ctDNA 1.7 Pharmacodynamic Biomarker Analysis Using Tumor Biopsies Levels of immune cell infiltrate and other exploratory biomarkers will be analyzed in pre-treatment and on-treatment tumor biopsy samples from all patients.

1.8 FCGR Polymorphisms

Blood samples are also collected for polymorphisms that frequently occur in Fc-gamma receptors, such as FCGR2A and FCGR3A. These genes express Fc gamma receptors on white blood cells that are an integral part of the ADCC pathway, which is an anticipated mechanism of action of anti-FGFR2-IIIb. The data will be collected for a retrospective analysis at the completion of the study to correlate patient response to anti-FGFR2-IIIb. These biomarker tests are considered exploratory.

1.9 Quality of Life Scales

The EQ-5D-5L quality of life (QoL) questionnaire and the EORTC QLQ-C30 will be administered on multiple occasions prior to dosing (see Appendix 1 for time points).

The EQ-5D-5L questionnaire was developed by the EuroQol Group, which is a standardized measure to provide utilities for clinical and economic appraisal. It uses a descriptive system and a visual analogue scale (VAS). The descriptive system has 5 dimensions: mobility, self-care, usual activities, pain/discomfort and anxiety/depression, and each dimension has 5 levels: no problems, slight problems, moderate problems, severe problems, and extreme problems.

Respondents are asked to indicate their health state by marking the box against the most appropriate statement in each of the 5 dimensions. The digits for the 5 dimensions can be combined in a 5-digit number describing the respondent's health state. Health states defined by the EQ-5D-5L descriptive system are converted into a single index value to calculate utilities. The VAS portrays the respondent's self-rated health on a 20-cm vertical VAS, with endpoints labeled "the best health you can imagine" and "the worst health you can imagine".

The European Organisation for Research and Treatment of Cancer (EORTC) quality of life questionnaire (QLQ) is an integrated system for assessing the health-related quality of life of cancer patients participating in international clinical trials. The EORTC uses a modular approach to QoL assessment, consisting of a core questionnaire (EORTC QLQ-C30) to be administered, if necessary with a module specific to tumor site, treatment modality or a QoL dimension (e.g., gastric cancer-specific module is QLQ-ST022).

The patient provides answers for five functional scales (physical, role, emotional, social, and cognitive), three symptom scales (fatigue, nausea and vomiting, and pain) and a global health status/QOL scale and six single items (dyspnea, insomnia, appetite loss, constipation, diarrhea, and financial difficulties).

1.10 ECOG Performance Status

ECOG performance status will be assessed in all patients at the time points outlined in Appendix 1. The ECOG performance status is a scale used to assess how a patient's disease is progressing, assess how the disease affects the daily living abilities of the patient, and determine appropriate treatment and prognosis. The ECOG scale is shown in Appendix 4.

1.11 Pharmacokinetic Parameters

Blood samples to determine serum anti-FGFR2-IIIb concentration will be acquired from each patient as outlined in the Study Flowchart for Pharmacokinetic, Immunogenicity, and Pharmacodynamic Blood Sample Collections (Appendix 3).

2. Study Conduct 2.1 Overview of Patient Assessments

The schedule of detailed patient assessments is shown in Appendix 1. The list of safety laboratory assessments is shown in Appendix 2. Instructions for the sampling and processing of PK, PD, and immunogenicity data are provided in a flowchart in Appendix 3.

2.2 Study Assessments and Procedures by Visit 2.2.1 Pre-Screening Period (Part 2 Only—Pre-Study)

Written, signed informed consent (Pre-screening ICF) must be collected prior to any study-specific procedures.
 Prospective IHC analysis of FGFR2b expression and a blood-based assay demonstrating FGFR2 amplification (see above).

2.2.2 Screening Period (Day −14 to Day 0)

Written, signed informed consent must be collected prior to any study-specific procedures. Patients who have fully consented to participation in the study will undergo screening assessments within 14 days (2 weeks) prior to administration of the first infusion of anti-FGFR2-IIIb. The following procedures will be performed:
 Review/confirm eligibility criteria
 Medical and disease history, including medication history
 Tumor tissue collection from archive or newly obtained material (required for enrollment into Part 1 and Part 2)
 Demographic and baseline characteristics
 Complete physical examination, including weight and height
 ECOG performance status evaluation
 Vital signs (blood pressure, pulse, respiration, and body temperature [° C.])
 12-lead ECG after 5 minutes of rest prior to recording
 Comprehensive ophthalmologic examination
 Safety blood tests (see Appendix 2.)
 Serum pregnancy test (beta-human chorionic gonadotropin [β-HCG]), ≤72 hours prior, for women of childbearing potential
 Urinalysis (includes dipstick for protein, glucose, blood, pH, and ketones)
 Tumor assessments performed within 14 days prior to start of treatment and including clinical examination and appropriate imaging techniques, with other assessments (MRI, radiograph, PET, and ultrasound) performed if required
 Randomization for Part 2 patients only
 For up to 30 patients randomized into Part 2: Fresh tissue biopsy at primary or metastatic tumor site at least 24 hours prior to dosing. For patients who have had a biopsy acquired within the 12 weeks prior to enrollment, this sample may fulfill the requirement for a fresh pre-treatment biopsy provided adequate sample is available for PD analysis (a single paraffin-embedded block or approximately 10 slides).
 Blood-based biopsy (ctDNA) sample collection as outlined in Appendix 3.
 FOLFOX administration (For Part 1, patients may have initiated mFOLFOX6 chemotherapy prior to study enrollment, and must be a candidate for at least 2 cycles of mFOLFOX6 chemotherapy to be eligible. For Part 2, patients are required to have completed 2 cycles of mFOLFOX6 chemotherapy prior to randomization).
 AE reporting, if applicable 2.2.3 Treatment Period 2.2.3.1 Cycle 1, Day 1

The following procedures will be performed:
 Review/confirm eligibility criteria
 Update medical, disease and medication history to capture any changes from screening
 Limited physical examination including weight and oral exam
 Patient reported outcomes (EQ-5D-5L and EORTC QLQ-C30)
 Vital signs (blood pressure, pulse, respiration, and body temperature [° C.]) pre-dose and at 0.5, 1, 2, and 4 hours from the start of anti-FGFR2-IIIb infusion
 Safety blood tests, with results obtained within 72 hours prior to study drug administration to confirm eligibility (see Appendix 2.)
 Serum pregnancy test (β-HCG), ≤72 hours prior to dosing, for women of childbearing potential
 Urinalysis (includes dipstick for protein, glucose, blood, pH, and ketones)
 Blood sampling for PK, immunogenicity testing, FCGR, ctDNA, and exploratory biomarker analysis as outlined in Appendix 3.
 Blood-based biopsy (ctDNA) sample collection: In Part 1, a blood-based biopsy (ctDNA) sample will be collected prior to dosing on Cycle 1 Day 1 for retrospective analysis. No sample is needed from Part 2 patients at this timepoint.

In Part 1 only, scalp or eyebrow hair follicle samples (approximately 10, if available) will be collected prior to dosing on Cycle 1 Day 1 from all patients for whom sampling is possible.

AE reporting

Review of concomitant medications

Study Drug Administration:

Anti-FGFR2-IIIb administered by IV infusion over 30 minutes mFOLFOX6 chemotherapy administered after 30 minutes of rest 2.2.3.2 Cycle 1, Day 2

The following procedures will be performed:

Vital signs (blood pressure, pulse, respiration, and body temperature [° C.]) measured pre-dose and at 0.5, 1, and 2 hours from the start of anti-FGFR2-IIIb infusion Blood samples for PK and exploratory biomarker analysis will be collected as outlined in Appendix 3.

mFOLFOX6 administration continues

AE reporting

Review of concomitant medications 2.2.3.3 Cycle 1, Day 3

The following procedures will be performed:

Vital signs (blood pressure, pulse, respiration, and body temperature [° C.]) measured pre-dose and at 0.5, 1, and 2 hours from the start of anti-FGFR2-IIIb infusion Blood sampling for PK analysis as outlined in Appendix 3.

mFOLFOX6 administration continues

AE reporting

Review of concomitant medications 2.2.3.4 Cycle 1, Day 8

The following procedures will be performed:

Limited physical examination including weight and oral exam

Vital signs (blood pressure, pulse, respiration, and body temperature [° C.]) measured pre-dose and at 0.5, 1, and 2 hours from the start of anti-FGFR2-IIIb infusion Safety blood tests, with results obtained within 72 hours prior to study drug administration (see Appendix 2.)

Blood sampling for PK analysis as outlined in Appendix 3.

AE reporting

Review of concomitant medications 2.2.3.5 Cycle 2 Day 1

The following procedures will be performed:

Limited physical examination including weight and oral exam

Vital signs (blood pressure, pulse, respiration, and body temperature [° C.]) measured pre-dose and at 0.5, 1, and 2 hours from the start of anti-FGFR2-IIIb infusion Safety blood tests, with results obtained within 72 hours prior to study drug administration (see Appendix 2)

Blood sample for PK, immunogenicity testing, and exploratory biomarker analysis as outlined in Appendix 3

AE reporting

Review of concomitant medications

Study Drug Administration:

Anti-FGFR2-IIIb administered by IV infusion over 30 minutes mFOLFOX6 chemotherapy administered after 30 minutes of rest 2.2.3.6 Cycle 3 Day 1 and Day 1 of Subsequent Odd Cycles On completion of the DLT Period, patients may continue receiving anti-FGFR2-IIIb in combination with mFOLFOX6, administered every 2 weeks in 14-day cycles until Investigator-assessed radiographic or clinical disease progression, unacceptable toxicity, or until the patient meets any of the other protocol-specified withdrawal criteria. There is no maximum number of doses of anti-FGFR2-IIIb. Ongoing administration of the mFOLFOX6 regimen beyond the DLT Period will be according to regional standard of care.

The following procedures will be performed:

Limited physical examination including weight and oral exam

ECOG performance status evaluation

Patient reported outcomes (EQ-5D-5L and EORTC QLQ-C30)

Vital signs (blood pressure, pulse, respiration, and body temperature [° C.]) performed pre-dose and at 0.5, 1, and 2 hours from the start of anti-FGFR2-IIIb infusion Comprehensive ophthalmologic examination Slit lamp examinations without OCT for patients in Part 1 and for patients in Part 2 randomized to receive anti-FGFR2-IIIb and FOLFOX 6; every 6 weeks after Cycle 2 Day 1 (prior to Cycle 3 Day 15, Cycle 5 Day 1, and Cycle 6 Day 15), and then every 12 weeks after Cycle 6 Day 15. Continue every 6-8 weeks if the patient has any persistent corneal findings.

Safety blood tests, with results obtained within 72 hours prior to study drug administration (see Appendix 2)

Urine pregnancy test, ≤72 hours prior to dosing, for women of childbearing potential Urinalysis (includes dipstick for protein, glucose, blood, pH, and ketones)

Tumor assessments performed within 7 days of Cycle 3 Day 1 and including clinical examination and appropriate imaging techniques, with other assessments (MRI, radiograph, PET, and ultrasound) performed if required A fresh biopsy at a primary tumor or metastatic tumor site is mandatory, as feasible, within 7 days prior to Cycle 3 Day 1 (and at least 24 hours prior to dosing) for only up to 30 patients randomized into Part 2.

Blood sampling for PK, immunogenicity testing, blood-based biopsy (ctDNA), and exploratory biomarker analysis as outlined in Appendix 3.

For Part 2 only, a blood-based biopsy (ctDNA) sample will be collected prior to treatment Scalp or eyebrow hair follicle samples (~10, if available)

AE reporting

Review of concomitant medications

Study Drug Administration:

Anti-FGFR2-IIIb administered by IV infusion over 30 minutes on Day 1 of each cycle mFOLFOX6 chemotherapy administered after dosing with anti-FGFR2-IIIb on Day 1 of each cycle after 30 minutes of rest.

2.2.3.7 Cycle 4 Day 1 and Day 1 of Subsequent Even Cycles

The following procedures will be performed:

Limited physical examination including weight and oral exam

Patient reported outcomes (EQ-5D-5L and EORTC QLQ-C30)

Vital signs (blood pressure, pulse, respiration, and body temperature [° C.]) measured pre-dose and at 0.5, 1, and 2 hours from the start of anti-FGFR2-IIIb infusion Slit lamp examinations without OCT for patients in Part 1 and for patients in Part 2 randomized to receive anti-FGFR2-IIIb and FOLFOX 6; every 6 weeks after Cycle 2 Day 1 (prior to Cycle 3 Day 15, Cycle 5 Day 1, and Cycle 6 Day 15), and then every 12 weeks after Cycle 6 Day 15. Continue every 6-8 weeks if the patient has any persistent corneal findings.

Safety blood tests, with results obtained within 72 hours prior to study drug administration (see Appendix 2)

Tumor assessments performed within 7 days prior to start of Cycle 4 Day 1 and including clinical examination and appropriate imaging techniques, with other assessments (Mill, radiograph, PET, and ultrasound) performed if required For Part 2 only, a blood-based biopsy (ctDNA) sample will be collected prior to treatment For Part 1, blood sample for PK 4 hours prior to dosing of anti-FGFR2-IIIb and at 15 minutes (±10 minutes) after the end of the anti-FGFR2-IIIb infusion for subsequent cycles. For Part 2, PK samples to be collected (only for patients randomized to the anti-FGFR2-IIIb and mFOLFOX6 arm) 4 hours prior to dosing of anti-FGFR2-IIIb and 15 minutes (±10 minutes) after the end of the anti-FGFR2-IIIb infusion AE reporting AE reporting Review of concomitant medications Study Drug Administration:
  Anti-FGFR2-IIIb administered by IV infusion over 30 minutes on Day 1 of each cycle
  mFOLFOX6 chemotherapy administered after dosing with anti-FGFR2-IIIb on Day 1 of each cycle after 30 minutes of rest 2.2.4 End-of-Treatment Visit or Early Termination Patients will return to the study center approximately 28 (±3) days after the last study treatment administration, or in the event a patient discontinues prematurely from the study. The following assessments will be performed at the End-of-Study visit:

Limited physical examination including oral examination
ECOG performance status evaluation
Vital signs (sitting pulse, blood pressure, respiration, and body temperature [° C.] after 5 minutes of rest)
12-lead ECG after 5 minutes of rest
Comprehensive ophthalmologic examinations
Safety blood tests (see Appendix 2)
Urine pregnancy test, for women of childbearing potential
Urinalysis (includes dipstick for protein, glucose, blood, pH, and ketones)
Tumor scan, which can be omitted if the last scan was performed <6 weeks prior to EOT visit or if tumor progression was previously determined
Blood sample for immunogenicity testing
For Part 2 only, a blood-based biopsy (ctDNA) sample will be collected
Scalp or eyebrow hair follicle samples (~10, if available)
Blood sample for PK for all patients in Part 1 and all patients receiving anti-FGFR2-IIIb in Part 2
Blood sample for biomarker assessment
AE reporting
Review of concomitant medications Note: After discontinuation of study treatment for reasons other than progression or withdrawal of consent, tumor assessments will continue until the patient initiates additional anti-cancer therapy or progresses.

2.2.5 Long-Term Follow-Up

Patients in both Part 1 and Part 2 will undergo long-term follow-up for survival by clinic visit or by telephone approximately every 3 months±28 days after the EOT visit until up to 24 months after the last patient is enrolled into the study, or until death, loss to follow-up, withdrawal of consent or study termination by the Sponsor (whichever occurs first).

During the Follow-up Period, if the patient undergoes anti-cancer therapy, this should be documented.

During the first 6 months of the Follow-up Period, any pregnancy that occurs should be reported to the Sponsor.

Patients should be followed until death, loss to follow-up, withdrawal of consent, or study termination by the Sponsor.

Serious AEs occurring after the EOT visit should be reported to the Sponsor by the Investigator if the Investigator considers there is a causal relationship with the study drug.

3. Statistical Methods

Before database lock, a separate statistical analysis plan (SAP) will be finalized, providing detailed methods for the analyses outlined below. Any deviations from the planned analyses will be described and justified in the final integrated study report.

3.1 Study Patients 3.1.1 Disposition of Patients

The number and percentage of patients entering and completing each phase (e.g., Screening, Cycle 1, and subsequent cycles if given) of the study will be presented. Reasons for withdrawal will also be summarized.

3.1.2 Protocol Deviations

A summary of the number and percentage of patients with major protocol deviations by type of deviation will be provided. Deviations will be defined in the SAP prior to database lock.

3.1.3 Analysis Populations

The following analysis populations are defined for the study:

Safety Population—all patients who have received any portion of at least one dose of anti-FGFR2-IIIb.

DLT-Evaluable Population—all patients enrolled into Part 1 of the study who received at least 2 doses of anti-FGFR2-IIIb and completed Cycle 1 of treatment, or who experienced a DLT in Cycle 1.

PK-Evaluable Population—all patients who have received at least one dose of anti-FGFR2-IIIb and have had adequate PK assessments drawn for determination of the PK profile. Adequacy will be determined on a case-by-case basis and will be assessed prior to analysis of the blood samples.

Intent-to-Treat (ITT) Population—All enrolled patients

Efficacy-Evaluable Population—all patients who met eligibility criteria, received at least 1 dose of anti-FGFR2-IIIb, and have at least 1 post-baseline disease assessment 3.2 General Considerations The total enrollment planned for this study is up to approximately 372 patients. Up to approximately 12 patients evaluable for any DLT, per standard 3+3 design, will be enrolled into Part 1.

For Part 2, efficacy and tolerability will be examined by enrollment of up to approximately 360 patients with FGFR2b-selected gastric cancer, randomized 1:1 to receive anti-FGFR2-IIIb in combination with mFOLFOX6 or placebo in combination with mFOLFOX6. Eligible patients will be stratified according to geographic region (US and EU vs Asia vs Rest of World), prior treatment status (de novo vs adjuvant/neo-adjuvant), and measurable disease status (measurable vs non-measurable).

Power and Sample Size

This study is designed to provide adequate power for primary analysis of PFS.

Based on a mPFS for patients receiving placebo and mFOLFOX6 of 6 months, approximately 156 patients (randomized 1:1) with a target of 96 PFS events are required to demonstrate a hazard ratio (HR) of 0.5 for mPFS with a power of 90% (2-sided $\alpha$=0.05) for the combination of anti-FGFR2-IIIb and mFOLFOX6 compared with placebo and mFOLFOX6 after 24 months of accrual and 6 months of follow up.

Assuming an exponential distribution of PFS, this corresponds to an increase in median PFS from 6 months to 12 months. In the current design, the minimum observed effect that would result in statistical significance for PFS is a 50% improvement (HR=0.67) from 6 to 9 months.

This study is also powered for primary analysis of OS.

Based on a mOS for patients receiving placebo and mFOLFOX6 of 10 months, enrollment of the study will continue to up to approximately 360 patients with a target of 249 death events to demonstrate an HR of 0.7 for mOS with a power of 80% at the overall type I error level of 0.05 for the combination of anti-FGFR2-IIIb and mFOLFOX6 compared to placebo and mFOLFOX6 after 36 months of accrual and 10 months of follow-up after enrollment of the last patient. The group sequential method will be used to allocate type I error rate based on O'Brien-Fleming boundary and type II error rate based on the Gamma family with parameter −4 at the interim and final analysis of OS.

Assuming an exponential distribution of OS, this corresponds to an increase of 43% in median OS from 10 months to 14.3 months. In the current design, the minimum observed effect that would result in statistical significance for OS at the final analysis is a 28% improvement (HR=0.78) from 10 to 12.8 months.

Power and sample size estimates were estimated using EAST® (V6.4).

3.3 Demographics, Baseline Characteristics, and Concomitant Medications

Demographic data, medical history, concomitant disease, and concomitant medication will be summarized by cohort and overall. To determine whether the criteria for study conduct are met, corresponding tables and listings will be provided. These will include a description of patients who did not meet the eligibility criteria, an assessment of protocol violations, study drug accountability, and other data that may impact the general conduct of the study.

Baseline characteristics will be summarized for the safety population. Patients who died or withdrew before treatment started or do not complete the required safety observations will be described and evaluated separately.

3.4 Treatment Compliance

Treatment administration will be summarized by cohort including dose administration, dose modifications or delays, cumulative dose, average dose, number of infusions, and the duration of therapy.

3.5 Efficacy Analyses

In Part 1, all analyses will be descriptive and will be presented by dose group and overall as appropriate. Descriptive statistics will include number of observations, mean, standard deviation, median, range, and inter-quartile range for continuous variables, and the number and percent for categorical variables; 95% confidence intervals will be presented where appropriate.

3.5.1 Primary Efficacy Analysis

In Part 2, the primary efficacy analysis is the comparison of PFS in patients treated with anti-FGFR2-IIIb in combination with mFOLFOX6 or placebo and mFOLFOX6.

The primary endpoint, PFS, is defined as time from randomization until the date of radiologically confirmed progressive disease based on Investigator assessment (per RECIST v.1.1) or death from any cause, whichever comes first. The secondary efficacy endpoints include OS and ORR.

There will be an interim analysis and primary analysis for PFS and both are event-based analyses. Only futility test of PFS will be conducted at the interim analysis after 48 events (50% of target 96 PFS events for primary analysis of PFS) observed in the enrolled patients to exclude HR >0.806 for the combination of anti-FGFR2-IIIb and mFOLFOX6 compared with placebo and mFOLFOX6. It is estimated that the interim analysis will occur approximately 20 months from the first patient enrolled.

The primary analysis of PFS will be conducted when at least 96 PFS events have been observed in the first 156 enrolled patients, and will be performed using the intent-to-treat (ITT) population.

The primary analysis will include radiographic progression events as determined by the Investigator per RECIST v.1.1 and deaths.

The primary analysis of PFS will be conducted using a stratified log-rank 2-sided test with a 0.05 level of significance. The stratification factors will be the same used to stratify the randomization schedule as documented in the interactive voice and Web response system (IXRS).

If the p-value for the stratified log-rank test is statistically significant (<0.05 two-sided) and the HR is <1, the null hypothesis of no difference in PFS will be rejected and it will be inferred that PFS is statistically prolonged in the group receiving anti-FGFR2-IIIb in combination with mFOLFOX6 compared with the group receiving placebo and mFOLFOX6.

The median PFS and the associated 95% confidence interval for each treatment arm will be estimated using the Kaplan-Meier method. The hazard ratio (HR=$\lambda$anti-FGFR2-IIIb+ mFOLFOX6/$\lambda$mFOLFOX6) will be estimated using a Cox regression model with treatment group as the only main effect and stratifying by the same stratification factors as were used for the log-rank test. An unstratified HR will also be presented. Analyses of secondary endpoint OS will be conducted when the primary endpoint, PFS, is statistically significant, and formal hypothesis OS will be tested hierarchically at a level of 0.05. The type I error rate of testing primary and secondary endpoints will be in strong control by employing this fixed-sequence testing procedure at a level of 0.05.

3.5.2 Secondary Efficacy Analysis

Analyses of secondary endpoints including OS and ORR will be conducted when the primary endpoint, PFS, is statistically significant, and formal hypotheses of OS and ORR will be tested hierarchically at a level of 0.05. The OS will be tested first and if it is significant, the ORR will be tested next. The type I error rate of testing primary and secondary endpoints will be in a control by employing this fixed-sequence testing procedure at a level of 0.05.

There will be an interim and final analysis for OS planned if the test for PFS is statistically significant. The interim analysis of OS will be conducted at the time of primary analysis of PFS. Should OS be analyzed, analysis of OS at the interim (i.e., when at least 96 PFS events have been observed), and at the end (i.e., when 249 deaths have been observed) will be performed on the ITT population.

The hypothesis testing of OS will be conducted using a stratified log-rank 2-sided test with a 0.05 level of significance. The group sequential method will be used to allocate type I error rate based on O'Brien-Fleming boundary and type II error rate based on the Gamma family with parameter −4 at the interim and final analysis of OS. The stratification factors will be the same used to stratify the randomization schedule as documented in the IXRS.

The median OS and the associated 95% confidence interval for each treatment arm will be estimated using the Kaplan-Meier method. The HR will be estimated using a Cox regression model with treatment group as the only main effect and stratifying by the same stratification factors as were used for the log-rank test. An unstratified HR will also be presented.

The ORR is defined as the proportion of patients with partial or complete response as defined by the Investigator per RECIST v.1.1. The primary analysis of ORR will be performed among the patients with baseline measurable disease. In the analysis of ORR, patients who don't have any post-baseline adequate tumor assessments will be counted as non-responders. Formal hypothesis testing of ORR will be performed using the stratified Cochran-Mantel-Haenszel test. The stratification factors will be the same used to stratify the randomization schedule as documented in the IXRS.

3.5.3 Exploratory Efficacy Analysis

The exploratory efficacy endpoints include duration of response in responding patients, 1-year OS rate, and change from baseline in QoL as measured by EQ-5D-5L and the EORTC QLQ-C30 for all enrolled patients.

Duration of response is defined, for patients with an objective response, as the time from first radiographic documentation of objective response to disease progression by RECIST 1.1 or death due to any cause. Median duration of response and its associated 95% CI will be estimated, by treatment group, using Kaplan-Meier methods. The difference between treatment groups will be analyzed using a stratified log-rank test, using the same stratification that was used for randomization.

The 1-year OS rate, defined as proportion of patients alive at 1 year, will be estimated during the analysis of overall survival using the Kaplan-Meier method. The variance of proportions will be estimated using Greenwood's formula. The overall comparison for the difference in 1-year survival between the two treatment groups, will be calculated using the z-statistic where t=1 year.

For change from baseline in QoL as measured by EQ-5D-5L and the EORTC QLQ-C30, summary statistics for change from baseline will be presented at each post baseline assessment and at the End of Treatment. Differences between treatment groups will be analyzed using repeated measures analysis methods if applicable.

Blinded Independent Review Committee (BIRC)

A BIRC will be established to assess the concordance between investigator's assessment and BIRC's assessment. A pre-specified audit plan will be included in an imagine charter, whereas the percentage of patients, identification of imaging subsets, criteria in auditing all images, and comparison between locally-reviewing and auditing PFS results will be described in detail.

3.6 Safety Analyses

The analyses of safety will include all patients who receive any study drug (anti-FGFR2-IIIb in combination with mFOLFOX6, or placebo and mFOLFOX6) throughout the study and provide any post-treatment safety information. All AEs will be coded using the Medical Dictionary for Regulatory Activities (MedDRA). The Investigator will classify the severity of AEs using the CTCAE v 4.03.

A treatment emergent adverse event (TEAE) is defined as any event with an onset date on or after date of first dose of study drug, or any event present before treatment that worsens after treatment. Only TEAEs with an onset date prior to date of last dose+30 days will be tabulated in summary tables. The number and percentage of patients who experience AEs will be summarized by system organ class, preferred term, relationship to study drug, and severity for each treatment group. A by-patient listing will be provided for those patients who experience an SAE, including death, or experience an AE associated with early withdrawal from the study or discontinuation from study drug. Clinical laboratory data will be summarized by the type of laboratory test. The number and percentage of patients who experience abnormal (ie, outside of reference ranges) and/or clinically significant abnormalities after study drug administration will be presented for each clinical laboratory measurement. For each clinical laboratory measurement, descriptive statistics will be provided for baseline and all subsequent posttreatment scheduled visits. Changes from baseline to the posttreatment visits will also be provided. Descriptive statistics of vital signs will also be provided in a similar manner. In addition, shift from baseline in CTCAE grade (where applicable) and by high/low flags (where CTCAE grades are not defined) will be presented by treatment group. No formal comparisons of safety endpoints are planned.

3.7 Pharmacokinetic Analyses

PK parameters will be estimated using non-compartmental analysis, though compartment analysis may be employed if appropriate. Individual and mean (±SD) serum anti-FGFR2-IIIb concentration-time data will be tabulated and plotted by dose level. Anti-FGFR2-IIIb PK parameters will be estimated from the serum study drug concentration-time data using a non-compartmental analysis (NCA) method with intravenous infusion input. Alternative methods may be considered. Estimated individual and mean (±SD) PK parameters will be tabulated and summarized by dose level. Other descriptive statistics might be reported for serum anti-FGFR2-IIIb concentration-time data and estimated PK parameters. Dose proportionality, study drug accumulation, and attainment of steady state will be evaluated as data allow.

The impact of immunogenicity on anti-FGFR2-IIIb exposure will be assessed.

3.8 Interim Analyses

There will be an interim analysis for PFS, at which only a futility test of PFS will be conducted, after 48 events (50% of target 96 PFS events for primary analysis of PFS) observed in the first 156 enrolled patients, to exclude HR >0.806 in PFS for the combination of anti-FGFR2-IIIb and mFOLFOX6 compared with placebo and mFOLFOX6. In addition, there will be an interim analysis for OS planned if the test for PFS is statistically significant. The interim analysis of OS will be conducted at the time of primary analysis of PFS. Should OS be analyzed, analysis of OS at the interim will be performed on the ITT population, and the type I error rate at the interim analysis is determined by implementing a Lan-DeMets O'Brien-Fleming alpha spending function depending on the fraction of information (death events) at the time of analysis.

In addition, safety data will be reviewed on a routine basis by the Sponsor and CROs' Medical Monitors. During the dose escalation stage, the Medical Monitors and Investigator(s) will review safety data from each dose cohort prior to dose escalation or de-escalation. AE data from all cycles will be presented to the Medical Monitors when available.

3.9 Changes in the Planned Analyses

If discrepancies exist between the text of the statistical analysis as planned in the protocol and the final SAP, a protocol amendment will not be issued and the SAP will prevail.

REFERENCES

Andre F, Ranson M, Dean E, Varga A, Van der Noll R, Stockman P, et al. Results of a phase I study of AZD4547, an inhibitor of fibroblast growth factor receptor (FGFR), in patients with advanced solid tumors. Proc AACR abstract, 2013:LB-145.

Brown A, Courtney C, King L, Groom S, Graziano M. Cartilage dysplasia and tissue mineralization in the rat following administration of a FGF receptor tyrosine kinase inhibitor. Toxicol Pathol, 2005; 33:449-455.

Cunningham D, Starling N, Rao S, et al. Capecitabine and oxaliplatin for advanced esophagogastric cancer. N Engl J Med. 2008 (358): 36-46.

Dienstmann R, Bahleda R, Adamo B et al. First-in-human study of JNJ-42756493, a potent pan fibroblast growth factor receptor (FGFR) inhibitor in patients with advanced solid tumors. Proc AACR 2014: 5446 (abstract).

Fuchs C, Tomasek J, Yong C, et al. Ramucirumab monotherapy for previously treated advanced gastric or gastro-oesophageal junction adenocarcinoma (REGARD): an international, randomised, multicentre, placebo-controlled, phase 3 trial. Lancet Oncol, 2014; 383:31-39.

Garg A, Quartino A, Li J, Jin J, Wada D R, Li H, Cortes J, McNally V, Ross G, Visich J, Lum B. Population pharmacokinetic and covariate analysis of pertuzumab, a HER2-targeted monoclonal antibody, and evaluation of a fixed, non-weight-based dose in patients with a variety of solid tumors. Cancer chemotherapy and pharmacology. 2014 Oct. 1; 74(4):819-29.

Gemo A T, Deshpande A M, Palencia S, Bellovin D I, Brennan T J et al. anti-FGFR2-IIIb: A therapeutic antibody for treating patients with gastric cancers bearing FGFR2 amplification. Proc AACR 2014: CT325 (abstract).

Han K, Peyret T, Marchand M, Quartino A, Gosselin N H, Girish S, Allison D E, Jin J. Population pharmacokinetics of bevacizumab in cancer patients with external validation. Cancer Chemotherapy and Pharmacology. 2016 Aug. 1; 78(2):341-51.

Hecht J, Bang Y, Qin S, et al. Lapatinib in combination with capecitabine plus oxaliplatin in human epidermal growth factor receptor 2-positive advanced or metastatic gastric, esophageal, or gastroesophageal adenocarcinoma: TRIO-013/LOGiC—a randomized phase III trial. J Clin Oncol 2015; 34 (5):443-451.

Inoue M, Tsugane. Epidemiology of gastric cancer in Japan. Postgrad Med J. 2005; 81(957): 419-424.

Li J, Qin S, Xu J, et al. 2016. Randomized, double-blind, placebo-controlled phase III trial of Apatinib in patients with chemotherapy-refractory advanced or metastatic adenocarcinoma of the stomach or gastroesophageal junction. J Clin Oncol 2016; 34 (14):1448-1454.

Miki, T, Bottaro, D P, Fleming, T P et al. Determination of ligand-binding specificity by alternative splicing: Two distinct growth factor receptors encoded by a single gene. Proc. Natl. Acad. Sci. USA, 1992; 89: 246-250.

National Cancer Institute. SEER Stat Fact Sheets: Esophageal Cancer 2015. Available from http seer (dot) cancer (dog) gov (slash) statfacts (slash) html (slash) esoph (dot) html. Accessed Feb. 25, 2016.

Naylor G M, Gotoda T, Dixon M, et al. Why does Japan have a high incidence of gastric cancer? Comparison of gastritis between UK and Japanese patients. Gut. 2006; 55(11): 1545-1552.

Neugat A I, Hayek H, Howe G. Epidemiology of gastric cancer. Semin Oncol 1996; 23:281-91.

Sequist L V, Cassier P, Varga A, et al. Phase I study of BGJ398, a selective pan FGFR inhibitor in genetically preselected advanced solid tumors. Proc AACR 2014: CT326 (abstract).

Shinkawa T, Nakamura k, Yamane N, Shoji-Hosaka E, Kanda Y et al. The absence of fucose but not the presence of galactose or bisecting N-acetylglucosamine of human IgG1 complex-type oligosaccharides shows the critical role of enhancing antibody-dependent cellular cytotoxicity. JBC, 2003; 278:3466-3473.

Takahashi T, Saikawa Y, Kitagawa Y. Gastric cancer: current status of diagnosis and treatment. Cancers 2013; 5(1): 48-63.

Thuss-Patience, P., A. Kretzschmar, D. Bichev, et al. Survival advantage for irinotecan versus best supportive care as second-line chemotherapy in gastric cancer-A randomised phase III study of the Arbeitsgemeinschaft Internistische Onkologie (AIO). Eur J Cancer 2011; 47:2306-2314.

Turner N, Grose R. Fibroblast growth factor signaling: from development to cancer. Nature, 2010; 10:116-129.

Ueda S, Hironaka S, Yasui H, et al. Randomized phase III study of irinotecan (CPT-11) versus weekly paclitaxel (wPTX) for advanced gastric cancer (AGC) refractory to combination chemotherapy (CT) of fluoropyrimidine plus platinum (FP): WJOG4007 trial, J Clin Oncol (Meeting Abstracts). 2012, vol. 3

Waddell T, Verheij M, Allum W, Cunningham D, Cervantes A, Arnold D. Gastric cancer: ESMO-ESSO-ESTRO Clinical Practice Guidelines for diagnosis, treatment and follow-up. Annals of Oncology. 2013 Oct. 1; 24(suppl 6):vi57-63.

Wu, Y-M, Su, F, Kalyana-Sundaram S, Identification of Targetable FGFR Fusions in Diverse Cancers. Cancer Discovery, 2013; 3:636-647.

LIST OF ABBREVIATIONS AND DEFINITIONS

| Abbreviation | Definition |
| --- | --- |
| ADCC | antibody-dependent cell-mediated cytotoxicity |
| AE | adverse event |
| AIDS | acquired immunodeficiency syndrome |
| ALT | alanine aminotransferase |
| ANC | absolute neutrophil count |
| AST | aspartate aminotransferase |
| AUC | area under serum concentration-time curve |
| $AUC_\tau$ | AUC at time τ |
| β-hCG | β-human chorionic gonadotropin |
| CHO | Chinese hamster ovary |

| Abbreviation | Definition |
| --- | --- |
| CI | confidence interval |
| CL | clearance |
| $C_{max}$ | maximum serum concentration |
| CNS | central nervous system |
| CRC | Cohort Review Committee |
| CRO | contract research organization |
| CT | computed tomography |
| CTCAE | Common Terminology Criteria for Adverse Events |
| ctDNA | circulating tumor DNA |
| $C_{trough}$ | trough serum concentration |
| $C_{trough\ ss}$ | trough concentration at steady state |
| DLT | dose-limiting toxicities |
| DMC | Data Monitoring Committee |
| DOR | duration of response |
| DPD | dipyrimidine dehydrogenase |
| EAP | etoposide/doxorubicin/cisplatin |
| ECF | epirubicin/cisplatin/5-FU |
| ECG | electrocardiogram |
| ECOG | Eastern Cooperative Oncology Group |
| eCRF | electronic case report forms |
| ELF | etoposide/leucovorin/5-FU |
| ELISA | enzyme linked immunosorbent assay |
| EORTC | European Organisation for Research and Treatment of Cancer |
| EOT | end of treatment |
| eSAE | electronic SAE reporting |
| 5-FU | 5-fluorouracil |
| FAM | 5-FU, 3 doxorubicin, and mitomycin C |
| FAMTX | 5-FU/doxorubicin [Adriamycin]/methotrexate) |
| FGF | fibroblast growth factor |
| FGFR | fibroblast growth factor receptor |
| FISH | fluorescent in situ hybridization |
| FP | 5-FU/cisplatin |
| FRS2 | FGF receptor substrate-2 |
| GC | gastric cancer |
| GCP | Good Clinical Practices |
| G-CSF | granulocyte-colony stimulating factor |
| GEJ | gastroesophageal junction |
| GI | gastrointestinal |
| GLP | GLP Good Laboratory Practices |
| HFc-G1 | human IgG1 |
| HIV | human immunodeficiency virus |
| HNSTD | highest, non-severely toxic dose |
| HR | hazard ratio |
| IB | Investigator's Brochure |
| ICF | informed consent form |
| ICH | International Conference on Harmonization |
| ID | identification |
| IEC | Independent Ethics Committee |
| IHC | immunohistochemistry |
| IND | investigational new drug |
| INR | international normalised ratio |
| IP | investigational product |
| IRB | Institutional Review Board |
| IRC | Independent Review Committee |
| ITT | intent-to-treat |
| IV | intravenous |
| IXRS | interactive voice and Web response system |
| LLOQ | lower limit of quantitation |
| LV | (remove) |
| mFOLFOX6 | modified FOLFOX (infusional 5-fluorouracil, leucovorin, and oxaliplatin) |
| mOS | Median OS |
| MRI | magnetic resonance imaging |
| MTD | maximum tolerated dose |
| MTX | (remove) |
| NCA | non-compartmental analysis |
| NCI | National Cancer Institute |
| OCT | ocular coherence tomography |
| ORR | objective response rate |
| OS | overall survival |
| PD | pharmacodynamic |
| PET | positron emission tomography |
| PFS | progression-free survival |
| PK | pharmacokinetic |
| PRO | patient reported outcomes |
| Q2W | twice weekly |
| QLQ | quality of life questionnaire |
| QOL | quality of life |
| RD | recommended dose |
| RECIST | Response Evaluation Criteria In Solid Tumors |
| RPE | retinal pigment epithelium |
| SAE | serious adverse event |
| SAP | statistical analysis plan |
| SD | standard deviation |
| t1/2 | terminal half-life |
| TEAE | treatment emergent adverse event |
| TKI | tyrosine kinase inhibitor |
| TS | thymidylate synthase |
| ULN | upper limit of normal |
| VAS | visual analogue scale |

TABLE 6

Anti-FGFR2-IIIb antibody Pharmacokinetic Parameter Estimates (mean ± SD) Using Non-Compartmental Analysis for Patients Enrolled in anti-FGFR2-IIIb antibody-001 Part 1 after First Dose

| Study Part | Dose (mg/kg) | # of Patients in study | $C_{max\ 1}$ (μg/mL) | $C_{max\ 1}$/Dose (μg/mL/mg) | $C_{trough\ 1}$ (μg/mL) | $AUC_{last}$ (day * μg/mL) | $AUC_{last}$/Dose (day * μg/mL)/mg) | t½ (day) |
| --- | --- | --- | --- | --- | --- | --- | --- | --- |
| 1A | 0.3 | 3 | 7.96 ± 1.15 | 0.278 ± 0.0511 | NC | 28.4 ± 9.36 | 0.976 ± 0.265 | 2.97 ± 0.510 |
| | 1 | 4 | 22.2 ± 6.13 | 0.248 ± 0.0876 | 3.57 ± 1.07$^a$ | 115 ± 36.2 | 1.29 ± 0.515 | 6.01 ± 0.646 |
| | 3 | 3 | 71.5 ± 18.2 | 0.312 ± 0.0654 | 12.8 ± 2.96 | 355 ± 82.5 | 1.55 ± 0.290 | 8.36 ± 0.816 |
| | 6 | 3 | 136 ± 17.2 | 0.287 ± 0.0279 | 19.2 ± 3.36 | 672 ± 83.5 | 1.43 ± 0.237 | 6.70 ± 0.831 |
| | 10 | 3 | 287 ± 7.23 | 0.410 ± 0.0321 | 43.5 ± 23.4 | 1316 ± 340 | 1.86 ± 0.412 | 7.80 ± 2.44 |
| | 15 | 3 | 393 ± 185 | 0.385 ± 0.149 | 56.4 ± 31.6 | 1711 ± 310 | 1.70 ± 0.146 | 6.08$^b$ |

TABLE 6-continued

Anti-FGFR2-IIIb antibody Pharmacokinetic Parameter Estimates
(mean ± SD) Using Non-Compartmental Analysis for Patients
Enrolled in anti-FGFR2-IIIb antibody-001 Part 1 after First Dose

| Study Part | Dose (mg/kg) | # of Patients in study | $C_{max\ 1}$ (μg/mL) | $C_{max\ 1}$/Dose (μg/mL/mg) | $C_{trough\ 1}$ (μg/mL) | $AUC_{last}$ (day * μg/mL) | $AUC_{last}$/Dose (day * μg/mL/mg) | $t_{1/2}$ (day) |
|---|---|---|---|---|---|---|---|---|
| 1B | 3 | 1 | 52.5 | 0.49 | 9.22 | ND | ND | ND |
|  | 6 | 1 | 77 | 0.232 | 21.6 | 529 | 1.59 | 11.7 |
|  | 10 | 6[c] | 163 ± 43.5 | 0.299 ± 0.0669 | 35.3 ± 14.5 | 885 ± 191 | 1.65 ± 0.406 | 6.97 ± 3.01[d] |

Note:
$C_{max\ 1}$ = maximum observed serum concentration post first dose;
$C_{max\ 1}$/Dose = $C_{max\ 1}$ normalized by dose administered;
$C_{trough\ 1}$ = Observed serumconcentration at the end of the first dose interval;
$AUC_{last}$ = area under the observed concentrating-time curve from the time of dosing to the last quantifiable concentration post first dose;
$AUC_{last}$/Dose = $AUC_{last}$ normalized by dose administered; and
$t_{1/2}$ = terminal half-life.
NC = A summary statistic that could not be reported as 2 out of 3 patients with $C_{trough\ 1}$ below LLOQ;
ND = A PK parameter that could not be accurately determined.
[a]n = 3. Data from1 patient could not be reported because the patient was terminated without data on C1D15 from the study;
[b]n = 2. Terminal phase was characterized for less than one half-life for 1 of 3 patients. Therefore, the data for this patient was excluded from summary statistics for half-life as stipulated in the data analysis plan;
[c]One of 6 patients in the study received a partial dose and parameters were omitted from summary statistics; and
[d]n = 3. Terminal phase was characterized for less than one half-life for 2 of 5 patients. Therefore, these patients were excluded from summary statistics for half-life as stipulated in the data analysis plan.

APPENDIX 1

Schedule of Assessments - Dose-Escalation Safety Run-in (Part 1) and Dose Expansion (Part 2)

| Procedure[a] | Pre-Screening (Part 2 Only) Not Applicable | Screening Day −14 to Day 0 Week 0 | Study Treatment: Cycles 1 and 2 | | | | Study Treatment: Cycle 3, Cycle 4 and Subsequent Cycles | | | Follow-up | |
|---|---|---|---|---|---|---|---|---|---|---|---|
| | | | Cycle 1 Day 1 Week 1 | Cycle 1 Day 2 Week 1 | Cycle 1 Day 3 Week 1 | Cycle 1 Day 8 Week 2 | Cycle 2 Day 1 Week 3 | Cycle 3[b] Day 1 ≥Week 4 | Cycle 4[c] Day 1 | Other | EOT[d] | Survival[e] |
| Pre-screening informed consent[f] | X | | | | | | | | | | | |
| IHC analysis of FGFR2b expression | X | | | | | | | | | | | |
| Sample for blood-based biopsy (ctDNA) assay | X[g] | | X[h] | | | | | X[h] | X[h] | X[h] | X[h] | |
| Informed Consent[i] | | X | | | | | | | | | | |
| Review/Confirm Eligibility Criteria | | X | X | | | | | | | | | |
| Medical/Oncology and Medication History | | X | X | | | | | | | | | |
| Tumor Tissue Collection[j] | | X | | | | | | | | | | |
| Demography/Baseline Characteristics | | X | | | | | | | | | | |
| Physical Examination[k,l] | | X | X | | | X | X | X | X | | X | |
| ECOG Performance Status | | X | | | | | | X[m] | | | X | |
| Patient Reported Outcomes (EQ-5D-5L and the EORTC QLQ-C30)[n] | | | X | | | | | X[k] | X[k] | | | |
| Vital Signs[o] | | X | X | X | X | X | X | X | X | | X | |
| 12-lead ECG[p] | | X | | | | | | | | X[q] | X | |
| Comprehensive Ophthalmologic Exam[r] | | X | | | | | | X[o] | | | X[q] | X |
| Slit Lamp Examination[s] | | | | | | | | X[s] | X[s] | | X | |
| Clinical Safety Laboratory Sampling[t] | | X | X | | | X | X | X | X | X | X | |
| Pregnancy Test[u] | | X | X | | | | | X | | | X | |
| Urinalysis[v] | | X | X | | | | | X | | X[q] | X | |
| Radiological/Tumor Scans[w] | | X | | | | | | X[x] | X[x] | X[x] | X[y] | |
| Randomization[z] | | X | | | | | | | | | | |

APPENDIX 1-continued

Schedule of Assessments - Dose-Escalation Safety Run-in (Part 1) and Dose Expansion (Part 2)

| | | | Study Treatment: Cycles 1 and 2 | | | | Study Treatment: Cycle 3, Cycle 4 and Subsequent Cycles | | | | |
|---|---|---|---|---|---|---|---|---|---|---|---|
| | Pre-Screening | | Cycle | Cycle | Cycle | Cycle 2 | | | | | |
| | (Part 2 Only) Not | Screening Day −14 | Cycle 1 | 1 Day 2 | 1 Day 3 | 1 Day 8 | Day 1 | Cycle $3^b$ | Cycle $4^c$ | | | |
| Procedure$^a$ | Applicable | to Day 0 Week 0 | Day 1 Week 1 | Week 1 | Week 1 | Week 2 | Week 3 | Day 1 ≥Week 4 | Day 1 | Other | EOT$^d$ | Survival$^e$ |
| Survival Assessment | | | | | | | | | | | | X |
| Fresh Tissue Biopsy$^{aa}$ | X | | | | | | | X$^{aa}$ | | X$^{aa}$ | | |
| Immunogenicity Sampling$^{bb}$ | | | X | | | | X$^{bb}$ | X$^{bb}$ | | | X | |
| Collection for FCGR Polymorphism$^{cc}$ | | | X | | | | | | | | | |
| Hair Follicle Samples$^{dd}$ | | | X | | | | | X$^{bb}$ | | | X | |
| PK Samples | | | X$^{ee}$ | X$^{ee}$ | X$^{ee}$ | X$^{ee}$ | X$^{ee}$ | X$^{ee}$ | X$^{ee}$ | | X$^{ee}$ | |
| Biomarker Assessment Sampling | | | X$^{ff}$ | X$^{ff}$ | | | X$^{ff}$ | X$^{ff}$ | | | X$^{ff}$ | |
| Open-label anti-FGFR2-IIIb antibody Administration | | | X$^{gg}$ | | | | X$^{gg}$ | X$^{gg}$ | X$^{gg}$ | | | |
| FOLFOX Administration | | X$^{hh}$ | X$^{ii}$ | X$^{ii}$ | X$^{ii}$ | | X | X | X | | | |
| Blinded anti-FGFR2-IIIb antibody/Placebo Administration | | | X$^{jj}$ | | | | X$^{jj}$ | X$^{jj}$ | X$^{jj}$ | | | |
| Adverse Events$^{kk}$ | | X | X_____X | | | | | | | | | |
| Concomitant Medications | | | X_____ | | | | | | | | | X |

$^a$Unless specified, procedure is to be completed within ±72 hours of scheduled time point and to be synchronized with the study treatment administration day.
$^b$And subsequent odd cycles from Cycle 3, unless otherwise noted.
$^c$And subsequent even cycles from Cycle 4, unless otherwise noted.
$^d$End of Treatment (EOT) assessments should be performed 28 (±3) days following the last study treatment administration
$^e$Patients in both Part 1 and Part 2 will undergo long-term follow-up for survival by clinic visit or by telephone approximately every 3 months ±28 days after the EOT visit until up to 24 months after the last patient is enrolled into the study, or until death, loss to follow-up, withdrawal of consent or study termination by the Sponsor (whichever occurs first).
$^f$Pre-screening ICF
$^g$Sample for blood-based biopsy (ctDNA) assay at Pre-screening for Part 2 only. Additional blood-based biopsy (ctDNA) samples are described in footnote h.
$^h$Samples for blood-based biopsy (ctDNA) assay: PART 1: Samples for blood-based biopsy (ctDNA) assay will be collected prior to the first dose of study drug (Cycle 1 Day 1) and analyzed retrospectively for FGFR2 amplification. PART 2: Blood samples for ctDNA assessment will be analyzed prospectively for FGFR2 amplification. In addition, blood-based biopsy (ctDNA) assays will be collected longitudinally every 6 weeks from the first dose for 24 weeks, and then approximately every 12 weeks thereafter, and analyzed retrospectively for FGFR2 amplification. A sample will also be collected at the EOT visit for all Part 2 patients.
$^i$Written, signed informed consent must be collected prior to any study-specific procedures. The most recent IRB/EC approved ICF must be signed.
$^j$Tumor tissue from archival or newly obtained material (if available/feasible) is required in Part 1 and Part 2. Refer to the Laboratory Manual for sample handling instructions.
$^k$Complete physical examination and height will be measured at Screening only. Limited physical examinations should be conducted, including examination of the oropharynx, thereafter.
$^l$After Cycle 1, the IP dose will be recalculated at each infusion visit only if weight has changed >10% from Cycle 1, Day 1.
$^m$ECOG Performance Status will be assessed at Cycle 3 Day 1 and Day 1 of every other subsequent cycle (odd cycles) until the EOT visit.
$^n$The EQ-5D-5L and the EORTC QLQ-C30 will be administered prior to dosing on Cycle 1 Day 1, Cycle 4 Day 1, Cycle 7 Day 1, Cycle 10 Day 1, Cycle 13 Day 1, and then every 12 weeks.
$^o$Vital signs (blood pressure, pulse, respiration, and temperature) are to be measured on Cycle 1 Day 1 at the following time points: pre-dose, and 0.5, 1, 2, and 4 hours from the start of the anti-FGFR2-IIIb antibody infusion in Part 1 or the blinded IP infusion in Part 2. On subsequent dosing days, pre-dose and at 0.5, 1, and 2 hours from the start of anti-FGFR2-IIIb antibody infusion in Part 1 or the blinded IP infusion in Part 2.
$^p$With patient resting for 5 minutes prior to recording.
$^q$If clinically indicated at any time.
$^r$Comprehensive ophthalmologic examinations (conducted at Screening, prior to Cycle 3 Day 1, and at the EOT visit only) include fundoscopic and slit lamp exam, ocular coherence tomography (OCT), visual acuity, completion of fluorescein staining score form, determination of intraocular pressure, and review of ocular/visual symptoms. The comprehensive ophthalmologic examination will be repeated at any point if changes in visual acuity or visual symptoms are reported by patients.
$^s$Slit lamp examinations without OCT for patients in Part 1 and for patients in Part 2 randomized to receive anti-FGFR2-IIIb antibody and FOLFOX 6; every 6 weeks after Cycle 2 Day 1 (prior to Cycle 3 Day 15, Cycle 5 Day 1, and Cycle 6 Day 15), and then every 12 weeks after Cycle 6 Day 15. Continue every 6-8 weeks if the patient has any persistent corneal findings.
$^t$Blood tests (evaluated by local laboratories) are listed in Appendix 2. Hematology and blood chemistry test results must be obtained within 72 hours of study drug administration on C1D1 to confirm eligibility. On dosing days, hematology and blood chemistry results must be available within 72 hours prior to dosing. Coagulation samples need to be obtained at baseline, at Cycles 1 through 4, and at any time clinically indicated (e.g., patients on anticoagulant therapy requiring close monitoring).
$^u$Serum β-hCG (evaluated by local laboratories) will be performed only on women of childbearing potential □ 72 hours prior to Cycle 1 Day 1 and at EOT. On dosing days of odd cycles (every other cycle), urine pregnancy results must be available within 72 hours prior to dosing.
$^v$Includes dipstick for protein, glucose, blood, pH, and ketones. If dipstick findings are abnormal, then a microscopic evaluation will be performed to assess the abnormal findings.
$^w$Tumor assessments should consist of clinical examination and appropriate imaging techniques (preferably CT scans with appropriate slice thickness per RECIST); other assessments (MRI, radiograph, PET, and ultrasound) may be performed if required. The same methods used to detect lesions at baseline are to be used to follow the same lesions throughout the clinical study. Screening tumor scan must be within 2 weeks of the start of treatment on Day 1.
$^x$Tumor scans to be performed at Screening (within 2 weeks of Cycle 1 Day 1 in Part 1 and Part 2) and within 7 days prior to the start of Cycle 4 Day 1, Cycle 7 Day 1, Cycle 10 Day 1, Cycle 13 Day 1, and then approximately every 12 weeks. If initial CR or PR is noted, confirmatory scans must be performed 4-6 weeks later. After discontinuation of study treatment for reasons other than progression or withdrawal of consent, tumor assessments will continue until the patient initiates additional anti-cancer therapy or progresses.
$^y$This scan can be omitted if the last scan was performed <6 weeks prior to EOT visit or if tumor progression was previously determined.
$^z$For Part 2 only
$^{aa}$A fresh biopsy at a primary tumor or metastatic tumor site is mandatory, as feasible, at Screening [at least 24 hours prior to dosing] and on-treatment within 7 days prior to Cycle 3 Day 1 [and at least 24 hours prior to dosing] for only up to 30 patients randomized into Part 2. (For patients who have had a biopsy acquired within the 12 weeks prior to enrollment, this sample may fulfill the requirement for a fresh pre-treatment biopsy provided adequate sample is available for PD analysis (a single paraffin-embedded block or approximately 10 slides). After consultation with the Sponsor, patients who have documented response may receive another biopsy within 28 (±7) days post tumor assessment and/or patients who have progression may receive another biopsy at the EOT visit. The post-response and post-progression biopsies are optional.
$^{bb}$Blood samples for anti-anti-FGFR2-IIIb antibody antibodies. Refer to Appendix 3 for collection times.

APPENDIX 1-continued

Schedule of Assessments - Dose-Escalation Safety Run-in (Part 1) and Dose Expansion (Part 2)

| | | Study Treatment: Cycles 1 and 2 | | | | | Study Treatment: Cycle 3, Cycle 4 and Subsequent Cycles | | | |
|---|---|---|---|---|---|---|---|---|---|---|
| | Pre-Screening | | | | | | | | | |
| | (Part 2 Only) Not | Screening Day −14 to Day 0 | Cycle 1 Day 1 | 1 Day 2 Week | 1 Day 3 Week | 1 Day 8 Week | Cycle 2 Day 1 Week | Cycle 3[b] Day 1 | Cycle 4[c] Day 1 | Other | Follow-up |
| Procedure[a] | Applicable | Week 0 | Week 1 | 1 | 1 | 2 | 3 | ≥Week 4 | | EOT[d] | Survival[e] |

[cc]FCGR polymorphism testing sample. Refer to Appendix 3 for collection times.
[dd]In Part 1 only, scalp or eyebrow hair follicle samples (approximately 10, if available) will be collected prior to dosing on Cycle 1 Day 1, Cycle 3 Day 1, and Cycle 5 Day 1, and at the EOT visit from all patients for whom sampling is possible.
[ee]Blood samples for PK analysis. Refer to Appendix 3 for collection times.
[ff]Blood samples for exploratory biomarker analysis (Parts 1 and 2). Refer to Appendix 3 for collection times.
[gg]Open-label anti-FGFR2-IIIb antibody will be administered only to patients enrolled into Part 1.
[hh]For Part 1, patients may have initiated mFOLFOX6 chemotherapy prior to study enrollment, and must be a candidate for at least 2 cycles of mFOLFOX6 chemotherapy to be eligible. For Part 2, patients are required to have completed 2 cycles of mFOLFOX6 chemotherapy prior to randomization.
[ii]FOLFOX is administered as a 46-hour continuous infusion.
[jj]Blinded IP (anti-FGFR-IIIb antibody/placebo) will be administered only to patients randomized into Part 2.
[kk]AE collection begins following signing of the ICF for Screening. Events reported prior to the first on-study infusion will be considered pretreatment events and reported on the Medical History page of the eCRF, unless they directly correlate to a study-related procedure. Adverse event reporting will continue until completion of the EOT visit or until 28 days after the last dose of study drug.

APPENDIX 2

Laboratory Evaluations
The following laboratory parameters will be determined in accordance with the Schedule of Assessments:

Hematology:
Complete blood cell (CBC) with differential:

| | |
|---|---|
| white blood cells (WBC) | platelets |
| ANC | hemoglobin |
| neutrophils (%) | hematocrit |
| eosinophils (%) | red blood cells (RBC) |
| basophils (%) | RBC indices: |
| lymphocytes (%) | mean corpuscular volume (MCV) |
| monocytes (%) | mean corpuscular hemoglobin (MCH) |
| | mean corpuscular hemoglobin concentration (MCHC) |

APPENDIX 2-continued

Laboratory Evaluations
The following laboratory parameters will be determined in accordance with the Schedule of Assessments:

Urinalysis:
Dipstick (appearance, color, pH, specific gravity, ketones, protein, glucose, bilirubin, nitrite, urobilinogen, and occult blood)
If dipstick is positive (2+ or greater) for blood or protein, perform a microscopic examination.

Clinical chemistry:

| | |
|---|---|
| Albumin | globulin |
| alkaline phosphatase | glucose |
| ALT (SGPT) | lactate dehydrogenase (LDH) |
| AST (SGOT) | phosphate |
| blood urea nitrogen (BUN) | potassium |
| calcium | sodium |
| chloride | total bilirubin |
| carbon dioxide ($CO_2$ [bicarbonate]) | total cholesterol |
| creatinine | total protein |
| direct bilirubin | uric acid |

APPENDIX 3

Study Flowchart for Pharmacokinetic, Immunogenicity, and Pharmacodynamic Blood Sample Collections for Part 2

| Study Cycle | Study Day | Time Point | Type of Sample |
|---|---|---|---|
| Cycle 1 | Day 1 (First Dose) | ≤4 hours Prior to infusion | anti-FGFR2-IIIb antibody PK (serum) ADA (serum) Hair Follicle (if available) Blood-based Biomarker (optional; whole blood) FCGR Polymorphism (optional; whole blood) Blood-based biopsy (ctDNA) |
| | | 5 minutes after end of infusion | anti-FGFR2-IIIb antibody PK (serum) |
| | | 1 hour after end of infusion (±5 minutes) | anti-FGFR2-IIIb antibody PK (serum) |
| | | 4 hours after end of infusion (±5 minutes) | anti-FGFR2-IIIb antibody PK (serum) |

APPENDIX 3-continued

Study Flowchart for Pharmacokinetic, Immunogenicity, and
Pharmacodynamic Blood Sample Collections for Part 2

| Study Cycle | Study Day | Time Point | Type of Sample |
|---|---|---|---|
| | Day 8 | 168 hours after infusion (±2 days) | anti-FGFR2-IIIb antibody PK (serum) |
| | Day 15 (Second Dose) | ≤4 hours Prior to infusion | anti-FGFR2-IIIb antibody PK (serum) |
| | | 5 minutes after end of infusion | anti-FGFR2-IIIb antibody PK (serum) |
| Cycle 2 through Cycle 5 | Day 1 (First Dose) | ≤4 hours Prior to infusion | anti-FGFR2-IIIb antibody PK (serum) ADA (serum) Hair Follicle at Cycle 2 and 3 only (if available) Blood-based Biomarker at Cycle 4 only (optional; whole blood) |
| | | 5 minutes after end of infusion | anti-FGFR2-IIIb antibody PK (serum) |
| | Day 15 (Second Dose) | ≤4 hours Prior to infusion | Blood-based Biomarker at Cycle 2 and 5 only (optional; whole blood) |
| Cycle 7 and Subsequent Cycles | Day 1 (First Dose) | ≤4 hours Prior to infusion | anti-FGFR2-IIIb antibody PK at odd cycles only (serum) ADA at odd cycles only (serum) Blood-based Biomarker at Cycle 7 and then every 12 weeks thereafter (optional; whole blood) |
| | | 5 minutes after end of infusion | anti-FGFR2-IIIb antibody PK at odd cycles only (serum) |
| End of Treatment Follow-up | Visit Date | During Visit | anti-FGFR2-IIIb antibody PK (serum) ADA (serum) Hair Follicle (if available) Blood-based Biomarker (optional; whole blood) |

APPENDIX 4

ECOG Performance Status

| Grade | Performance Status Criteria |
|---|---|
| 0 | Fully active, able to carry on all pre-disease activities without restriction. |
| 1 | Restricted in physically strenuous activity but ambulatory and able to carry out work of a light sedentary nature (light housework, office work). |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair. |

Example 2: A Phase 1/3 Study of an
Anti-FGFR2-IIIb Antibody Combined with
Modified FOLFOX6 Versus Modified FOLFOX6 in
Patients with Previously Untreated Advanced
Gastric and Gastroesophageal Cancer Protocol Synopsis This study is a variation of the study described in Example 1 herein, and is a multicenter study to evaluate the safety, tolerability, efficacy, PK, and PD of an anti-FGFR2-IIIb antibody in combination with mFOLFOX6. The study will include an open-label, Phase 1 safety run-in in patients with GI tumors (not FGFR2 selected) followed by a randomized, open-label Phase 3, in patients with FGFR2-selected GC (as determined by prospective IHC analysis of FGFR2b over-expression and/or a ctDNA blood assay demonstrating FGFR2 gene amplification). After an initial screening period, patients will be treated with mFOLFOX6 in combination with anti-FGFR2-IIIb antibody or mFOLFOX6 alone in 2 week cycles.

Phase 1: Dose-Escalation Safety Run-in

Phase 1 is an open-label dose-escalation of anti-FGFR2-IIIb antibody in combination with mFOLFOX6. Eligible patients will have unresectable locally advanced or metastatic GI cancer of any type and be candidates to receive at least 2 doses of mFOLFOX6 chemotherapy. FGFR2 status is not a requirement for enrollment. FGFR2 status will be tested retrospectively by IHC (if tissue is available) and a sample will be obtained for ctDNA blood assay.

Phase 1 consists of a minimum of 2 dosing cohorts of anti-FGFR2-IIIb antibody in combination with mFOLFOX6 to determine the RD of anti-FGFR2-IIIb antibody to be administered in combination with mFOLFOX6 in Phase 3. Patients may or may not have initiated or received prior mFOLFOX6 chemotherapy. There is no upper limit on the number of previous mFOLFOX6 doses that patients may have received.

Each patient enrolled will be observed for 28 days (DLT Period) starting on the first day (Cycle 1 Day 1 [Study Day 1]) of treatment with anti-FGFR2-IIIb antibody, for safety assessments, PK and occurrence of dose-limiting toxicities. Cohorts of patients will be treated with escalating doses of anti-FGFR2-IIIb antibody in combination with a standard dose of a chemotherapy regimen of mFOLFOX6 in 2 week cycles.

Anti-FGFR2-IIIb Antibody Administration

Anti-FGFR2-IIIb antibody IV is administered every 2 weeks on Day 1 of each cycle (2 weeks=1 cycle) and prior to mFOLFOX6 chemotherapy. Patients treated in Cohort 2 only will receive one additional dose of anti-FGFR2-IIIb antibody Day 8 of Cycle 1 (mFOLFOX6 will not be administered on this day). Anti-FGFR2-IIIb antibody will be administered as an approximately 30 minute IV infusion via a peripheral vein or central venous catheter. The IV administration set for anti-FGFR2-IIIb antibody infusion must contain a 0.22-µm in-line filter or a 0.22-µm syringe filter.

mFOLFOX6 Administration

Administration of mFOLFOX6 chemotherapy will also commence on Cycle 1 Day 1 (Study Day 1) of each treatment cycle 30 minutes after the end of the infusion of anti-FGFR2-IIIb antibody. mFOLFOX6 will be administered every 2 weeks as follows:

Day 1: Oxaliplatin 85 mg/m2 IV infusion over 120 minutes,

Day 1: Leucovorin 400 mg/m2 IV infusion over 120 minutes, can be administered concurrently with oxaliplatin if using a Y connector, if not using a Y connector administer sequentially, Day 1: Immediately after oxaliplatin and leucovorin, 5 FU 400 mg/m2 bolus over approximately 5 minutes, Day 1: Immediately after the 5-FU bolus, 5-FU 2400 mg/m2 as a continuous IV infusion over 46 hours.

After the 28 day DLT period, patients may have doses held or receive reduced doses of mFOLFOX6 or anti-FGFR2-IIIb antibody based on toxicity analysis. Premedication may be used at the discretion of the investigator per local standard of care.

Phase 1 Cohorts

In Phase 1, the first dose cohort of anti-FGFR2-IIIb antibody to be tested is at 6 mg/kg. The anticipated dose levels are:

Cohort 1: 6 mg/kg anti-FGFR2-IIIb antibody every 2 weeks;

Cohort 2: 15 mg/kg anti-FGFR2-IIIb antibody every 2 weeks; 1 dose of 7.5 mg/kg on Day 8 (Cycle 1 only);

Cohort 3 (if needed): 15 mg/kg anti-FGFR2-IIIb antibody every 2 weeks;

Cohort 4 (if needed): Dose level lower than Cohort 3 but higher than Cohort 1 to achieve tolerability with optimal target exposure.

If the first cohort at 6 mg/kg clears the 28-day DLT period, the second dose cohort at 15 mg/kg every 2 weeks with a dose of 7.5 mg/kg on Day 8 (Cycle 1 only) will be tested in a rolling-6 design and enroll 6 patients. Dose escalation decisions will be based on an assessment of DLTs, overall safety and tolerability. Dose escalation decisions will be made after the last patient enrolled in each cohort has completed the 28-day DLT Period (completion of 2 treatment cycles of anti-FGFR2-IIIb antibody and mFOLFOX6). Dose escalation decisions will be agreed upon by the Cohort Review Committee (CRC), consisting of the Sponsor and investigators. If ≥2 DLTs are observed in Cohort 2, a dose level between Cohorts 1 and 2 may be evaluated (Cohort 3) in a rolling 6 (15 mg/kg every 2 weeks) design. If ≥2 DLTs are observed in Cohort 3 a dose level lower than Cohort 3 but higher than Cohort 1 may be evaluated (Cohort 4) in a rolling 6 design. DLTs are defined as any of the following deemed by investigator as related to anti-FGFR2-IIIb antibody.

ANC<0.5×$10^9$/L>5 days' duration or febrile neutropenia (ie, ANC<1.0×$10^9$/L with a single temperature of >38.3° C., or fever ≥38° C. for more than 1 hour). Use of G-CSF is permitted per institutional standards Platelets<25×$10^9$/L or platelets<50×$10^9$/L with bleeding requiring medical intervention Prolonged (>3 days)<50×$10^9$/L platelets Grade 4 anemia (ie, life-threatening consequences; urgent intervention indicated)

Any Grade 2-3 ophthalmologic AE that does not resolve within 7 days

Grade 4 ophthalmologic AE

AST/ALT≥3×ULN and concurrent total bilirubin≥2× ULN not related to liver involvement with cancer Any non-hematological AE Grade 3 or greater (except nausea, vomiting, and diarrhea).

Grade 3 nausea, vomiting or diarrhea that does not resolve with supportive care in 72 hours Grade 3 laboratory values that are not of clinical significance per investigator and Sponsor agreement if they do not resolve within 72 hours.

Grade 4 nausea, vomiting or diarrhea

Any Grade 4 laboratory value

The following algorithm in Table 7 below will be used for dose dose escalation decisions:

TABLE 7

Algorithm for Dose Escalation

| Number of Patients with DLTs | Action |
|---|---|
| 0/3 | Open next cohort |
| 1/3 | Enroll 3 more patients in same cohort |
| ≥2/3 | Stop enrollment. If Cohort 1, then the study will be stopped. |
| 1/6 | Open next cohort |
| ≥2/6 | Stop enrolment at that level. If at Cohort 1, the study will end. If at Cohort 2 or 3, then Cohort 3 or 4 will open respectively and 6 patients will be enrolled. |

The RD of anti-FGFR2-IIIb antibody for Phase 3 will be identified by the CRC based on an evaluation of the overall safety, tolerability, and PK and will not exceed 15 mg/kg administered IV every 2 weeks with 1 dose of 7.5 mg/kg on Day 8 of Cycle 1 only. In determining the RD, the CRC will consider toxicities observed during the DLT evaluation period, any toxicities observed beyond the DLT evaluation period, as well as dose reductions and discontinuations of mFOLFOX6 or anti-FGFR2-IIIb antibody due to toxicities that do not meet the DLT criteria. Based on the totality of the data, the chosen RD of anti-FGFR2-IIIb antibody will be a dose that is not anticipated to lead to a decrease in the dose intensity of mFOLFOX6 to be administered. The RD, therefore, may or may not be the same as the identified maximum tolerated dose (MTD). For example, if the MTD is not reached, or if data from subsequent cycles of treatment from Phase 1 provide additional insight on the safety profile, then the RD may be a different, though not higher, dose than the MTD.

The MTD is defined as the maximum dose at which <33% of patients experience a DLT (dose limiting toxicity) during the DLT Period. If a DLT is observed in 1 of 3 patients in Cohort 1, then 3 additional patients will be enrolled at that dose level. Dose escalation may continue until 2 of 3 to 6 patients treated at a dose level experience a DLT (dose level not to exceed the highest dose level tolerated in Phase 1). The next lower dose will then be considered the MTD.

Study Design

Upon initiation of enrollment into Cohort 2 (15 mg/kg cohort every 2 weeks with 1 dose of 7.5 mg/kg on Day 8 [Cycle 1 only]), 6 patients will be enrolled to explore the safety and efficacy. The total enrollment for Phase 1 will be approximately 9 to 21 patients.

Any patient who does not receive the full number of doses of anti-FGFR2-IIIb antibody as defined by cohort and 2 full doses of mFOLFOX6 during the DLT Period due to a reason that is not a DLT or an AE related to anti-FGFR2-IIIb antibody, will be considered unevaluable and the patient will be replaced. The replaced patient may continue on study at the investigator's discretion and after discussion with the Sponsor. No additional doses of anti-FGFR2-IIIb antibody or more than 2 doses of mFOLFOX6 should be administered during the 28-day DLT Period. The doses of anti-FGFR2-IIIb antibody and mFOLFOX6 on Day 1 of Cycle 2 do not need to be synchronized. For example, if mFOLFOX6 is delayed due to an AE that is deemed related only to mFOLFOX6 and not to anti-FGFR2-IIIb antibody, anti-FGFR2-IIIb antibody should be administered as scheduled for Cycles 1 and 2 regardless of delays in the mFOLFOX6 dosing schedule.

Upon completion of the DLT Period, patients may continue receiving anti-FGFR2-IIIb antibody in combination with mFOLFOX6 at the investigator's discretion. Additional treatments may be administered every 2 weeks (1 cycle) until investigator-assessed radiographic or clinical disease progression, unacceptable toxicity, or until the patient meets any of the other protocol-specified withdrawal criteria.

In the event a cycle of mFOLFOX6 is delayed beyond 2 weeks due to chemotherapy-related toxicity during the first 3 cycles of treatment (42 days), anti-FGFR2-IIIb antibody should be administered on schedule (±3 days). After the first 3 cycles, anti-FGFR2-IIIb antibody may be delayed up to ±7 days to be synchronized with administered mFOLFOX6. There is no mandated maximum number of doses of anti-FGFR2-IIIb antibody or mFOLFOX6. Ongoing administration of the mFOLFOX6 regimen beyond the DLT Period will be according to the following schedule:

Starting dose for mFOLFOX6 includes 85 mg/m$^2$ of oxaliplatin, 400 mg/m$^2$ of calcium folinate (folinic acid), a 400 mg/m$^2$ bolus dose of 5-FU, and a 2400 mg/m$^2$ continuous infusion dose of 5-FU over 46 hours mFOLFOX6 regimen will be administered every 2 weeks (±3 days) until investigator-assessed radiographic disease progression (Phase 3 only), clinical disease progression (Phase 1 only), unacceptable toxicity, or the patient meets any of the other protocol-specified withdrawal criteria Day 1: Oxaliplatin 85 mg/m$^2$ IV infusion over 120 minutes Day 1: Leucovorin 400 mg/m$^2$ IV infusion over 120 minutes, can be administered concurrently with oxaliplatin if using a Y connector; if not using a Y connector administer sequentially Day 1: Immediately after oxaliplatin and leucovorin, 5 FU 400 mg/m$^2$ bolus over approximately 5 minutes Day 1: Immediately after the 5-FU bolus, 5-FU 2400 mg/m$^2$ as a continuous IV infusion over 46 hours.

Any modifications to the ongoing administration of mFOLFOX6 may occur under the following guidelines:

If there is a change in body weight of at least 10%, doses should be recalculated.

Counsel patients to avoid exposure to cold weather during and for approximately 72 hours after each infusion.

Correct hypokalemia and hypomagnesemia prior to initiating oxaliplatin.

Severe diarrhea, mucositis, and myelosuppression after 5-FU should prompt evaluation for dihydropyrimidine dehydrogenase deficiency.

Leucovorin dose is given for d,l-racemic mixture. Use half the dose for LEVO-leucovorin (1-leucovorin)

In the event that oxaliplatin administration is discontinued for any reason prior to disease progression, 5-FU/leucovorin therapy may continue on an every-2 week schedule until disease progression, unacceptable toxicity, or other cause for study withdrawal. In the case 5-FU/leucovorin therapy is discontinued then oxaliplatin must be discontinued.

Certain dose adjustments for mFOLFOX6 toxicity are shown in Table 8 below.

TABLE 8

Dose Reductions and Delays for mFOLFOX6 Chemotherapy

| Toxicity | Grade | Oxaliplatin | 5-FU/Leucovorin |
| --- | --- | --- | --- |
| Neurotoxicity | Persistent (≥1 cycle) Grade 2 Neurotoxicity | Decrease from 85 mg/m2 to 65 mg/m2* | No change |
| | Transient (>7 days and ≤14 days) Grade 3 Neurotoxicity | Decrease from 85 mg/m2 to 65 mg/m2* | No change |
| | Persistent (>1 cycle) ≥ Grade 3 Neurotoxicity or any Grade 4 Neurotoxicity | Discontinue | No change |
| Gastrointestinal | ≥Grade 3 (after prophylaxis) | Hold until toxicity is ≤Grade 1, decrease from 85 mg/m2 to 65 mg/m2* | Hold until toxicity is ≤Grade 1, decrease by 20%* |
| Hematologic | ≥Grade 3 platelets | Hold until platelets are ≥75,000 then decrease from 85 mg/m2 to 65 mg/m2* | Reduce by 20%* |

TABLE 8-continued

Dose Reductions and Delays for mFOLFOX6 Chemotherapy

| Toxicity | Grade | Oxaliplatin | 5-FU/Leucovorin |
|---|---|---|---|
| | ≥Grade 3 neutropenia | Hold until ANC is ≥1500, then decrease from 85 mg/m2 to 65 mg/m2* | Reduce by 20%* |
| Skin | ≥Grade 3 Hand/foot syndrome | Hold until 5-FU resumes, then no change | Hold until ≤Grade 1, then decrease by 20%* |
| Other | ≥Grade 3 | Hold until ≤Grade 1, then decrease from 85 mg/m2 to 65 mg/m2* | Hold until ≤Grade 1, then reduce by 20%* |
| Pharyngolaryngeal dysesthesia | Any | Stop infusion, then consider increase duration of infusion up to 6 hours | No change |
| Pneumonitis | Any | Hold, investigate; discontinue permanently if confirmed | |
| Hepatic Impairment | Bilirubin 1-2 X ULN | No change | No change, consider decrease by 20%* |
| | Bilirubin >2-4 X ULN and/or AST/ALT is 2-4 X ULN | No change | No change, consider decrease by 20% |
| | Bilirubin >4 X ULN and/or AST/ALT is >4 x ULN | Discontinue | Discontinue |
| Renal Impairment (Creatinine Clearance) | >50 mL/min | No change | No change |
| | 30 to <50 mL/min | No change, consider decrease to 65 mg/m2* | No change |
| | <30 mL/min | Discontinue | Decrease dose by 20%* |

*If toxicity recurs at the same grade level after dose reduction; consider permanent discontinuation. Note that if 5-FU is permanently discontinued, oxaliplatin and leucovorin should be permanently discontinued. (Adapted from Cheeseman 2002, Hochster 2008, Teva Parenteral Medicines Inc. 2016, Teva Parenteral Medicines Inc. 2014, Teva Pharmaceuticals USA 2012.)

In the Phase 1 portion of the study, if anti-FGFR2-IIIb antibody is permanently discontinued for any reason, the patient will undergo an end of treatment (EOT) follow-up visit approximately 28 days after the last dose of anti-FGFR2-IIIb antibody. No further follow-up will be conducted for these patients and the end of anti-FGFR2-IIIb antibody treatment follow-up visit is the end of study. If mFOLFOX6 is discontinued for any reason other than investigator-assessed progression or any of the other protocol-specified withdrawal criteria, anti-FGFR2-IIIb antibody may be continued as a single agent therapy at the investigator's discretion.

Phase 3 Randomized Open Portion

Enrollment into Phase 3 will begin when a RD for anti-FGFR2-IIIb antibody has been identified by the CRC, which will not exceed the highest dose level evaluated and tolerated in Phase 1. Patients may enroll into either Phase 1 or Phase 3, but may not enroll in both phases of the study. Opening the Phase 3 portion of the study for enrollment will be at the discretion of the Sponsor.

Eligibility for enrollment requires patients to have unresectable locally advanced or metastatic GC, be candidates for mFOLFOX6 chemotherapy as standard first line therapy, and have a tumor that is FGFR2 positive by a centrally performed IHC tissue test and/or ctDNA blood assay. A Pre-Screening Informed Consent Form (ICF) must be signed by the patients prior to submission of tissue (archival or fresh) and a blood sample for FGFR2 testing. As receiving results of the centralized FGFR2 testing may take approximately 2 weeks, patients are allowed to receive up to 1 dose of mFOLFOX6 during this interim time period (Pre-Screening Period) at the discretion of the investigator. This 1 dose of chemotherapy is not a requirement of the study and is not considered part of this clinical study.

Patients whose tumors test positive for FGFR2b by IHC and/or positive for FGFR2 gene amplification by ctDNA blood assay may consent to full study participation (sign the full study ICF) and enter the Screening Period. The time between signing the full study ICF and enrollment into the study is considered the Screening Period (up to 21 days). During the Screening Period, the patient will undergo protocol specified screening procedures to ensure all eligibility criteria are met.

The Phase 3 portion of the study is randomized, open-label and will enroll 548 FGFR2-selected GC patients randomized 1:1 to receive the RD of anti-FGFR2-IIIb antibody in combination with mFOLFOX6, versus mFOLFOX6 to evaluate the efficacy of the combination. Patients must receive first administration of study treatment within 3 days of randomization. Treatment arms consist of:

Arm 1: anti-FGFR2-IIIb antibody in combination with mFOLFOX6 administered every 2 weeks, or Arm 2: mFOLFOX6 administered every 2 weeks.

Discontinuation of any component of the study treatment (mFOLFOX6, a component of mFOLFOX6, or anti-FGFR2-IIIb antibody) for any reason other than disease progression does not mandate discontinuation of other components. The exception is the discontinuation of 5-FU for any reason, which requires discontinuation of oxaliplatin and leucovorin. Ongoing administration of the mFOLFOX6 regimen may be provided, as discussed above.

For the first 3 cycles of treatment, anti-FGFR2-IIIb antibody should be administered on schedule (±3 days) regardless of delays in mFOLFOX6 treatment. If mFOLFOX6 is delayed, then after the first 3 cycles of anti-FGFR2-IIIb antibody, anti-FGFR2-IIIb antibody may be delayed up to 7 days to be synchronized with mFOLFOX6 administration. Synchronization of administration of anti-FGFR2-IIIb antibody and mFOLFOX6 however is not a protocol requirement. If after 7 days the patient is still unable to receive mFOLFOX6, IMP should continue as monotherapy every 2 weeks (±3 days).

Patients who discontinue all study treatment (all components of anti-FGFR2-IIIb antibody and mFOLFOX6) for any reason other than consent withdrawal will undergo an EOT safety follow-up visit approximately 28 days after the last dose of the last administered component of treatment (oxaliplatin, leucovorin, 5-FU, or anti-FGFR2-IIIb antibody).

However, patients who discontinue study treatment (anti-FGFR2-IIIb antibody and/or mFOLFOX6) for reasons other than disease progression or withdrawal of consent will continue to undergo tumor assessments according to the protocol schedule until radiographic progression or the initiation of additional anti-cancer therapy, at which point they would undergo long-term follow-up for survival.

Long-term follow-up for survival will be completed by clinic visit, telephone call or by using patient registries (in line with national legislation and prevailing data protection laws) approximately every 3 months (±1 month) after the EOT visit until up to 24 months after the last patient is enrolled into the study, or until death, loss to follow-up, withdrawal of consent or study termination by the Sponsor (whichever occurs first).

Inclusion Criteria for Phase 1 and Phase 3

Patients enrolling into either Phase 1 or Phase 3 of the study must meet all of the following inclusion criteria:
- Disease that is unresectable, locally advanced, or metastatic
- Understand and sign an Institutional Review Board (IRB)/Independent Ethics Committee (IEC)-approved informed consent form (ICF) prior to any study-specific evaluation
- Life expectancy of at least 3 months in the opinion of the investigator
- Eastern Cooperative Oncology Group (ECOG) performance status of 0 to 1
- Age≤18 years at the time the ICF is signed
- Negative serum β-human chorionic gonadotropin (β-hCG) pregnancy test≤96 hours prior to treatment (women of childbearing potential only) on Cycle 1, Day 1
- In sexually active patients (women of child bearing potential and males), willingness to use 2 effective methods of contraception, of which 1 must be a physical barrier method (condom, diaphragm, or cervical/vault cap) until 6 months after the last dose of anti-FGFR2-IIIb antibody. Other effective forms of contraception include:
- Permanent sterilization (hysterectomy and/or bilateral oophorectomy, or bilateral tubal ligation with surgery, or vasectomy) at least 6 months prior to Screening
- Women of childbearing potential who are on stable oral contraceptive therapy or intrauterine or implant device for at least 90 days prior to the study, or abstain from sexual intercourse as a way of living
- Adequate hematological and biological function, confirmed by the following laboratory values within 96 hours of Cycle 1 Day 1.

Bone Marrow Function
Absolute neutrophil count (ANC)≥1.5×10$^9$/L
Platelets≥100×10$^9$/L
Hemoglobin≥9 g/dL Hepatic Function
Aspartate aminotransferase (AST) and alanine aminotransferase (ALT)<3×upper limit of normal (ULN); if liver metastases, then <5×ULN
Bilirubin<1.5×ULN Renal Function
Calculated creatinine clearance using Cockroft Gault formula≥50 mL/min.
Patients on full-dose anticoagulants must be on a stable dose of warfarin for 6 weeks prior to enrollment and have an international normalised ratio (INR) within the therapeutic range for the patient's condition or be on a stable dose of low molecular weight heparin
Measurable or non-measurable disease
Patients enrolling into Phase 1 of the study must also meet the following inclusion criteria:
Histologically or cytologically confirmed GI malignancy for which mFOLFOX6 is considered an appropriate treatment (e.g., GC, colorectal carcinoma, pancreatic adenocarcinoma)
Tumor tissue (if available) for determination of FGFR2b overexpression by IHC retrospectively
Patient must be a candidate to receive at least 2 doses of mFOLFOX6 chemotherapy, with doses given as follows and subject to the toxicity guidelines provided above:
  Administration of mFOLFOX6 chemotherapy will commence on Cycle 1 Day 1 (Study Day 1) of each treatment cycle 30 minutes after the end of the infusion of anti-FGFR2-IIIb antibody/mFOLFOX6 is administered every 2 weeks as follows:
  Day 1: Oxaliplatin 85 mg/m$^2$ IV infusion over 120 minutes.
  Day 1: Leucovorin 400 mg/m$^2$ IV infusion over 120 minutes, can be administered concurrently with oxaliplatin if using a Y connector. If a Y connector is not available, administer sequentially.
  Day 1: Immediately after oxaliplatin and leucovorin, 5 FU 400 mg/m$^2$ bolus over approximately 5 minutes.
  Day 1: Immediately after the 5-FU bolus, 5-FU 2400 mg/m$^2$ as a continuous IV infusion over 46 hours. After the first dose, patients may receive dose reductions, delays, or discontinuation based on toxicity as per guidelines.
Patients enrolling into Phase 3 of the study must also meet the following inclusion criteria:
Histologically documented gastric or gastroesophageal junction (defined as 5 cm proximal and distal to the GEJ) adenocarcinoma
Radiographic imaging of the chest, abdomen and pelvis (computed tomography (CT) preferred, magnetic resonance imaging (MRI) acceptable) performed within 28 days of C1D1
Tumor tissue for FGFR2b overexpression as determined by a centrally performed IHC test and/or FGFR2 gene amplification as determined by a centrally performed ctDNA blood based assay
Patient must be a candidate for mFOLFOX6 chemotherapy
No prior chemotherapy for metastatic or unresectable disease (except a maximum of 1 dose of mFOLFOX6 administered while waiting for results of FGFR2 testing during the pre-screening period)
No prior platinum-based chemotherapy (except as noted in the Inclusion Criterion #18)

If prior adjuvant or neo-adjuvant therapy (chemotherapy and/or chemoradiation) has been received, more than 6 months must have elapsed between the end of adjuvant therapy and enrollment Exclusion Criteria for Phase 1 and Phase 3

Patients enrolling into either Phase 1 or Phase 3 will be excluded if any of the following criteria apply:

Untreated or symptomatic central nervous system (CNS) metastases (CNS imaging not required). Patients with asymptomatic CNS metastases are eligible provided they have been clinically stable for at least 4 weeks and do not require intervention such as surgery, radiation, or any corticosteroid therapy for management of symptoms related to CNS disease Impaired cardiac function or clinically significant cardiac disease, including any of the following:
Unstable angina pectoris≤6 months prior to enrollment
Acute myocardial infarction≤6 months prior to enrollment
New York Heart Association class II-IV congestive heart failure
Uncontrolled hypertension (as defined as ≥160/90 despite optimal medical management)
Uncontrolled cardiac arrhythmias requiring anti-arrhythmic therapy other than beta blockers or digoxin
Active coronary artery disease
QTcF≥480

Peripheral sensory neuropathy Common Terminology Criteria for Adverse Events (CTCAE) Grade 2

Active infection requiring systemic treatment or any uncontrolled infection 14 days prior to enrollment Known human immunodeficiency virus (HIV) or acquired immunodeficiency syndrome (AIDS)-related illness, or known active or chronic hepatitis B or C infection History of interstitial lung disease (eg, pneumonitis or pulmonary fibrosis)

Evidence or history of bleeding diathesis or coagulopathy

Radiotherapy≤28 days of enrollment. Patients must be recovered from all acute radiotherapy-related toxicities. No radiopharmaceuticals (strontium, samarium) within 8 weeks of enrollment Prior treatment with any selective inhibitor (eg, AZD4547, BGJ398, JNJ-42756493, BAY1179470) of the FGF-FGFR pathway Ongoing adverse effects from prior systemic treatment>NCI CTCAE Grade 1 (with the exception of Grade 2 alopecia)

Participation in another therapeutic clinical study or receiving any investigational agent within 28 days of enrollment or during this clinical study Corneal defects, corneal ulcerations, keratitis, keratoconus, history of corneal transplant, or other known abnormalities of the cornea that may pose an increased risk of developing a corneal ulcer Known positivity for HER2 (as defined by a positive IHC test of 3+ or IHC of 2+ with positive FISH)

Major surgical procedures are not allowed ≤28 days prior to enrollment. Surgery requiring local/epidural anesthesia must be completed at least 72 hours before enrollment. In all cases the patient must be sufficiently recovered and stable before treatment administration Women who are pregnant or breastfeeding (unless the patient is willing to interrupt breastfeeding during study treatment administration and then resume 6 months after study discontinuation); women of childbearing potential must not consider getting pregnant during the study Presence of any serious or unstable concomitant systemic disorder incompatible with the clinical study (eg, substance abuse, psychiatric disturbance, or uncontrolled intercurrent illness including arterial thrombosis, and symptomatic pulmonary embolism)

Presence of any other condition that may increase the risk associated with study participation, or may interfere with the interpretation of study results, and, in the opinion of the investigator, would make the patient inappropriate for entry into the study Known allergy or hypersensitivity to components of the anti-FGFR2-IIIb antibody formulation including polysorbate or to platinum-containing medications, 5-FU, or leucovorin History of prior malignancy, except:
Curatively treated non-melanoma skin malignancy
Cervical cancer in situ
Curatively treated ductal or lobular breast carcinoma in situ and not currently receiving any systemic therapy
Solid tumor treated curatively more than 5 years previously without evidence of recurrence.

No waivers of these inclusion or exclusion criteria will be granted.

Study Treatment

In Phase 1, anti-FGFR2-IIIb antibody will be supplied in a sterile vial for dilution into an intravenous (IV) bag for administration by the study site over approximately 30 minutes (±10 minutes) every 2 weeks (±3 days) prior to administration of mFOLFOX6 chemotherapy. Only patients treated in Cohort 2 will receive 1 additional dose of anti-FGFR2-IIIb antibody on Day 8 of Cycle 1. Starting on Cycle 2 all patients will receive anti-FGFR2-IIIb antibody every 2 weeks on Day 1 of each cycle until investigator-assessed radiographic or clinical disease progression, unacceptable toxicity, or the patient meets any of the other protocol-specified withdrawal criteria. The IV administration set for FP144 infusion must contain a 0.22 µm in-line filter or a 0.22 µm syringe filter.

In Phase 3, anti-FGFR2-IIIb antibody will be prepared and administered in a similar fashion to anti-FGFR2-IIIb antibody in Phase 1. Administration of anti-FGFR2-IIIb antibody will continue until investigator-assessed radiographic or clinical progression, unacceptable toxicity, or the patient meets any of the other protocol-specified criteria.

Oxaliplatin, 5-FU, and leucovorin (mFOLFOX6) will be administered by each site (as described above) every 2 weeks (±7 days).

Pharmacokinetic Assessments

Blood samples will be collected at specific time points to measure serum levels of anti-FGFR2-IIIb antibody in all enrolled patients in Phase 1 and Phase 3, respectively.

PK parameters will be estimated using non-compartmental analysis, though compartment analysis may be employed if appropriate. Serum concentration-time data from this clinical trial will be pooled with data from other studies for integrated population PK analysis and exposure-response relationship assessment.

Immunogenicity Assessments

For all enrolled patients in Phase 1 and Phase 3, blood samples will be collected for anti-(anti-FGFR2-IIIb antibody)-antibodies. Immunogenicity, defined as an immune response to anti-FGFR2-IIIb antibody, will be assessed by measurement of total antibodies against anti-FGFR2-IIIb antibody from all patients. Immunogenicity testing will consist of screening, confirmation, and titration. Additional characterization of a confirmed antibody response against anti-FGFR2-IIIb antibody may be considered.

Efficacy Assessments

During Phase 3, tumor response assessment will be performed by the investigator per RECIST v.1.1 guidelines. Efficacy measures will include tumor assessments consisting of clinical examination and appropriate imaging techniques, preferably CT scans of the chest, abdomen, and pelvis with appropriate slice thickness per RECIST v1.1 guidelines, but MIII acceptable. Scans will be done during the screening window (within 21 days of Cycle 1 Day 1). A scan performed prior to Screening as part of standard of care, performed no greater than 28 days prior to enrollment is acceptable. Scans will be performed every 8 weeks (±7 days) from Cycle 1 Day 1.

Safety Assessments

Safety measures will include AEs, hematology, clinical chemistry, urinalysis, vital signs, body weight, concomitant medications/procedures, ECOG performance status, targeted physical examinations, ECGs, and ophthalmology examinations in both Phase 1 and Phase 3.

Pharmacodynamic Assessments

Phase I

PD assessments will be collected at specific time points. Tumor tissue submitted for evaluation of FGFR2 status, if available, will be retrospectively analyzed for FGFR2b overexpression using IHC. Blood samples submitted for evaluation of FGFR2 status will be collected prior to the first dose of study treatment and analyzed retrospectively for FGFR2 gene amplification using a ctDNA blood assay. Blood samples for exploratory biomarker analysis of the FGFR pathway will be collected longitudinally.

Phase 3

Tumor tissue will be submitted for evaluation of FGFR2 status and will be prospectively analyzed for FGFR2b overexpression using IHC. Blood samples will be submitted for evaluation of FGFR2 status and will be prospectively analyzed for FGFR2 gene amplification using a ctDNA blood assay. Positive results from either tissue or blood, but not both, must be available prior to enrollment.

The total enrollment planned for this study is approximately 569 patients. Approximately 9-21 patients evaluable for any dose limiting toxicity will be enrolled into Phase 1. For Phase 3, efficacy and tolerability will be evaluated by enrollment of approximately 548 patients with FGFR2-selected GC, randomized 1:1 to receive anti-FGFR2-IIIb antibody in combination with mFOLFOX6, or mFOLFOX6 alone. Eligible patients will be stratified by geographic region (US and EU vs Japan vs Rest of Asia [including China] vs Rest of World), prior treatment status (de novo vs adjuvant/neo-adjuvant), and administration of a single dose of mFOLFOX6 prior to enrollment (yes or no).

In Phase 1, all analyses will be descriptive and will be presented by dose group and overall as appropriate. Descriptive statistics will include number of observations, mean, standard deviation, median, range, and inter-quartile range for continuous variables, and the number and percent for categorical variables; 95% confidence intervals will be presented where appropriate. Additionally, incidence of TEAEs leading to dosing reductions or dose discontinuation will be tabulated and summarized. In Phase 3, the primary efficacy analysis is the comparison of OS between patients treated with anti-FGFR2-IIIb antibody in combination with mFOLFOX6 and those treated with mFOLFOX6.

The primary endpoint, OS, is defined as time from randomization until death from any cause. The secondary efficacy endpoints include PFS and ORR, whereas PFS is defined as time from randomization until the date of radiological or clinical disease progression based on investigator-assessment (per RECIST v.1.1) or death from any cause, whichever comes first, and ORR is defined as the proportion of patients with baseline measurable disease and a partial or complete response as determined by the investigator per RECIST v.1.1.

This Phase 3 study is designed to assess the hazard ratio (HR) for overall survival (OS) for the combination of anti-FGFR2-IIIb antibody and mFOLFOX6 compared with mFOLFOX6 alone. 374 primary death events may provide 80% power to detect a HR of 0.75 for OS, using a Cox regression analysis having (one-sided) false positive error rate of 2.5%. Assuming an exponential distribution of OS, this will correspond approximately to an increase of 33% in median survival from 10 months to 13.3 months. Statistical significance for OS will occur with an estimated HR=0.815, corresponding approximately to an increase of 22.6% in median survival from 10 months to 12.26 months.

Approximately 548 patients will be randomized (1:1) during 44 months of accrual, with approximately 24 additional months follow-up in order to achieve the targeted number of primary events.

The hypothesis of OS will be tested first. There will be two interim analyses and a primary analysis for OS and all are event-based analyses.

Two interim analyses for OS are planned; the first after 50% of OS events (approximately 187 events) and the second after 75% of OS events (approximately 281 events). The O'Brien-Fleming monitoring boundary will be used to preserve the 2.5% false-positive error rate, with a Lan-DeMets implementation to allow flexibility in the number and timing of these interim analyses.

The primary analysis of OS will be performed using the intent-to-treat (ITT) population, and will be conducted using a stratified log-rank test. The stratification factors will be the same used to stratify the randomization schedule as documented in the interactive voice and Web response system (IXRS).

The median OS and the associated 95% confidence interval for each treatment arm will be estimated using the Kaplan-Meier method. The hazard ratio (HR=$\lambda_{ANTI\text{-}FGFR2\text{-}IIIB\ ANTIBODY+\ mFOLFOX6}/\lambda_{mFOLFOX6}$) will be estimated using a Cox regression model with treatment group as the only main effect and stratifying by the same stratification factors as were used for the stratified log-rank test. An unstratified HR will also be presented.

Analyses of secondary endpoints PFS and ORR will be conducted hierarchically if the analysis of the primary endpoint, OS is statistically significant. The formal hypotheses regarding effects on PFS and ORR will be tested hierarchically at a level of 0.05. The PFS will be tested first and if it is significant, the ORR will be tested next. The family-wise type I error rate of testing primary and secondary endpoints will be in a control by employing this gate-keeping testing procedure at a level of 0.05.

If the testing for OS is significant, we will then test progression-free survival (PFS) using a stratified log-rank test at a level of 0.05 based on all PFS events observed at the time of performing OS analysis. The primary analysis of PFS will be conducted using a stratified log-rank test (2-sided). The stratification factors will be the same used to stratify the randomization schedule as documented in the interactive voice and Web response system (IXRS).

The median PFS and the associated 95% confidence interval for each treatment arm will be estimated using the Kaplan-Meier method. The HR will be estimated using a Cox regression model with treatment group as the only main effect and stratifying by the same stratification factors as were used for the stratified log-rank test. An unstratified HR will also be presented. The PFS analysis will be conducted on the ITT population.

If the testing for PFS is significant, then the analysis of ORR will be performed among the patients with baseline measurable disease. In the analysis of ORR, patients who don't have any post-baseline adequate tumor assessments will be counted as non-responders. Formal hypothesis testing of ORR will be performed using the stratified Cochran-Mantel-Haenszel test (2-sided) at a level of 0.05. The stratification factors will be the same used to stratify the randomization schedule as documented in the IXRS.

Safety Analysis: All AEs will be coded using the Medical Dictionary for Regulatory Activities (MedDRA). The investigator will classify the severity of AEs using the CTCAE v 4.03. A treatment emergent adverse event (TEAE) is defined as any event with an onset date on or after date of first dose of study treatment, or any event present before treatment that worsens after treatment. Only TEAEs with an onset date prior to date of last dose+28 days will be tabulated in summary tables.

Clinical laboratory data will be summarized by the type of laboratory test. The number and percentage of patients who experience abnormal (ie, outside of reference ranges) and/or clinically significant abnormalities after study treatment administration will be presented for each clinical laboratory measurement. For each clinical laboratory measurement, descriptive statistics will be provided for baseline and all subsequent post-treatment scheduled visits. Changes from baseline to the post-treatment visits will also be provided. Descriptive statistics of vital signs will also be provided in a similar manner. In addition, shift from baseline in CTCAE grade (where applicable) and by high/low flags (where CTCAE grades are not defined) will be presented in a similar manner.

Safety analyses for Phase I will be performed for patients included in the safety population. The incidence of DLTs, incidence of TEAEs, clinical laboratory abnormalities (e.g., shift table), vital signs, corneal and retinal findings, and ECGs will be tabulated and summarized by dose level. Additionally, incidence of TEAEs leading to dosing reduction or dose discontinuation will be tabulated and summarized.

The analyses of safety for Phase 3 will include all patients who receive any study treatment (anti-FGFR2-IIIb antibody in combination with mFOLFOX6, or mFOLFOX6) throughout the study and will provide any post-treatment safety information. The incidence of TEAEs, clinical laboratory abnormalities, vital signs, corneal and retinal findings, and ECGs will be tabulated and summarized by treatment group.

Individual and mean (±SD) serum anti-FGFR2-IIIb antibody concentration-time data will be tabulated and plotted by dose level. PK parameters will be tabulated and summarized by dose level when appropriate and applicable. The impact of immunogenicity on anti-FGFR2-IIIb antibody exposure will be assessed, tabulated, and summarized by dose level as data allow. Integrated population PK analysis and exposure-response relationship assessment will be presented in a separate report.

Figure 3:
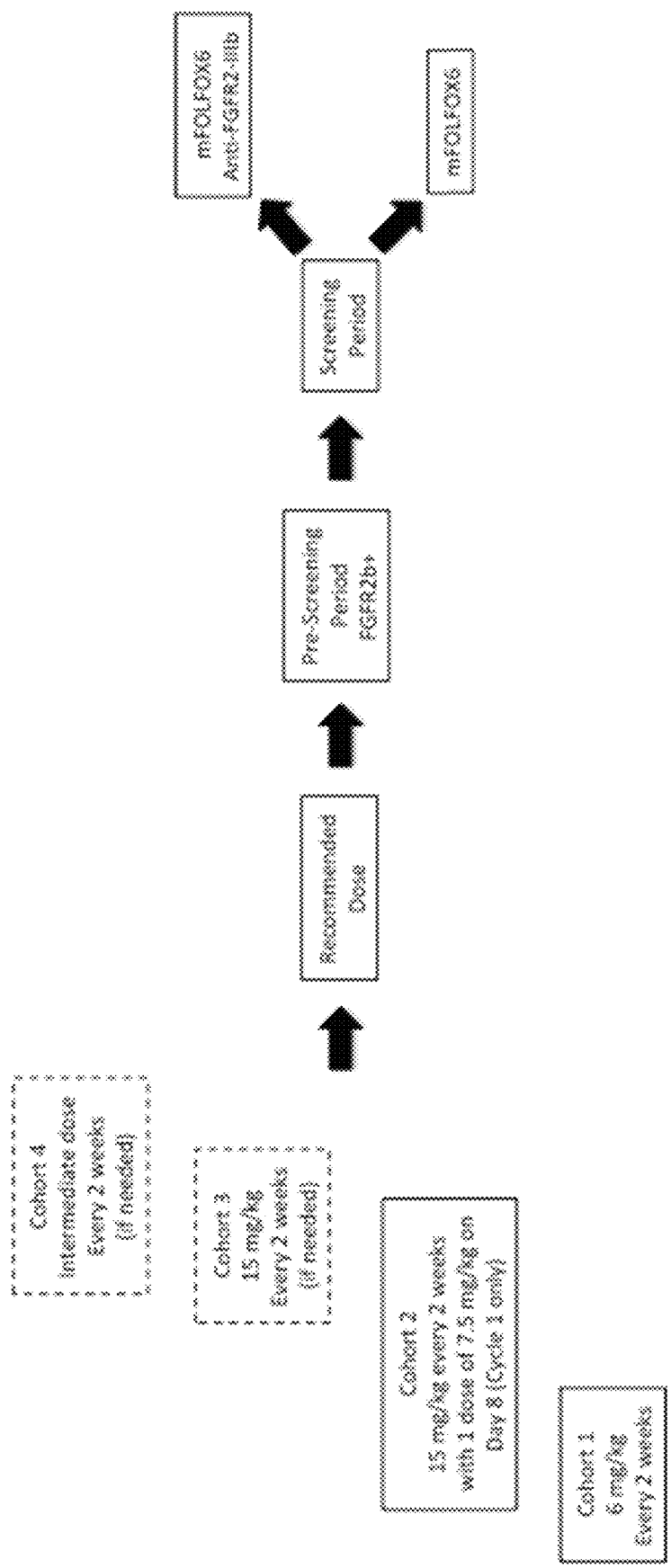
FIG. 3 shows administration schedules for the dose escalation (phase 1) of the clinical trial described in Example 2. The initial cohorts are cohorts 1 and 2, with cohort 3 opened if needed and a further cohort 4 (not shown) also opened if needed. Further details are provided in Example 2 below.

A schematic depiction of the study cohorts is provided in FIG. 3.

TABLE OF SEQUENCES
The table below provides a listing of certain sequences referenced herein.

| SEQ. ID. NO. | Description | Sequence |
|---|---|---|
| 1 | Mature human FGFR2-IIIb | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKHSGINSS NAEVLALFNV TEADAGEYIC KVSNYIGQAN QSAWLTVLPK QQAPGREKEI TASPDYLEIA IYCIGVFLIA CMVVTVILCR MKNTTKKPDF SSQPAVHKLT KRIPLRRQVT VSAESSSSMN SNTPLVRITT RLSSTADTPM LAGVSEYELP EDPKWEFPRD KLTLGKPLGE GCFGQVVMAE AVGIDKDKPK EAVTVAVKML KDDATEKDLS DLVSEMEMMK MIGKHKNIIN LLGACTQDGP LYVIVEYASK GNLREYLRAR RPPGMEYSYD INRVPEEQMT FKDLVSCTYQ LARGMEYLAS QKCIHRDLAA RNVLVTENNV MKIADFGLAR DINNIDYYKK TTNGRLPVKW MAPEALFDRV YTHQSDVWSF GVLMWEIFTL GGSPYPGIPV EELFKLLKEG HRMDKPANCT NELYMMMRDC WHAVPSQRPT FKQLVEDLDR ILTLTTNEEY LDLSQPLEQY SPSYPDTRSS CSSGDDSVFS PDPMPYEPCL PQYPHINGSV KT |
| 2 | Anti-FGFR2b heavy chain; Asn297 is in bold and underlined | QVQLVQSGAE VKKPGSSVKV SCKASGYIFT TYNVHWVRQA PGQGLEWIGS IYPDNGDTSY NQNFKGRATI TADKSTSTAY MELSSLRSED TAVYYCARGD FAYWGQGTLV TVSSASTKGP SVFPLAPSSK STSGGTAALG CLVKDYFPEP VTVSWNSGAL TSGVHTFPAV LQSSGLYSLS SVVTVPSSSL GTQTYICNVN HKPSNTKVDK RVEPKSCDKT HTCPPCPAPE LLGGPSVFLF PPKPKDTLMI SRTPEVTCVV VDVSHEDPEV KFNWYVDGVE VHNAKTKPRE EQY<u>N</u>STYRVV SVLTVLHQDW LNGKEYKCKV SNK<u>A</u>LPAPIE KTISKAKGQP REPQVYTLPP SREEMTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 3 | Anti-FGFR2b light chain | DIQMTQSPSS LSASVGDRVT ITCKASQGVS NDVAWYQQKP GKAPKLLIYS ASYRYTGVPS RFSGSGSGTD FTFTISSLQP EDIATYYCQQ HSTTPYTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 4 | Anti-FGFR2b heavy chain variable region | QVQLVQSGAE VKKPGSSVKV SCKASGYIFT TYNVHWVRQA PGQGLEWIGS IYPDNGDTSY NQNFKGRATI TADKSTSTAY MELSSLRSED TAVYYCARGD FAYWGQGTLV TVSS |
| 5 | Anti-FGFR2b light chain variable region | DIQMTQSPSS LSASVGDRVT ITCKASQGVS NDVAWYQQKP GKAPKLLIYS ASYRYTGVPS RFSGSGSGTD FTFTISSLQP EDIATYYCQQ HSTTPYTFGQ GTKLEIK |
| 6 | Anti-FGFR2b heavy chain (HC) HVR1 | TYNVH |
| 7 | Anti-FGFR2b HC HVR2 | SIYPDNGDTS YNQNFKG |
| 8 | Anti-FGFR2b HC HVR3 | GDFAY |

TABLE OF SEQUENCES
The table below provides a listing of certain sequences referenced herein.

| SEQ. ID. NO. | Description | Sequence |
|---|---|---|
| 9 | Anti-FGFR2b light chain (LC) HVR1 | KASQGVSNDVA |
| 10 | Anti-FGFR2b LC HVR2 | SASYRYT |
| 11 | Anti-FGFR2b LC HVR3 | QQHSTTPYT |
| 12 | Anti-FGFR2b N297Q heavy chain; the N297Q point mutation is bold and underlined | QVQLVQSGAE VKKPGSSVKV SCKASGYIFT TYNVHWVRQA PGQGLEWIGS IYPDNGDTSY NQNFKGRATI TADKSTSTAY MELSSLRSED TAVYYCARGD FAYWGQGTLV TVSSASTKGP SVFPLAPSSK STSGGTAALG CLVKDYFPEP VTVSWNSGAL TSGVHTFPAV LQSSGLYSLS SVVTVPSSSL GTQTYICNVN HKPSNTKVDK RVEPKSCDKT HTCPPCPAPE LLGGPSVFLF PPKPKDTLMI SRTPEVTCVV VDVSHEDPEV KFNWYVDGVE VHNAKTKPRE EQYQSTYRVV SVLTVLHQDW LNGKEYKCKV SNKALPAPIE KTISKAKGQP REPQVYTLPP SREEMTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 13 | Mature human FGFR2-IIIc | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPDYLEIAI YCIGVFLIAC MVVTVILCRM KNTTKKPDFS SQPAVHKLTK RIPLRRQVTV SAESSSSMNS NTPLVRITTR LSSTADTPML AGVSEYELPE DPKWEFPRDK LTLGKPLGEG CFGQVVMAEA VGIDKDKPKE AVTVAVKMLK DDATEKDLSD LVSEMEMMKM IGKHKNIINL LGACTQDGPL YVIVEYASKG NLREYLRARR PPGMEYSYDI NRVPEEQMTF KDLVSCTYQL ARGMEYLASQ KCIHRDLAAR NVLVTENNVM KIADFGLARD INNIDYYKKT TNGRLPVKWM APEALFDRVY THQSDVWSFG VLMWEIFTLG GSPYPGIPVE ELFKLLKEGH RMDKPANCTN ELYMMMRDCW HAVPSQRPTF KQLVEDLDRI LTLTTNEEYL DLSQPLEQYS PSYPDTRSSC SSGDDSVFSP DPMPYEPCLP QYPHINGSVK T |
| 14 | FGFR2 ECD | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPDYLE |
| 15 | Anti-FGFR2 Gal-FR22 heavy chain variable region | QVQLKQSGPG LVQPSQSLSI TCTVSGFSLT SFGVHWVRQS PGKGLEWLGV IWSGGSTDYN ADFRSRLSIS KDNSKSQIFF KMNSLQPDDT IAYCANFYYG YDDYVMDYWG QGTSVTVSS |
| 16 | Anti-FGFR2 Gal-FR22 heavy chain CDR1 | SFGVH |
| 17 | Anti-FGFR2 Gal-FR22 heavy chain CDR2 | VIWSGGSTDYNADFRS |
| 18 | Anti-FGFR2 Gal-FR22 heavy chain CDR3 | FYYGYDDYVMDY |
| 19 | Anti-FGFR2 Gal-FR22 light chain variable region | DIQMTQSPSS LSASLGGRVT ITCKASQDIK NYIAWYQHKP GKSPRLLIHY TSTLQPGVPS RFSGSGSGRD YSFSISNLEP EDIATYYCLQ YDDDLYMFGG GTKLDIK |
| 20 | Anti-FGFR2 Gal-FR22 light chain CDR1 | KASQDIKNYIA |
| 21 | Anti-FGFR2 Gal-FR22 light chain CDR2 | YTSTLQP |
| 22 | Anti-FGFR2 Gal-FR22 light chain CDR3 | LQYDDLYM |

What is claimed is:

1. A method of treating locally advanced, unresectable or metastatic gastric cancer that overexpresses FGFR2-IIIb in a subject comprising administering to the subject:
   (a) 6-15 mg/kg of an anti-FGFR2-IIIb antibody every 13-15 days wherein the anti-FGFR2-IIIb antibody is afucosylated and comprises heavy chain and light chain variable regions, wherein the heavy chain variable region comprises:
      (i) a heavy chain hypervariable region H1 (HVR-H1) comprising the amino acid sequence of SEQ ID NO: 6;
      (ii) a HVR-H2 comprising the amino acid sequence of SEQ ID NO: 7; and
      (iii) a HVR-H3 comprising the amino acid sequence of SEQ ID NO: 8;
   and the light chain variable region comprises:
      (iv) a HVR-L1 comprising the amino acid sequence of SEQ ID NO: 9;
      (v) a HVR-L2 comprising the amino acid sequence of SEQ ID NO: 10; and
      (vi) a HVR-L3 comprising the amino acid sequence of SEQ ID NO: 11;
   (b) oxaliplatin, folinic acid, and 5-fluorouracil every 13-15 days; and
   (c) a single dose of 3-8 mg/kg of the anti-FGFR2-IIIb antibody 6-8 days after a first dose of the (a) 6-15 mg/kg of the anti-FGFR2-IIIb antibody and before a second dose of the (a) 6-15 mg/kg anti-FGFR2-IIIb antibody.

2. The method of claim 1, wherein (a) 15 mg/kg of the anti-FGFR2-IIIb antibody is administered to the subject every 14 days, (b) the oxaliplatin, folinic acid, and 5-fluorouracil are administered every 14 days, and (c) the single dose of 7.5 mg/kg of the anti-FGFR2-IIIb antibody is administered 7 days after the first 15 mg/kg dose of the anti-FGFR2-IIIb antibody and before the second 15 mg/kg dose of the anti-FGFR2-IIIb antibody.

3. The method of claim 1, wherein the gastric cancer has been determined to overexpress FGFR2-IIIb as indicated by an IHC signal of 2+ or 3+ in tumor cells and/or wherein the gastric cancer has been determined to have an FGFR2 gene amplification in ctDNA.

4. The method of claim 1, wherein the subject received at least two administrations of oxaliplatin, folinic acid, and 5-fluorouracil prior to the first administration of the anti-FGFR2-IIIb antibody.

5. The method of claim 1, wherein (a) 10-15 mg/kg of the anti-FGFR2-IIIb antibody is administered to the subject every 14 days, (b) the oxaliplatin, folinic acid, and 5-fluorouracil are administered every 14 days, and (c) the single dose of 7-8 mg/kg anti-FGFR2-IIIb antibody is administered 7 days after the first 10-15 mg/kg dose of the anti-FGFR2-IIIb antibody and before the second 10-15 mg/kg dose of the anti-FGFR2-IIIb antibody.

6. The method of claim 1, wherein the heavy chain variable region comprises an amino acid sequence at least 95% identical to the amino acid sequence of SEQ ID NO: 4 and the light chain variable region comprises an amino acid sequence at least 95% identical to the amino acid sequence of SEQ ID NO: 5.

7. The method of claim 1, wherein the heavy chain variable region comprises the amino acid sequence of SEQ ID NO: 4 and the light chain variable region comprises the amino acid sequence of SEQ ID NO: 5.

8. The method of claim 1, wherein the antibody comprises a heavy chain comprising an amino acid sequence at least 95% identical to the amino acid sequence of SEQ ID NO: 2 and a light chain comprising an amino acid sequence at least 95% identical to the amino acid sequence of SEQ ID NO: 3.

9. The method of claim 1, wherein the antibody comprises a heavy chain comprising the amino acid sequence of SEQ ID NO: 2 and a light chain comprising the amino acid sequence of SEQ ID NO: 3.

10. A method of treating gastric cancer that overexpresses FGFR2-IIIb in a subject comprising administering to the subject:
  (a) 15 mg/kg of an afucosylated anti-FGFR2-IIIb antibody once every 14 days, wherein the anti-FGFR2-IIIb antibody comprises a heavy chain amino acid sequence of SEQ ID NO: 2 and a light chain amino acid sequence of SEQ ID NO: 3;
  (b) 85 mg/m$^2$ oxaliplatin, 400 mg/m$^2$ leucovorin, and 400 mg/m$^2$ 5-fluorouracil (5-FU) once every 14 days by IV infusion or IV bolus followed by administration of 2400 mg/m$^2$ 5-FU by IV infusion over 44-48 hours; and
  (c) a single dose of 7.5 mg/kg of the anti-FGFR2-IIIb antibody, administered 7 days after the first dose of the (a) 15 mg/kg dose of the anti-FGFR2-IIIb antibody and before the second dose of the (a) 15 mg/kg of anti-FGFR2-IIIb antibody.

11. The method of claim 10, wherein the gastric cancer has been determined to overexpress FGFR2-IIIb as indicated by an IHC signal of 2+ or 3+ in tumor cells and/or wherein the gastric cancer has been determined to have an FGFR2 gene amplification in ctDNA.

12. The method of claim 10, wherein the subject received at least two administrations of oxaliplatin, folinic acid, and 5-fluorouracil prior to the first administration of the anti-FGFR2-IIIb antibody.

* * * * *

SEQUENCE LISTING

<160> NUMBER OF SEQ ID NOS: 22

<210> SEQ ID NO 1
<211> LENGTH: 801
<212> TYPE: PRT
<213> ORGANISM: Homo sapiens

<400> SEQUENCE: 1

Arg Pro Ser Phe Ser Leu Val Glu Asp Thr Thr Leu Glu Pro Glu Glu

-continued

```
             1               5                  10                 15
             Pro Pro Thr Lys Tyr Gln Ile Ser Gln Pro Glu Val Tyr Val Ala Ala
                             20                 25                 30
             Pro Gly Glu Ser Leu Glu Val Arg Cys Leu Leu Lys Asp Ala Ala Val
                             35                 40                 45
             Ile Ser Trp Thr Lys Asp Gly Val His Leu Gly Pro Asn Asn Arg Thr
                             50                 55                 60
             Val Leu Ile Gly Glu Tyr Leu Gln Ile Lys Gly Ala Thr Pro Arg Asp
              65                 70                 75                 80
             Ser Gly Leu Tyr Ala Cys Thr Ala Ser Arg Thr Val Asp Ser Glu Thr
                                 85                 90                 95
             Trp Tyr Phe Met Val Asn Val Thr Asp Ala Ile Ser Ser Gly Asp Asp
                                100                105                110
             Glu Asp Asp Thr Asp Gly Ala Glu Asp Phe Val Ser Glu Asn Ser Asn
                                115                120                125
             Asn Lys Arg Ala Pro Tyr Trp Thr Asn Thr Glu Lys Met Glu Lys Arg
                            130                135                140
             Leu His Ala Val Pro Ala Ala Asn Thr Val Lys Phe Arg Cys Pro Ala
             145                150                155                160
             Gly Gly Asn Pro Met Pro Thr Met Arg Trp Leu Lys Asn Gly Lys Glu
                                165                170                175
             Phe Lys Gln Glu His Arg Ile Gly Gly Tyr Lys Val Arg Asn Gln His
                            180                185                190
             Trp Ser Leu Ile Met Glu Ser Val Val Pro Ser Asp Lys Gly Asn Tyr
                            195                200                205
             Thr Cys Val Val Glu Asn Glu Tyr Gly Ser Ile Asn His Thr Tyr His
                            210                215                220
             Leu Asp Val Val Glu Arg Ser Pro His Arg Pro Ile Leu Gln Ala Gly
             225                230                235                240
             Leu Pro Ala Asn Ala Ser Thr Val Val Gly Gly Asp Val Glu Phe Val
                            245                250                255
             Cys Lys Val Tyr Ser Asp Ala Gln Pro His Ile Gln Trp Ile Lys His
                            260                265                270
             Val Glu Lys Asn Gly Ser Lys Tyr Gly Pro Asp Gly Leu Pro Tyr Leu
                            275                280                285
             Lys Val Leu Lys His Ser Gly Ile Asn Ser Ser Asn Ala Glu Val Leu
                            290                295                300
             Ala Leu Phe Asn Val Thr Glu Ala Asp Ala Gly Glu Tyr Ile Cys Lys
             305                310                315                320
             Val Ser Asn Tyr Ile Gly Gln Ala Asn Gln Ser Ala Trp Leu Thr Val
                            325                330                335
             Leu Pro Lys Gln Gln Ala Pro Gly Arg Glu Lys Glu Ile Thr Ala Ser
                            340                345                350
             Pro Asp Tyr Leu Glu Ile Ala Ile Tyr Cys Ile Gly Val Phe Leu Ile
                            355                360                365
             Ala Cys Met Val Val Thr Val Ile Leu Cys Arg Met Lys Asn Thr Thr
                            370                375                380
             Lys Lys Pro Asp Phe Ser Ser Gln Pro Ala Val His Lys Leu Thr Lys
             385                390                395                400
             Arg Ile Pro Leu Arg Arg Gln Val Thr Val Ser Ala Glu Ser Ser Ser
                            405                410                415
             Ser Met Asn Ser Asn Thr Pro Leu Val Arg Ile Thr Thr Arg Leu Ser
                            420                425                430
```

```
Ser Thr Ala Asp Thr Pro Met Leu Ala Gly Val Ser Glu Tyr Glu Leu
        435                 440                 445

Pro Glu Asp Pro Lys Trp Glu Phe Pro Arg Asp Lys Leu Thr Leu Gly
    450                 455                 460

Lys Pro Leu Gly Glu Gly Cys Phe Gly Gln Val Val Met Ala Glu Ala
465                 470                 475                 480

Val Gly Ile Asp Lys Asp Lys Pro Lys Glu Ala Val Thr Val Ala Val
                485                 490                 495

Lys Met Leu Lys Asp Asp Ala Thr Glu Lys Asp Leu Ser Asp Leu Val
                500                 505                 510

Ser Glu Met Glu Met Met Lys Met Ile Gly Lys His Lys Asn Ile Ile
            515                 520                 525

Asn Leu Leu Gly Ala Cys Thr Gln Asp Gly Pro Leu Tyr Val Ile Val
        530                 535                 540

Glu Tyr Ala Ser Lys Gly Asn Leu Arg Glu Tyr Leu Arg Ala Arg Arg
545                 550                 555                 560

Pro Pro Gly Met Glu Tyr Ser Tyr Asp Ile Asn Arg Val Pro Glu Glu
                565                 570                 575

Gln Met Thr Phe Lys Asp Leu Val Ser Cys Thr Tyr Gln Leu Ala Arg
                580                 585                 590

Gly Met Glu Tyr Leu Ala Ser Gln Lys Cys Ile His Arg Asp Leu Ala
            595                 600                 605

Ala Arg Asn Val Leu Val Thr Glu Asn Asn Val Met Lys Ile Ala Asp
        610                 615                 620

Phe Gly Leu Ala Arg Asp Ile Asn Asn Ile Asp Tyr Tyr Lys Lys Thr
625                 630                 635                 640

Thr Asn Gly Arg Leu Pro Val Lys Trp Met Ala Pro Glu Ala Leu Phe
                645                 650                 655

Asp Arg Val Tyr Thr His Gln Ser Asp Val Trp Ser Phe Gly Val Leu
                660                 665                 670

Met Trp Glu Ile Phe Thr Leu Gly Gly Ser Pro Tyr Pro Gly Ile Pro
            675                 680                 685

Val Glu Glu Leu Phe Lys Leu Leu Lys Glu Gly His Arg Met Asp Lys
        690                 695                 700

Pro Ala Asn Cys Thr Asn Glu Leu Tyr Met Met Met Arg Asp Cys Trp
705                 710                 715                 720

His Ala Val Pro Ser Gln Arg Pro Thr Phe Lys Gln Leu Val Glu Asp
                725                 730                 735

Leu Asp Arg Ile Leu Thr Leu Thr Thr Asn Glu Glu Tyr Leu Asp Leu
                740                 745                 750

Ser Gln Pro Leu Glu Gln Tyr Ser Pro Ser Tyr Pro Asp Thr Arg Ser
            755                 760                 765

Ser Cys Ser Ser Gly Asp Asp Ser Val Phe Ser Pro Asp Pro Met Pro
        770                 775                 780

Tyr Glu Pro Cys Leu Pro Gln Tyr Pro His Ile Asn Gly Ser Val Lys
785                 790                 795                 800

Thr

<210> SEQ ID NO 2
<211> LENGTH: 444
<212> TYPE: PRT
<213> ORGANISM: Artificial Sequence
<220> FEATURE:
<223> OTHER INFORMATION: alpha-FGFR2b heavy chain
```

```
<220> FEATURE:
<221> NAME/KEY: MISC_FEATURE
<222> LOCATION: (294)..(294)
<223> OTHER INFORMATION: Asn297

<400> SEQUENCE: 2
```

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly |
| 1 | | | | 5 | | | | | 10 | | | | | 15 |
| Ser | Ser | Val | Lys | Val | Ser | Cys | Lys | Ala | Ser | Gly | Tyr | Ile | Phe | Thr |
| | | | 20 | | | | | 25 | | | | | 30 | |
| Thr | Tyr | Asn | Val | His | Trp | Val | Arg | Gln | Ala | Pro | Gly | Gln | Gly | Leu |
| | | | | 35 | | | | | 40 | | | | | 45 |
| Glu | Trp | Ile | Gly | Ser | Ile | Tyr | Pro | Asp | Asn | Gly | Asp | Thr | Ser | Tyr |
| | | | 50 | | | | | 55 | | | | | 60 | |
| Asn | Gln | Asn | Phe | Lys | Gly | Arg | Ala | Thr | Ile | Thr | Ala | Asp | Lys | Ser |
| | | | | 65 | | | | | 70 | | | | | 75 |
| Thr | Ser | Thr | Ala | Tyr | Met | Glu | Leu | Ser | Ser | Leu | Arg | Ser | Glu | Asp |
| | | | | 80 | | | | | 85 | | | | | 90 |
| Thr | Ala | Val | Tyr | Tyr | Cys | Ala | Arg | Gly | Asp | Phe | Ala | Tyr | Trp | Gly |
| | | | | 95 | | | | | 100 | | | | | 105 |
| Gln | Gly | Thr | Leu | Val | Thr | Val | Ser | Ser | Ala | Ser | Thr | Lys | Gly | Pro |
| | | | 110 | | | | | 115 | | | | | 120 | |
| Ser | Val | Phe | Pro | Leu | Ala | Pro | Ser | Ser | Lys | Ser | Thr | Ser | Gly | Gly |
| | | | | 125 | | | | | 130 | | | | | 135 |
| Thr | Ala | Ala | Leu | Gly | Cys | Leu | Val | Lys | Asp | Tyr | Phe | Pro | Glu | Pro |
| | | | | 140 | | | | | 145 | | | | | 150 |
| Val | Thr | Val | Ser | Trp | Asn | Ser | Gly | Ala | Leu | Thr | Ser | Gly | Val | His |
| | | | | 155 | | | | | 160 | | | | | 165 |
| Thr | Phe | Pro | Ala | Val | Leu | Gln | Ser | Ser | Gly | Leu | Tyr | Ser | Leu | Ser |
| | | | | 170 | | | | | 175 | | | | | 180 |
| Ser | Val | Val | Thr | Val | Pro | Ser | Ser | Ser | Leu | Gly | Thr | Gln | Thr | Tyr |
| | | | | 185 | | | | | 190 | | | | | 195 |
| Ile | Cys | Asn | Val | Asn | His | Lys | Pro | Ser | Asn | Thr | Lys | Val | Asp | Lys |
| | | | | 200 | | | | | 205 | | | | | 210 |
| Arg | Val | Glu | Pro | Lys | Ser | Cys | Asp | Lys | Thr | His | Thr | Cys | Pro | Pro |
| | | | | 215 | | | | | 220 | | | | | 225 |
| Cys | Pro | Ala | Pro | Glu | Leu | Leu | Gly | Gly | Pro | Ser | Val | Phe | Leu | Phe |
| | | | | 230 | | | | | 235 | | | | | 240 |
| Pro | Pro | Lys | Pro | Lys | Asp | Thr | Leu | Met | Ile | Ser | Arg | Thr | Pro | Glu |
| | | | | 245 | | | | | 250 | | | | | 255 |
| Val | Thr | Cys | Val | Val | Val | Asp | Val | Ser | His | Glu | Asp | Pro | Glu | Val |
| | | | | 260 | | | | | 265 | | | | | 270 |
| Lys | Phe | Asn | Trp | Tyr | Val | Asp | Gly | Val | Glu | Val | His | Asn | Ala | Lys |
| | | | | 275 | | | | | 280 | | | | | 285 |
| Thr | Lys | Pro | Arg | Glu | Glu | Gln | Tyr | Asn | Ser | Thr | Tyr | Arg | Val | Val |
| | | | | 290 | | | | | 295 | | | | | 300 |
| Ser | Val | Leu | Thr | Val | Leu | His | Gln | Asp | Trp | Leu | Asn | Gly | Lys | Glu |
| | | | | 305 | | | | | 310 | | | | | 315 |
| Tyr | Lys | Cys | Lys | Val | Ser | Asn | Lys | Ala | Leu | Pro | Ala | Pro | Ile | Glu |
| | | | | 320 | | | | | 325 | | | | | 330 |
| Lys | Thr | Ile | Ser | Lys | Ala | Lys | Gly | Gln | Pro | Arg | Glu | Pro | Gln | Val |
| | | | | 335 | | | | | 340 | | | | | 345 |
| Tyr | Thr | Leu | Pro | Pro | Ser | Arg | Glu | Glu | Met | Thr | Lys | Asn | Gln | Val |
| | | | | 350 | | | | | 355 | | | | | 360 |
| Ser | Leu | Thr | Cys | Leu | Val | Lys | Gly | Phe | Tyr | Pro | Ser | Asp | Ile | Ala |
| | | | | 365 | | | | | 370 | | | | | 375 |
| Val | Glu | Trp | Glu | Ser | Asn | Gly | Gln | Pro | | | | | | |
| | | | | 380 | | | | | | | | | | |

```
Glu Asn Asn Tyr Lys Thr Thr Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 3
<211> LENGTH: 214
<212> TYPE: PRT
<213> ORGANISM: Artificial Sequence
<220> FEATURE:
<223> OTHER INFORMATION: Anti-FGFR2b light chain

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Val Ser Asn Asp
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Ser Thr Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 114
<212> TYPE: PRT
<213> ORGANISM: Artificial Sequence
<220> FEATURE:
<223> OTHER INFORMATION: Anti-FGFR2b heavy chain variable region

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Thr Tyr
            20                  25                  30
```

Asn Val His Trp Val Arg Gln Ala Pro Gly Gln Gly Leu Glu Trp Ile
            35                  40                  45

Gly Ser Ile Tyr Pro Asp Asn Gly Asp Thr Ser Tyr Asn Gln Asn Phe
        50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Ala Tyr Trp Gly Gln Gly Thr Leu Val Thr Val
            100                 105                 110

Ser Ser

<210> SEQ ID NO 5
<211> LENGTH: 107
<212> TYPE: PRT
<213> ORGANISM: Artificial Sequence
<220> FEATURE:
<223> OTHER INFORMATION: Anti-FGFR2b light chain variable region

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Val Ser Asn Asp
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Ser Thr Thr Pro Tyr
                85                  90                  95

Thr Phe Gly Gln Gly Thr Lys Leu Glu Ile Lys
            100                 105

<210> SEQ ID NO 6
<211> LENGTH: 5
<212> TYPE: PRT
<213> ORGANISM: Artificial Sequence
<220> FEATURE:
<223> OTHER INFORMATION: Anti-FGFR2b heavy chain (HC) HVR1

<400> SEQUENCE: 6

Thr Tyr Asn Val His
1               5

<210> SEQ ID NO 7
<211> LENGTH: 17
<212> TYPE: PRT
<213> ORGANISM: Artificial Sequence
<220> FEATURE:
<223> OTHER INFORMATION: Anti-FGFR2b HC HVR2

<400> SEQUENCE: 7

Ser Ile Tyr Pro Asp Asn Gly Asp Thr Ser Tyr Asn Gln Asn Phe Lys
1               5                   10                  15

Gly

<210> SEQ ID NO 8

```
<211> LENGTH: 5
<212> TYPE: PRT
<213> ORGANISM: Artificial Sequence
<220> FEATURE:
<223> OTHER INFORMATION: Anti-FGFR2b HC HVR3

<400> SEQUENCE: 8

Gly Asp Phe Ala Tyr
1               5

<210> SEQ ID NO 9
<211> LENGTH: 11
<212> TYPE: PRT
<213> ORGANISM: Artificial Sequence
<220> FEATURE:
<223> OTHER INFORMATION: Anti-FGFR2b light chain (LC) HVR1

<400> SEQUENCE: 9

Lys Ala Ser Gln Gly Val Ser Asn Asp Val Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Anti-FGFR2b LC HVR2

<400> SEQUENCE: 10

Ser Ala Ser Tyr Arg Tyr Thr
1               5

<210> SEQ ID NO 11
<211> LENGTH: 9
<212> TYPE: PRT
<213> ORGANISM: Artificial Sequence
<220> FEATURE:
<223> OTHER INFORMATION: Anti-FGFR2b LC HVR3

<400> SEQUENCE: 11

Gln Gln His Ser Thr Thr Pro Tyr Thr
1               5

<210> SEQ ID NO 12
<211> LENGTH: 444
<212> TYPE: PRT
<213> ORGANISM: Artificial Sequence
<220> FEATURE:
<223> OTHER INFORMATION: Anti-FGFR2b N297Q heavy chain
<220> FEATURE:
<221> NAME/KEY: MISC_FEATURE
<222> LOCATION: (294)..(294)
<223> OTHER INFORMATION: N297Q

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Thr Tyr
                20                  25                  30

Asn Val His Trp Val Arg Gln Ala Pro Gly Gln Gly Leu Glu Trp Ile
            35                  40                  45

Gly Ser Ile Tyr Pro Asp Asn Gly Asp Thr Ser Tyr Asn Gln Asn Phe
        50                  55                  60

Lys Gly Arg Ala Thr Ile Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Gly Asp Phe Ala Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Arg Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Gln Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 13
<211> LENGTH: 800
<212> TYPE: PRT
<213> ORGANISM: Homo sapiens

<400> SEQUENCE: 13

Arg Pro Ser Phe Ser Leu Val Glu Asp Thr Thr Leu Glu Pro Glu Glu
1               5                   10                  15
```

-continued

```
Pro Pro Thr Lys Tyr Gln Ile Ser Gln Pro Glu Val Tyr Val Ala Ala
             20                  25                  30

Pro Gly Glu Ser Leu Glu Val Arg Cys Leu Leu Lys Asp Ala Ala Val
         35                  40                  45

Ile Ser Trp Thr Lys Asp Gly Val His Leu Gly Pro Asn Asn Arg Thr
 50                  55                  60

Val Leu Ile Gly Glu Tyr Leu Gln Ile Lys Gly Ala Thr Pro Arg Asp
 65                  70                  75                  80

Ser Gly Leu Tyr Ala Cys Thr Ala Ser Arg Thr Val Asp Ser Glu Thr
                 85                  90                  95

Trp Tyr Phe Met Val Asn Val Thr Asp Ala Ile Ser Ser Gly Asp Asp
             100                 105                 110

Glu Asp Asp Thr Asp Gly Ala Glu Asp Phe Val Ser Glu Asn Ser Asn
         115                 120                 125

Asn Lys Arg Ala Pro Tyr Trp Thr Asn Thr Glu Lys Met Glu Lys Arg
130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                 165                 170                 175

Phe Lys Gln Glu His Arg Ile Gly Gly Tyr Lys Val Arg Asn Gln His
             180                 185                 190

Trp Ser Leu Ile Met Glu Ser Val Val Pro Ser Asp Lys Gly Asn Tyr
         195                 200                 205

Thr Cys Val Val Glu Asn Glu Tyr Gly Ser Ile Asn His Thr Tyr His
210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                 245                 250                 255

Cys Lys Val Tyr Ser Asp Ala Gln Pro His Ile Gln Trp Ile Lys His
             260                 265                 270

Val Glu Lys Asn Gly Ser Lys Tyr Gly Pro Asp Gly Leu Pro Tyr Leu
         275                 280                 285

Lys Val Leu Lys Ala Ala Gly Val Asn Thr Thr Asp Lys Glu Ile Glu
290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                 325                 330                 335

Thr Val Leu Pro Ala Pro Gly Arg Glu Lys Glu Ile Thr Ala Ser Pro
             340                 345                 350

Asp Tyr Leu Glu Ile Ala Ile Tyr Cys Ile Gly Val Phe Leu Ile Ala
         355                 360                 365

Cys Met Val Val Thr Val Ile Leu Cys Arg Met Lys Asn Thr Thr Lys
370                 375                 380

Lys Pro Asp Phe Ser Ser Gln Pro Ala Val His Lys Leu Thr Lys Arg
385                 390                 395                 400

Ile Pro Leu Arg Arg Gln Val Thr Val Ser Ala Glu Ser Ser Ser Ser
                 405                 410                 415

Met Asn Ser Asn Thr Pro Leu Val Arg Ile Thr Thr Arg Leu Ser Ser
             420                 425                 430
```

```
Thr Ala Asp Thr Pro Met Leu Ala Gly Val Ser Glu Tyr Glu Leu Pro
            435                 440                 445
Glu Asp Pro Lys Trp Glu Phe Pro Arg Asp Lys Leu Thr Leu Gly Lys
450                 455                 460
Pro Leu Gly Glu Gly Cys Phe Gly Gln Val Val Met Ala Glu Ala Val
465                 470                 475                 480
Gly Ile Asp Lys Asp Lys Pro Lys Glu Ala Val Thr Val Ala Val Lys
                485                 490                 495
Met Leu Lys Asp Asp Ala Thr Glu Lys Asp Leu Ser Asp Leu Val Ser
            500                 505                 510
Glu Met Glu Met Met Lys Met Ile Gly Lys His Lys Asn Ile Ile Asn
            515                 520                 525
Leu Leu Gly Ala Cys Thr Gln Asp Gly Pro Leu Tyr Val Ile Val Glu
            530                 535                 540
Tyr Ala Ser Lys Gly Asn Leu Arg Glu Tyr Leu Arg Ala Arg Arg Pro
545                 550                 555                 560
Pro Gly Met Glu Tyr Ser Tyr Asp Ile Asn Arg Val Pro Glu Glu Gln
                565                 570                 575
Met Thr Phe Lys Asp Leu Val Ser Cys Thr Tyr Gln Leu Ala Arg Gly
            580                 585                 590
Met Glu Tyr Leu Ala Ser Gln Lys Cys Ile His Arg Asp Leu Ala Ala
            595                 600                 605
Arg Asn Val Leu Val Thr Glu Asn Asn Val Met Lys Ile Ala Asp Phe
            610                 615                 620
Gly Leu Ala Arg Asp Ile Asn Asn Ile Asp Tyr Tyr Lys Lys Thr Thr
625                 630                 635                 640
Asn Gly Arg Leu Pro Val Lys Trp Met Ala Pro Glu Ala Leu Phe Asp
                645                 650                 655
Arg Val Tyr Thr His Gln Ser Asp Val Trp Ser Phe Gly Val Leu Met
            660                 665                 670
Trp Glu Ile Phe Thr Leu Gly Gly Ser Pro Tyr Pro Gly Ile Pro Val
            675                 680                 685
Glu Glu Leu Phe Lys Leu Leu Lys Glu Gly His Arg Met Asp Lys Pro
690                 695                 700
Ala Asn Cys Thr Asn Glu Leu Tyr Met Met Met Arg Asp Cys Trp His
705                 710                 715                 720
Ala Val Pro Ser Gln Arg Pro Thr Phe Lys Gln Leu Val Glu Asp Leu
                725                 730                 735
Asp Arg Ile Leu Thr Leu Thr Asn Glu Glu Tyr Leu Asp Leu Ser
            740                 745                 750
Gln Pro Leu Glu Gln Tyr Ser Pro Ser Tyr Pro Asp Thr Arg Ser Ser
            755                 760                 765
Cys Ser Ser Gly Asp Asp Ser Val Phe Ser Pro Asp Pro Met Pro Tyr
770                 775                 780
Glu Pro Cys Leu Pro Gln Tyr Pro His Ile Asn Gly Ser Val Lys Thr
785                 790                 795                 800

<210> SEQ ID NO 14
<211> LENGTH: 356
<212> TYPE: PRT
<213> ORGANISM: Homo sapiens

<400> SEQUENCE: 14

Arg Pro Ser Phe Ser Leu Val Glu Asp Thr Thr Leu Glu Pro Glu Glu
1               5                   10                  15
```

```
Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
        35                  40                  45

Ile Ser Trp Thr Lys Asp Gly Val His Leu Gly Pro Asn Asn Arg Thr
50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
            100                 105                 110

Glu Asp Asp Thr Asp Gly Ala Glu Asp Phe Val Ser Glu Asn Ser Asn
        115                 120                 125

Asn Lys Arg Ala Pro Tyr Trp Thr Asn Thr Glu Lys Met Glu Lys Arg
130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
        195                 200                 205

Thr Cys Val Val Glu Asn Glu Tyr Gly Ser Ile Asn His Thr Tyr His
210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
        275                 280                 285

Lys Val Leu Lys Ala Ala Gly Val Asn Thr Thr Asp Lys Glu Ile Glu
290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys Glu Ile Thr Ala Ser Pro
            340                 345                 350

Asp Tyr Leu Glu
        355

<210> SEQ ID NO 15
<211> LENGTH: 119
<212> TYPE: PRT
<213> ORGANISM: Artificial Sequence
<220> FEATURE:
<223> OTHER INFORMATION: Anti-FGFR2 Gal-FR22 heavy chain variable region

<400> SEQUENCE: 15

Gln Val Gln Leu Lys Gln Ser Gly Pro Gly Leu Val Gln Pro Ser Gln
1               5                   10                  15
```

-continued

```
Ser Leu Ser Ile Thr Cys Thr Val Ser Gly Phe Ser Leu Thr Ser Phe
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Asp Phe Arg
 50                  55                  60

Ser Arg Leu Ser Ile Ser Lys Asp Asn Ser Lys Ser Gln Ile Phe Phe
 65                  70                  75                  80

Lys Met Asn Ser Leu Gln Pro Asp Asp Thr Ile Ala Tyr Cys Ala Asn
                85                  90                  95

Phe Tyr Tyr Gly Tyr Asp Asp Tyr Val Met Asp Tyr Trp Gly Gln Gly
            100                 105                 110

Thr Ser Val Thr Val Ser Ser
        115
```

<210> SEQ ID NO 16
<211> LENGTH: 5
<212> TYPE: PRT
<213> ORGANISM: Artificial Sequence
<220> FEATURE:
<223> OTHER INFORMATION: Anti-FGFR2 Gal-FR22 heavy chain CDR1

<400> SEQUENCE: 16

```
Ser Phe Gly Val His
1               5
```

<210> SEQ ID NO 17
<211> LENGTH: 16
<212> TYPE: PRT
<213> ORGANISM: Artificial Sequence
<220> FEATURE:
<223> OTHER INFORMATION: Anti-FGFR2 Gal-FR22 heavy chain CDR2

<400> SEQUENCE: 17

```
Val Ile Trp Ser Gly Gly Ser Thr Asp Tyr Asn Ala Asp Phe Arg Ser
1               5                   10                  15
```

<210> SEQ ID NO 18
<211> LENGTH: 12
<212> TYPE: PRT
<213> ORGANISM: Artificial Sequence
<220> FEATURE:
<223> OTHER INFORMATION: Anti-FGFR2 Gal-FR22 heavy chain CDR3

<400> SEQUENCE: 18

```
Phe Tyr Tyr Gly Tyr Asp Asp Tyr Val Met Asp Tyr
1               5                   10
```

<210> SEQ ID NO 19
<211> LENGTH: 107
<212> TYPE: PRT
<213> ORGANISM: Artificial Sequence
<220> FEATURE:
<223> OTHER INFORMATION: Anti-FGFR2 Gal-FR22 light chain variable region

<400> SEQUENCE: 19

```
Asp Ile Gln Met Thr Gln Ser Pro Ser Ser Leu Ser Ala Ser Leu Gly
1               5                   10                  15

Gly Arg Val Thr Ile Thr Cys Lys Ala Ser Gln Asp Ile Lys Asn Tyr
            20                  25                  30

Ile Ala Trp Tyr Gln His Lys Pro Gly Lys Ser Pro Arg Leu Leu Ile
        35                  40                  45
```

```
His Tyr Thr Ser Thr Leu Gln Pro Gly Val Pro Ser Arg Phe Ser Gly
            50                  55                  60

Ser Gly Ser Gly Arg Asp Tyr Ser Phe Ser Ile Ser Asn Leu Glu Pro
 65              70                  75                  80

Glu Asp Ile Ala Thr Tyr Tyr Cys Leu Gln Tyr Asp Asp Leu Tyr
                85                  90                  95

Met Phe Gly Gly Gly Thr Lys Leu Asp Ile Lys
            100                 105

<210> SEQ ID NO 20
<211> LENGTH: 11
<212> TYPE: PRT
<213> ORGANISM: Artificial Sequence
<220> FEATURE:
<223> OTHER INFORMATION: Anti-FGFR2 Gal-FR22 light chain CDR1

<400> SEQUENCE: 20

Lys Ala Ser Gln Asp Ile Lys Asn Tyr Ile Ala
 1               5                  10

<210> SEQ ID NO 21
<211> LENGTH: 7
<212> TYPE: PRT
<213> ORGANISM: Artificial Sequence
<220> FEATURE:
<223> OTHER INFORMATION: Anti-FGFR2 Gal-FR22 light chain CDR2

<400> SEQUENCE: 21

Tyr Thr Ser Thr Leu Gln Pro
 1               5

<210> SEQ ID NO 22
<211> LENGTH: 8
<212> TYPE: PRT
<213> ORGANISM: Artificial Sequence
<220> FEATURE:
<223> OTHER INFORMATION: Anti-FGFR2 Gal-FR22 light chain CDR3

<400> SEQUENCE: 22

Leu Gln Tyr Asp Asp Leu Tyr Met
 1               5
```